US007812124B2

(12) United States Patent
Palm

(10) Patent No.: US 7,812,124 B2
(45) Date of Patent: Oct. 12, 2010

(54) PROFILING TUMOR SPECIFIC MARKERS FOR THE DIAGNOSIS AND TREATMENT OF NEOPLASTIC DISEASE

(76) Inventor: Kaia Palm, 1123 9th St., Apt. 10, Santa Monica, CA (US) 90403

(*) Notice: Subject to any disclaimer, the term of this patent is extended or adjusted under 35 U.S.C. 154(b) by 0 days.

(21) Appl. No.: 11/606,786

(22) Filed: Nov. 30, 2006

(65) Prior Publication Data
US 2007/0161023 A1 Jul. 12, 2007

Related U.S. Application Data

(63) Continuation of application No. 09/992,665, filed on Nov. 13, 2001, now abandoned.

(60) Provisional application No. 60/249,508, filed on Nov. 16, 2000.

(51) Int. Cl.
C07K 14/00 (2006.01)
(52) U.S. Cl. .......................... 530/350; 435/7.1
(58) Field of Classification Search ................. 530/350; 435/7.1
See application file for complete search history.

(56) References Cited

U.S. PATENT DOCUMENTS

| 5,795,723 | A | * | 8/1998 | Tapscott et al. ................ 435/6 |
| 5,807,522 | A | * | 9/1998 | Brown et al. .................. 422/50 |
| 5,939,258 | A | | 8/1999 | Croce et al. |
| 6,218,122 | B1 | | 4/2001 | Friend et al. |
| 6,333,152 | B1 | | 12/2001 | Vogelstein et al. |
| 6,368,794 | B1 | | 4/2002 | Daniel et al. |
| 6,399,298 | B1 | | 6/2002 | Li et al. |
| 6,440,676 | B1 | | 8/2002 | Kroes et al. |
| 6,838,444 | B1 | * | 1/2005 | Zoghbi et al. ............. 514/44 R |
| 2002/0142981 | A1 | | 10/2002 | Horne et al. |

FOREIGN PATENT DOCUMENTS

| WO | WO 99/07725 A | 2/1999 |
| WO | WO 99/44062 | 9/1999 |
| WO | WO 00/70430 | 11/2000 |
| WO | WO0121136 | 3/2001 |
| WO | WO 02/08419 | 1/2002 |
| WO | WO 02/22884 | 3/2002 |
| WO | WO 02/30268 | 4/2002 |
| WO | WO 02/081638 | 10/2002 |
| WO | WO 02/096951 | 12/2002 |

OTHER PUBLICATIONS

Gure et al, Apr. 2000, PNAS, USA, 97(8): 4198-4203.*
Genus et al, Sep. 2000, J Medical Genetics, 37 (Suppl 1): S40, abstract # 1.23.*
Sambrook et al., 1989 Molecular Cloning, A Laboratory Manual, Cold Springs Harbor Press, N.Y.
Ausubel et al., 1989 Current Protocols in Molecular Biology, Green Publishing Associates and Wiley Interscience, N.Y.
Timmusk, et al. Neuron 10(3), 475-489 (1993).
Palm, et al., Brain Res. 78(1-2), 192-195 (2000).
Annex to Form PCT/ISA/206: PCT/US01/143461, Date of Mailing: Nov. 7, 2002.
Martin, K. J. et al., "Linking Gene Expression Patterns to Therapeutic Groups in Breast Cancer", Cancer Research, American Association for Cancer Research, vol. 60, No. 8, pp. 2232-2238. Apr. 15, 2000.
Alizadeh A. A. et al., "Distinct Types of Diffuse Large B-Cell Lymphoma Identified by Gene Expression Profiling", Nature, MacMillan Journals Ltd., vol. 403, pp. 503-512, Feb. 3, 2000.
Frohme M. et al., Use of Representational Difference Analysis and CDNA Arrays for Transcriptional Profiling of Tumor Tissue; Annals of the New York Academy of Sciences, vol. 910, pp. 85-105, 2000.
Anbazhagan, R. et al., Classification of Small Cell Lung Cancer and Pulmonary Carcinoid Bygene Expression Profiles, Cancer Research, American Association for Cancer Research, vol. 59, pp. 5119-5122, Oct. 15, 1999.
Lueking A. et al., "Protein Microarrays for Gene Expression and Antibody Screening", Analytical Biochemistry, vol. 270, No. 1, pp. 103-111, May 1999.
Gure, A. O., et al., "Serological Identification of Embryonic Neural Proteins as Highly Immunogenic Tumor Antigens in Small Cell Lung-Cancer", Proceedings of the National Academy of Science, vol. 97, No. 8, pp. 4198-4203, Apr. 11, 2000.
McCormick, Mary B. et al., "NeuroD2 and NeuroD3: Distinct Expression Patterns and Transcriptional Activation Potentials within the NeuroD Gene Family", Molecular and Cellular Biology, vol. 16, No. 10, pp. 5792-5800.
Masai, I. et al., Midline Signals Regulate Retinal Neurogenesis in Zebrafish, Neuron, US, vol. 27, No. 2, pp. 251-263, Aug. 2000.
Brown, Nadean L. et al., "Math5 is Required for Retinal Ganglion Cell and Optic Nerve Formation", Development, vol. 128, No. 13, pp. 2497-2508, Jul. 2001.
Database Medline (Online), Hermanson O. et al., "Expression of LMO-4 in the Central Nervous System of the Embryonic an Adult Mouse", Database Accession No. NLM10512198XP002215211, Abstract (Jul. 1999), and Cellular and Molecular Biology, vol. 45, No. 5, pp. 677-686, Jul. 1999.
Colombo, M. P. et al., "Cytokine Gene Transfer in Tumor Inhibition and Tumor Therapy: Where Are We Now"? Immunology Today, Elsevier Publications, vol. 2, No. 15, pp. 48-51, 1994.
Kononen et al., "Tissue Microarrays for High-Throughput Molecular Profiling of Tumor Specimens", Nature Medicine, vol. 4, No. 7, pp. 844-847, Jul. 1998.
Cox, P. M. et al., "Transcription and Cancer", British Journal of Cancer, vol. 63, No. 5, pp. 651-662.

(Continued)

Primary Examiner—Larry R. Helms
Assistant Examiner—Minh-Tam Davis
(74) Attorney, Agent, or Firm—Todd Lorenz

(57) ABSTRACT

A method of diagnosing cancer comprising the identification of neoplastic molecular markers is disclosed. Tumor-related or neoplastic molecular markers are identified from samples taken from a subject and the molecular profile of those markers is determined. Based upon the neoplastic molecular marker profile of the subject, the tumor sub-type is ascertained and an appropriate treatment protocols initiated.

3 Claims, No Drawings

OTHER PUBLICATIONS

Lee, J. E., "Basic Helix-Loop—Helix Genes in Neural Development", *Current Opinion in Neurobiology*, vol. 7, No. 1, pp. 13-20, Feb. 1997.

Stockert et al., *J. Exp. Med.* 1998, 187:1349-1354.

Winter, S. F. et al., "Development of Antibodies Against P53 in Lung Cancer Patients Appears Dependent on the Type of P3 Mutation", Simmons Cancer Center, University of Texas Southwestern Medical Center, Dallas, TX 75235 and National Cancer Institute/Navy Medical Oncology Branch, NIH, Bethesda, Maryland 20889.

Mudenda, B et al., "The relationship between serum Ltd3 antibodies and characteristics of human breast cancer", Br. J. Cancer (1994)1115-1119 MacMillan Press.

Katoh et al., (Int J. Mol. Med.) 2004 14:747-751.

Palm et al. "Tracing the Neural Origins of Carcinoid Tumours May Lead to a Novel Approach to Diagnosis and Gene Therapy", Presented in 8th International Conference on Gene Therapy of Cancer, Dec. 8-11, 1999, San Diego, CA.

* cited by examiner

PROFILING TUMOR SPECIFIC MARKERS FOR THE DIAGNOSIS AND TREATMENT OF NEOPLASTIC DISEASE

RELATED APPLICATIONS

This application is a continuation of U.S. patent application Ser. No. 09/992,665, filed Nov. 13, 2001, now abandoned, which claims priority to U.S. Provisional Patent Application No. 60/249,508, filed on Nov. 16, 2000, which is hereby incorporated by reference in its entirety.

FIELD OF THE INVENTION

The description below relates to the use of marker systems found in a subject for the diagnosis of neoplastic diseases, including tumors with neural and neuroendocrine differentiation. In a preferred embodiment, a subject's auto-antibody profile is developed and molecular characteristics of a particular neoplasm afflicting the subject are determined.

BACKGROUND OF THE INVENTION

The American Cancer Society predicts that 1.27 million new cases of cancer will be diagnosed in the United States in 2001. The number of cancer-related deaths for 2001 are predicted to include: 157,400 deaths from lung cancer, 31,500 deaths from prostate cancer, 40,000 deaths from breast cancer, and 56,700 deaths from colorectal cancer. Lung, prostate, breast, and colon cancer are the most common tumors.

Early detection of neoplastic disease (cancer) is critical to ensure favorable treatment of the disease. When patients go to seek for treatment, they are generally presenting with symptoms due to distant metastases, meaning that too often the cancer is detected too late. Therefore, the ability to detect and diagnose cancer through the identification of tumor markers is an area of widespread interest.

It is therefore of interest to identify early stage cancers with neural and/or neuroendocrine components/differentiation in a minimally invasive manner. In particular, it would be a great boon to the treatment of cancers to identify an array of tumor-associated antigens that are specific for the cancer type. An antibody raised against such antigens can be used in the diagnosis and targeted treatment of neoplastic diseases. Auto-antibodies against such antigens generated as a part of subject's immune response can be used in the diagnosis of neoplastic diseases.

SUMMARY OF THE INVENTION

The disclosure below encompasses a method for determining the presence of neoplastic molecular markers in a host comprising: a) obtaining a test sample from the host, wherein the host is suspected of having a neoplastic disease, b) determining the presence of one or more neoplastic molecular markers in the test sample, and c) analyzing the presence of one or more neoplastic molecular markers, wherein the analysis permits the identification of the neoplastic disease. Examples of neoplastic diseases that can be detected by the disclosed methods include lung cancer, prostate cancer, neuroblastoma and astrocytoma.

The disclosure further encompasses an array of neoplastic molecular markers arranged in an assayable format.

Further, the methods disclosed relate to a method of diagnosing a neoplastic disease comprising: providing an assay sample isolated from a subject suspected of having a neoplasm, determining the presence of one or more neoplastic molecular markers in the subject, and identifying the neoplastic disease from the presence of neoplastic molecular markers determined.

A method of treating a neoplastic disease is also disclosed. This method comprises providing an assay sample isolated from a subject suspected of having a neoplasm, determining the presence of one or more neoplastic molecular markers in the sample, identifying the neoplastic disease from the presence of neoplastic molecular markers determined, and selecting a therapeutic protocol based upon a correlation between particular therapeutic regimes and particular neoplastic disease states.

DETAILED DESCRIPTION OF THE PREFERRED EMBODIMENT

The description below relates to the molecular characterization of a variety of neoplastic diseases based on qualitative and quantitative characteristics of the particular neoplasm. The term "molecular characterization" relates to the use of various biochemical markers to identify the presence of a neoplasm in a subject and further to positively identify the specific type of neoplasm afflicting the subject. In a preferred embodiment, changes in expression patterns of various genes associated with a neoplastic disease or in a subject's blood antibody profile are used as neoplastic molecular markers with which to identify neoplastic disease for therapeutic and diagnostic purposes.

Determining the presence of particular neoplastic molecular markers is achieved using a number of well-known techniques that indicate the presence of a particular set of markers. For example, immunological assays can be used to determine the presence of a subject's immunogenic response to a neoplastic molecular marker. Biochemical assays that determine gene expression levels and other indicia of increased expression in a cell can also be used with the methods described herein.

As used herein, an array of neoplastic molecular markers refers to a non-random arrangement of markers or reagents in a matrix for the detection of neoplastic markers. The array can be in any form that will permit the detection of the presence of particular neoplastic molecular markers. For example, the array can be assembled on a multi-well plate, in an assembly of tubes, or immobilized to a structure. In one embodiment, a typical multi-well plate can be used assay a matrix for an array of peptides against which the presence of particular antibodies is detected. In another embodiment, the multi-well plate contains various PCR primer pairs that are used to amplify a particular message. In another embodiment, probes can be immobilized to a matrix for detection, as is described in U.S. Pat. No. 6,303,288, which is hereby incorporated by reference in its entirety.

Neoplasms

The spectrum of disease states commonly referred to as cancer all relate to various types of uncontrolled or neoplastic cell growth. As a normal cell transitions from a normal phenotype to a neoplastic phenotype, the gene expression patterns of the normal cell change from a normal phenotype expression pattern to a neoplastic phenotype expression pattern. Moreover, these neoplastic gene expression patterns are different, depending on the source and nature of the neoplasm.

Neoplastic phenotypes have a number of characteristics that can be exploited for diagnostic and therapeutic purposes. For example, a neoplastic cell can be characterized by the loss or acquisition of cell surface antigenic components as compared to a wildtype cell. A neoplastic cell may also demonstrate the acquisition of neoantigen expression that is absent from a normal cell. Alternatively, a neoplastic cell can demonstrate an increase in the expression of various genes, particularly transcription factors, as compared to a normal cell. Additionally, a neoplastic cell can demonstrate changes that influence cell-cell interactions in the host. These are just a few examples of the numerable alterations in gene expression patterns typically present in a neoplastic cell. As disclosed below, the various genes that are differentially expressed in a neoplastic cell can be used as neoplastic molecular markers for diagnostic and therapeutic purposes.

Neoplastic Molecular Markers

Neoplastic molecular markers are biochemical markers arising from or related to genes that are differentially or differently expressed by neoplastic cells as compared to a normal or non-neoplastic cell. The normal function of the genes that constitute a neoplastic molecular marker is not significant to the disclosed methods. Accordingly, the function of such markers vary and include but are not limited to metabolic proteins, structural proteins, regulatory proteins, signaling proteins, secretory proteins, apoptotic proteins, mitochondrial proteins, glycoproteins, and glycolipids.

In some cases, neoplastic molecular markers are expressed in normal cells as well as by neoplastic or tumor cells. In tumor cells however, the expression of the neoplastic molecular marker gene is in some way atypical a compared to a normal cell. For example, the expression pattern of a neoplastic molecular marker gene may be greatly increased or greatly decreased when compared to the expression pattern of the marker gene in a non-neoplastic cell.

Another example of differential activity of a neoplastic molecular marker comprises post-translational modifications of the protein produced from the expressed marker gene. Alterations of the post-translational modifications made to the neoplastic molecular marker may alter the immunological characteristics of the protein, e.g., may make the gene product immunogenic to the subject whereas the wildtype form of the protein is not immunogenic. Additionally various functional characteristics of the produced protein may be altered in the neoplastic state. Example of a functional characteristic that can be altered in a neoplastic cell as compared to a wildtype cell is the level of activity exhibited by an enzyme or the half-life of a cell surface marker on the surface of the host cell. Further, a neoplastic molecular marker might may be released or shed from a neoplastic cell while the protein is retained in the normal cell. These are just a few examples of how a gene that is normally expressed in a non-neoplastic cell can be differentially expressed in a neoplastic cell.

Transcription Factors as Neoplastic Molecular Markers

Often in neoplasmic systems, distinct expression patterns of transcriptional modulators can be used to identify neoplasms in a subject. Accordingly, the molecular characterization of transcriptional modulator expression profiles can be used to identify the presence of particular neoplasms in a subject.

Transcriptional modulators include factors that alter chromatin structure to permit access of the transcriptional components to the target gene of interest. One group of promoter restructuring factors that perturbs chromatin in an ATP-dependent manner includes NURF, CHRAC, ACF, the SWI/SNF complex, and SWI/SNF-related (RUSH) proteins.

Another group of transcription modulating factors is involved in the recruitment of a TATA-binding protein (TBP)- containing and not-containing (Intiator) complexes. Examples of general initiation factors include: TFIIB, TFIID, TFIIE, TFIIF, and TFIIH. Each of these general initiation factors are thought to function in intimate association with RNA polymerase II and are required for selective binding of polymerase to its promoters. Additional factors such as TATA-binding protein (TBP), TBP-homologs (TRP, TRF2), initiators that coordinate the interaction of these proteins by recognizing the core promoter element TATA-box or initiator sequence and supplying a scaffolding upon which the rest of the transcriptional machinery can assemble are also considered transcription modulating factors.

Further, TBP-associated factors (TAFs) that function as promoter-recognition factors, as coactivators capable of transducing signals from enhancer-bound activators to the basal machinery, and even as enzymatic modifiers of other proteins are also transcription modulators. Particular examples of transcription modulators include: the TAFIIA complex: (TAFIIAa; TAFIIAb; TAFIIAg); the TAFIIB complex: (TAFIIB; RAP74; RAP30); TAFs forming the TFIID complex (TAFII250; CIF150; TAF130/135; TAFII100; TAFII70/80; TAFII31/32; TAFII20; TAFII15; TAFII28; TAFII68; TAFII55; TAFII30; TAFII18; TAFII105); the TAFIIE complex: (TAFIIEa; TAFIIEb); the TAFIIF complex (p62; p52; MAT1; p34; XPD/ERCC2; p44; XPB/ERCC3; Cdk7; CyclinH); the RNA polymerase II complex: (hRPB1, hRPB2, hRPB3, hRPB4, hRPB5, hRPB6, hRPB7, hRPB8, hRPB9, hRPB10, hRPB11, hRPB12); and others.

Mediators that act as a conserved interface between gene-specific regulatory proteins and the general transcription apparatus of eukaryotes are also considered to be transcription modulators. Typically, this type of mediator complex integrates and transduces positive and negative regulatory information from enhancers and operators to promoters. They typically function directly through RNA polymerase II, modulating its activity in promoter-dependent transcription. Examples of such mediators that form coactivator complexes with TRAP, DRIP, ARC, CRSP, Med, SMCC, NAT, include: TRAP240/DRIP250; TRAP230/DRIP240; DRIP205/CRSP200/TRIP2/PBP/RB18A/TRAP220; hRGR1/CRSP150/DRIP150/TRAP170, TRAP150; CRSP130/hSur-2/DRIP130; TIG-1; CRSP100/TRAP100/DRIP100; DRIP97; DRIP92/TRAP95; CRSP85; CRSP77/DRIP77/TRAP80; CRSP70/DRIP70; Ring3; hSRB10/hCDK8; DRIP36/hMEDp34; CRSP34; CRSP33/hMED7; hMED6; hSRB11/hCyclin C; hSOH1; hSRB7; and others. Additional modulators in this class include proteins of the androgen receptor complex, such as: ANPK; ARIP3; PIAS family (PI-ASα, PIASβ, PIASγ); ARIP4; and transcriptional co-repressors such as: the N-CoR and SMRT families NCOR2/SMRT/TRAC1/CTG26/TNRC14/SMRTE); REA; MSin3; HDAC family (HDAC5); and other modulators such as: PC4; MBF1.

Another class of transcription modulators comprises enhancer-bound activators and sequence-specific or general repressors. Examples of these modulators include: non-tissue specific bHLHs, such as: USF; AP4; E-proteins (E2A/E12, E47; HEB/ME1; HEB2/ME2/MITF-2A,B,C/SEF-2/TFE/TF4/R8f); TFE family (TFE3, TFEB); the Myc, Max, Mad families; WBSCR14; and others.

Another example of this class of transcriptional modulators is the neuronally enriched bHLHs such as: Neurogenins (Neurogennin-1/MATH4c, Neurogenin-2/MATH4a, Neurogenin-3/MATH4b); NeuroD (NeuroD-1, NeuroD-2, NeuroD-3(6)/my051/NEX1/MATH2/Dx-3, NeuroD4/ATH-3/NeuroM); ATHs (ATH-1/MATH1, ATH-5/MATH5); ASHs (ASH-1/MASH1, ASH-2/MASH2, ASCL-3/reserved); NSCLs NSCL1/HEN1, NSCL2/HEN2), HANDs (Hand1/eHAND/Thing-1, Hand2/dHAND/Thing-2); Mesencephalon-Olfactory Neuronal bHLHs: COE proteins (COE1; COE2/Olf-1/EBF-LIKE3, COE3/Olf-1 Homo1/Mmot1); and others.

Other examples of this class of trnscriptional modulators includes: the Glia enriched bHLHs, such as: OLIG proteins (Olig1, Olig2/protein kinase C-binding protein RACK17, Olig3), and others; the bHLH family of negative regulators, which include: Ids (Id1, Id2, Id3, Id4), DIP1, HES (HES1, HES2, HES3, HES4, HES5, HES6, HES7, SHARPs (SHARP1/DEC-2/eip1/Stral3, SHARP2/DEC-1/TR00067497_p), Hey/HRT proteins (Hey1/HRT1/HERP-2/HESR-2, Hey2/HRT2/HERP-1, HRT3), and others. There are other bHLHs that fall within this present category of transcription modulators, which include: Lyl family (Lyl-1, Lyl-2); RGS family (RGS1, RGSRGS2/G0S8, RGS3/RGP3); capsulin; CENP-B; Mist1; Nhlh1; MOP3; Scleraxis; TCF15; bA305P22.3; Ipf-1/Pdx-1/Idx-1/Stf-1/Iuf-1/Gsf; and others.

Transcription factors belonging to Wnt pathway are also transcription modulators of the present class. Examples of such proteins include: β-catenin; GSK3; Groucho proteins (Groucho-1, Groucho-2, Groucho-3, Groucho-3); TCF family (TCF1A, B, C, D, E, F, G/LEF-1; TCF3; TCF4) and others.

Transcription factors belonging to Notch pathway are also transcription modulators of the present class. Examples of such proteins include: Delta, Serrate, and Jagged families (Dll1, Dll3, Dll4, Jagged1, Jagged2, Serrate2); Notch family (Notch1, Notch2, Notch3, Notch4, TAN-1); Bearded family (E(sp1)mα, E(sp1)m2, E(sp1)m4, E(sp1)m6); Fringe family (Mfng, Rfng, Lfng); Deltex/dx-1; MAML1; RBP-Jk/CBF1/Su(H)/KBF2; RUNX; and others.

Transcription factors belonging to TGFβ/BMP pathway are also transcription modulators of the present class. Examples of such proteins include: Chordin; Noggin; Follistatin; SMAD proteins (SMAD1, SMAD2, SMAD3, SMAD4, SAMD5, SMAD6, SMAD7, SMAD8, SMAD9, SMAD10); and others.

Transcription factors belonging to Sonic hedgehog pathway are also transcription modulators of the present class. Examples of such proteins include: SHH; IHH; Su(fu); GLI family (GLI/GLI1, Gli2, Gli3); Zic family (Zic/Zic1, Zic2, Zic3); and others.

Wing helix/forkhead family of transcription factors are also transcription modulators of the present class. Examples of such proteins include: BF proteins (BF1, BF2); and others.

HMG transcription factors are also transcription modulators of the present class. Examples of such proteins include: Sox proteins (Sox1, Sox2, Sox3, Sox4, Sox6, Sox10, Sox11, Sox13, Sox14 Sox18, Sox21, Sox22, Sox30); HMGIX; HMGIC; HMGIC; HMG-17; and others.

Homeodomain transcription factors pathway are also transcription modulators of the present class. Examples of such proteins include: Hox proteins; Evx family (Evx1, Evx2); Mox family (Mox1, Mox2); NKL family (NK1, NK3, Nkx3.1, NK4); Lbx family (Lbx1, Lbx2); Tlx family (Tlx1, Tlx2, Tlx3); Emx/Ems family (Emx1, Emx2); Vax family (Vax1, Vax2); Hmx family (Hmx1, Hmx2, Hmx3); NK6 family (Nkx6.1); Msx/Msh family (Msx-1, Msx-2); Cdx (Cdx1, Cdx2); Xlox family (Lox3); Gsx family (Goosecoid, GSX, GSCL); En family (En-1, En-2) HB9 family (Hb9/HLXB9); Gbx family (Gbx1,Gbx2), Dbx family (Dbx-1, Dbx-2); Dll family (Dlx-1, Dlx-2, Dlx-4, Dlx-5, Dlx-7); Iroquois family (Xiro1, Irx2, Irx3, Irx4, Irx5, Irx6); Nkx (Nkx2.1/TTF-1, Nkx2.2/TTF-2, Nkx2.8, Nkx2.9, Nkx5.1, Nkx5.2); PBC family (Pbx1a, Pbx1b, Pbx2, Pbx3); Prd family (Otx-1, Otx-2, Phox2a, Phox2B); Ptx family (Pitx2, Pitx3/Ptx3), XANF family (Hesx1/XANF-1); BarH family (BarH, Brx2); Cut; Gtx; and others.

POU domain factors are also transcription modulators of the present class. Examples of such proteins include: Brn2/XlPou2; Brn3a, Brn3b; Brm4/POU3F4; Brn5/Pou6F 1; and others.

Transcription factors with homeodomain and LIM regions are also transcription modulators of the present class. Examples of such proteins include: Isl1; Lhx2; Lhx3; Lhx4; Lhx5; Lhx6; Lhx7 Lhx9; LMO family (LMO1, LMO2, LMO4); and others.

Paired box transcription factors are also transcription modulators of the present class. Examples of such proteins include: Pax2; Pax3; Pax5; Pax6; Pax7; Pax8; and others.

Fork head/winged helix transcription factors are also transcription modulators of the present class. Examples of such proteins include: BF-1; BF-2/Freac4; Fkh5/Foxb1/HFH-e5.1/Mf3; Fkh6/Freac7; and others.

Zinc finger transcription factors are also transcription modulators of the present class. Examples of such proteins include: GATA family (Gata1, Gata2, Gata3, Gata4/5, Gata6); MyT family (MyT1, MyT11, MyT2, MyT3); SAL family (HSal1, Sal1, Sal3); REST/NRSF/XBR; Snail family (Scratch/Scrt); Zf289; FLJ22251; MOZ; ZFP-38/RU49; Pzf; Mtsh1/teashirt; MTG8/CBF1A-homolog; TIS11D/BRF2/ERF2; TTF-I interacting peptide 21; Znf-HX; Zhx1; KOX1/NGO-St-66; ZFP-15/ZN-15; ZnF20; ZFP200; ZNF/282; HUB1; Finb/RREB1; Nuclear Receptors (liganded: ER family; TR family; RAR family; RXR family; PML-RAR family; PML-RXR family; orphan receptors: Not1/Nurr; ROR; COUP-TF family (COUP-TF1, COUP-TF2)) and others.

RING finger transcription factors are also transcription modulators of the present class. Examples of such proteins include: KIAA0708; Bfp/ZNF179; BRAP2; KIAA0675; LUN; NSPc1; Neuralized family (neu/Neur-1, Neur-2, Neur-3, Neur-4); RING1A; SSA1/RO52; ZNF173; PIAS family (PIAS-α, PIAS-β, PIAS-γ, PIAS-γ homolog); parkin family; ZNF127 family and others.

Another class of transcription modulators includes proteins relating to cell-cycle progression-dedicated components that are part of the RNA polymerase II transcription complex. Examples of these proteins include: E2F family (E2F-1, E2F-3, E2F-4, E2F-5); DP family (DP-1, DP-2); p53 family (p53, p63; p73); mdm2; ATM; RB family (RB, p107, p130).

Still another class of transcription modulators includes proteins relating to capping, splicing, and polyadenylation factors that are also a part of the RNA polymerase II modulating activity. Factors involved in splicing include: Hu family (HuA, HuB, HuC, HuD); Musashi1; Nova family (Nova1, Nova2); SR proteins (B1C8, B4A11, ASF SRp20, SRp30, SRp40, SRp55, SRp75, SRm160, SRm300); CC1.3/CC1.4; Def-3/RBM6; SIAHBP/PUF60; Sip1; C1QBP/GC1Q-R/HABP1/P32; Staufen; TRIP; Zfr; and others. Polyadenylation factors include: CPSF; Inducible poly(A)-Binding Protein (U33818), and others.

Each of the factors discussed above is controlled by positive and negative regulatory mechanisms to achieve coordinated expression of genes associated with the same physiological process (differentiation, for example.) Uncontrollable proliferation of dedifferentiated mature cells or stem and progenitor cells leads to tumor development because many elements in the network of cellular transcriptional modulators that should be coordinately controlled are missing (not expressed or not expressed at sufficient quantities), or are inactive (additional complex components not available or improperly expressed). Given that the activity and developmental potential of every cell is characterized by the network of transcription modulatory factors, cells have only a limited capacity to respond to certain external stimuli and treatment protocols. Each of these systems can be used to characterize and identify neoplasms.

Immunological and Molecular Characterization of Subject's Response to Neoplasm

A variety of assay systems can be used to characterize and identify the presence and type of neoplastic cells in a subject. These techniques have utility in neoplasm characterization as they target particular molecular components of the tumor cell or by examining changes in a subject in response to the presence of a neoplasm. For example, well-known immunological assays can be used to identify the presence of antigenic markers that indicate the presence of a neoplasm. Similarly, molecular biology-based assays can be used to measure and compare the expression levels of particular genes that have expression patterns identified as differing between normal and neoplastic cells.

Immunological Characterization

The immunogenic properties of neoplastic molecular markers can be exploited to identify a neoplastic disease. Components of the immune response elicited from a host with a neoplasm can be used to characterize the nature of that neoplasm or the neoplastic cell. Phenotypic changes in neoplastic cell's gene expression patterns can elicit a measurable immune response from the host organism harboring the neoplastic cell. This immune response can be used to more accurately identify and characterize a neoplasm, which in turn is used to define the most effective strategy for the treatment of the neoplasm.

Immune responses are generally classified as being cellular or humoral in nature. A cellular immune response is characterized by the activation and deployment of various immune system cell types such as NK cells, T cells, lymphocytes, macrophages, and the like. A humoral immune response relates to small molecules such as cytokines, complement proteins, antibodies, and the like. Quantifiable elements of both the cellular and humoral immune responses can be exploited to characterize neoplasms.

Any sample source from a subject can be used to analyze an immune response of a host to a neoplastic disease. Examples of sample sources include blood, tears, semen, saliva, urine, or other bodily fluids.

Detection of neoplastic molecular markers present in a subject is currently used as a diagnostic for the presence of a malignancy or neoplasm in the body of a host. For example, the immunological detection of dopamine derivatives in the urine is presently used as a diagnostic for neoplasmic afflictions such as pheochromocytoma or neuroblastoma.

Using various immunological assay techniques, most human tumors have been reported to have new antigens that are foreign to the host and correlated to the neoplasm. For example, human tumors that have been shown to be antigenic include melanoma, neuroblastoma, astrocytoma, uroepithelial carcinoma, ovarian carcinoma, sarcoma, and colon carcinoma.

Existing assays are valuable but often limited diagnostic tools. One limitation of the existing technology arises from the fact that the markers used in these assays are often too general and not tumor specific. Because they lack specificity, current neoplastic markers do not provide the means by which a diagnostician can identify and characterize the presence of a neoplasm with precision.

The methods provided herein allow for the identification and characterization of neoplastic cells by exploiting tumor associated antigens (TAAs), their gene and protein expression patterns as well as tumor associated antibodies (TABs). Differentiating between normal and neoplastic cells using a TAA target is possible by exploiting qualitative and quantitative differences in gene expression of the target marker between the two cell types. Differentiating between normal and subjects with neoplastic disease using a TAB target is possible by exploiting qualitative and quantitative differences in the auto-immune response (presense of auto-antibodies against/specific to or recognizing the target marker protein) between the two blood samples.

It will be appreciated that TAAs and TABs can literally mean antigens or auto-antibodies, respectively, specific to a particular tumor or neoplastic disease. Alternatively, TAAs can refer to an altered expression pattern of a normal cell protein in a neoplastic cell. Alternatively, TABs can refer to an altered immune-response of a normal host compared with a subject with a neoplastic disease.

Transcription Factor-Derived Peptides for Identification of TABs

A tumor-associated antibody (TAB) profile of a patient with a tumor or neoplasm can be used to determine the molecular subtype of the tumor. The term "TAB" is used throughout the specification to refer to an immune response generated by a host in response to a tumor or neoplasm. This term encompasses other modalities of an immune response, such as the generation of cellular components with specificity to the TAB of a subject's tumor.

A subject's TAB profile is assembled by identifying tumor specific antibodies or other immune system components that are produced by the subject in response to the presence of a tumor. In a preferred embodiment, antibodies that a subject generates against a tumor are used to produce a TAB profile.

Screening for host antibodies (TABs) that bind to specific tumor markers or TAAs can be performed using any of a variety of well-known immunological techniques. For example, peptides or full-length proteins of potential TAAs can be bound to microtiter plates or membranes (dot or slot blot). For example, enzyme-linked immunoadsorbant assay (ELISA) can be used to determine the TAB profile of a patient.

Using a standard ELISA protocol, microtiter plates are incubated with a patients' serum samples followed by several washes. To identify human TABs that have bound to peptides or proteins, the microtiter plates are incubated with antihuman Ig antibodies conjugated to a reporter such as alkaline phosphatase or peroxidase. It will be appreciated that the antihuman antibodies are be conjugated to a radioisotope or fluorescent day to provide visualization of binding. The presence of human antibodies is visualized using color reaction for alkaline phosphatase or peroxidase.

Suitable peptides corresponding to transcriptional regulators employed to identify tumor specific or tumor enriched antibodies in a patient's blood are detailed in Tables 1-8.

TABLE 1

| Helix-loop-helix transcription factors | |
| --- | --- |
| Neurogenin family | |
| Neurogenin 1 | QDDEQERRRRRGRTR (SEQ ID NO:1) |
| Neurogenin 2 | CKRRPSRSRAVSR (SEQ ID NO:2) |
| Neurogenin 3 | QRRSRRKKANDRER (SEQ ID NO:3) |

TABLE 1-continued
Helix-loop-helix transcription factors

NeuroD family

| | |
|---|---|
| NeuroD 1 | DDDQKPKRRGPKKKM (SEQ ID NO:4) |
| NeuroD 2 | QDSSPDHEKSYH (SEQ ID NO:5) |
| NeuroD 3 | GTLDNSKSMKP (SEQ ID NO:6) |

ATH family

| | |
|---|---|
| ATH1 | SFNNDKKLSKYET (SEQ ID NO:7) |
| ATH5 | GLRCEQRGRDHPY (SEQ ID NO:8) |

ASH family

| | |
|---|---|
| ASH-1 | ADGQPSGGGHKSA (SEQ ID NO:9) |

NSCL family

| | |
|---|---|
| NSCL 1 | PTHSETESGFSDCGGGA (SEQ ID NO:10) |
| NSCL 2 | AADSDHPSSAHSDPES (SEQ ID NO:11) |

HES

| | |
|---|---|
| HES 1 | TPDKIPKTASEH (SEQ ID NO:12) |
| HES 2 | SLKPLLEKRRRAR (SEQ ID NO:13) |
| HES 3 | RREGSTTDSANP (SEQ ID NO:14) |
| HES 5 | SLHQDYSEGYSWC (SEQ ID NO:15) |

SHARP-family

| | |
|---|---|
| SHARP 1 | CKPKRSLKRDDTKDT (SEQ ID NO:16) |
| SHARP 2 | VYKSRRGIKRSEDSKE (SEQ ID NO:17) |

Hey/HRT-family

| | |
|---|---|
| Hey 1 | TASPTEPHHQGRLG (SEQ ID NO:18) |
| Hey 2 | SPQQTSSGTNNKPYRPW (SEQ ID NO:19) |
| Hey L | STPSSSQMQARKKR (SEQ ID NO:20) |

TABLE 2
Homeodomain transcription factors

BarH family

| | |
|---|---|
| BarH2 | TWYQNRRTKWKR (SEQ ID NO:21) |

Bcd family

| | |
|---|---|
| Ptx3/PITX3 | FKNRRAKWRKRERSQ (SEQ ID NO:22) |

Dll family

| | |
|---|---|
| Dlx1 | AGHSQPDGAYSSA (SEQ ID NO:23) |

TABLE 2-continued
Homeodomain transcription factors

| | |
|---|---|
| Dlx2 | HQHQQPPSGGGAGPGG (SEQ ID NO:24) |
| Dlx5 | HPSQESPTLPESSATDS (SEQ ID NO:25) |

Ems family

| | |
|---|---|
| Emx-2 | GSDSQQKKKGTHH (SEQ ID NO:26) |

En family

| | |
|---|---|
| En-1 | PRTRKLKKKKNEK (SEQ ID NO:27) |
| En-2 | APGNHQHPHRITNF (SEQ ID NO:28) |

Gbx family

| | |
|---|---|
| Gbx2 | STRRRQRPASSRRSRC (SEQ ID NO:29) |

Iroquois (Irx) family

| | |
|---|---|
| Irx2a | GGNEGSPCPPCPG (SEQ ID NO:30) |

NK-2 family

| | |
|---|---|
| Nkx-2.2 | PPQDSSSKSPEPS (SEQ ID NO:31) |
| Nkx-2.9 | QDAKPRVRREQQTCV (SEQ ID NO:32) |
| Nkx-5.1 | DERPAHKDGPTEAS (SEQ ID NO:33) |
| Nkx-5.2 | PHGPKEPSPKHHT (SEQ ID NO:34) |

Prd family

| | |
|---|---|
| Phox2a | CSSEDDDSKESTCSPT (SEQ ID NO:35) |
| Phox2b | GSSGKKSDSSRDDES (SEQ ID NO:36) |

TABLE 3
POU domain transcription factors

Brn-5 family

| | |
|---|---|
| Brn-5 | KPSTPESPAKSE (SEQ ID NO:37) |

TABLE 4
LIM region containing transcription factors

| | |
|---|---|
| Isl-1 | LRPHVHKQPEKTTR (SEQ ID NO:38) |
| Lhx2 | RDQPYPSSQKTKRMRT (SEQ ID NO:39) |
| Lhx3 | CFSRGESVYCKDDFF (SEQ ID NO:40) |
| Lhx4 | EDYETAKQNDDSEAGAK (SEQ ID NO:41) |
| Lhx5 | PLQDDPKETDNSTSSDK (SEQ ID NO:42) |

TABLE 4-continued

| LIM region containing transcription factors | |
|---|---|
| LMO4 | CSTCRNRLVPGDR (SEQ ID NO:43) |

TABLE 5

| Fork head/winged helix transcription factors | |
|---|---|
| BF-2 | DNGSFLRRRKRFKRQ (SEQ ID NO:44) |

TABLE 6

| High mobility group transcription factors | |
|---|---|
| Sox-family | |
| Sox-1 | SEPSGSPPAPAHSRA (SEQ ID NO:45) |
| Sox-2 | GNQKNSPDRVKR (SEQ ID NO:46) |
| Sox-3 | QPPSMSSPPPPPA (SEQ ID NO:47) |
| Sox-10 | KKDHPDYKYQPRRRKNG (SEQ ID NO:48) |
| Sox-11 | DYPDYKYRPRKKPK (SEQ ID NO:49) |

TABLE 7

| Zinc finger transcription factors | |
|---|---|
| Cys4 zinc finger of nuclear receptor type-family | |
| NOT1 | ASQSYSYHSSGEYS (SEQ ID NO:50) |
| Cys2His2 zinc finger domain-family | |
| SALL1 | DGDTEKGQPSRPTKSKD (SEQ ID NO:51) |
| SAL2 | PDSLDQPQPMEQGS (SEQ ID NO:52) |
| SALL3 | GYADSPSATPASRSPQR (SEQ ID NO:53) |
| Zic1 | SPSTDNPTTSSLSP (SEQ ID NO:54) |
| Zic3 | NSKDTTKTPSA (SEQ ID NO:55) |

TABLE 8

| Not-assigned transcription factors | |
|---|---|
| RBP-Jk | KPSQKKQSLKNTD (SEQ ID NO:56) |
| TLE1/Groucho 1 | DDKKHHDAEHHRDREPGT (SEQ ID NO:57) |
| TLE2/Groucho 2 | KEPSGPYESDEDKSDY (SEQ ID NO:58) |
| TLE3/Groucho 3 | STPSSKTKDLGHNDKSS (SEQ ID NO:59) |
| TLE4/Groucho 4 | DYSSESKKQKTEEK (SEQ ID NO:60) |

Molecular Biology Methods-Based Characterization of Neoplasms Molecular Characterization of Subject's Response to Neoplasm In addition to the immunological methods discussed above, neoplasms can be characterized using molecular biology-based tools directed toward monitoring transcription factors and other TAAs expression patterns. Standard molecular biological techniques are employed for such characterization. For guidance regarding such techniques see, for example, Sambrook et al., 1989, *Molecular Cloning, A Laboratory Manual*, Cold Springs Harbor Press, N.Y.; and Ausubel et al., 1989, *Current Protocols in Molecular Biology*, Green Publishing Associates and Wiley Interscience, N.Y. Examples of suitable assays include: Northern blot analysis, Southern blot analysis, Western blot analysis, RT-PCR, PCR, nucleic acid sequence based amplification assays (NASBA), and transcription mediated amplification (TMA).

As with the immunological methods discussed above, any sample source from a subject can be used to analyze molecular changes in a subject in response to the presence of a neoplasm. Examples of sample sources include neoplastic cells in blood, tears, semen, saliva, urine, or other bodily fluids.

Detection of neoplastic molecular markers present in a subject is currently used as a diagnostic for the presence of a malignancy or neoplasm in the body of a host. For example, detection of cells with neoplastic molecular markers in the urine (using single-cell PCR method) is presently used as a diagnostic for neoplasmic afflictions such as prostate carcinoma. Cell surface marker and transcription factor expression patterns are two preferred targets for molecular identification and characterization.

A list of primer sequences that can be used to probe samples for the presence of particular neoplastic markers is provided below.

TABLE 9

| Primer Sequences | | | | |
|---|---|---|---|---|
| Gene Name | GenBank ID | Oligo name | 5'-3' | |
| Ash-1 | L08424 | N s II 24 | gagcgcagccttagtaggagagga | (SEQ ID NO:61) |
| | U77616 | s 24 | ccctctctgttcctgcacccaagt | (SEQ ID NO:62) |
| | | E s 28 | ccagcATGgaaagctctgccaagatgg | (SEQ ID NO:63) |
| | | N as II 25 | gacttgcttgggcgctgacttgtga | (SEQ ID NO:64) |

TABLE 9-continued

Primer Sequences

| Gene Name | GenBank ID | Oligo name | 5'-3' | |
|---|---|---|---|---|
| | | N int as 26 | gagcgcagtgtctccaccttactcat | (SEQ ID NO:65) |
| | | as 26 (Stop) | ccagttggtgaagtcgagaagctcct | (SEQ ID NO:66) |
| Ath-1 | U61148 | s N 25 | ctccattggctgagaagacacgcga | (SEQ ID NO:67) |
| | | s 26 | gcgtccgagcctttgcagtgcaATGt | (SEQ ID NO:68) |
| | | as 25 (Stop) | ctccttcCTAacttgcctcatccga | (SEQ ID NO:69) |
| | | N int as 24 | gtagcagctcggacaaggcgttga | (SEQ ID NO:70) |
| Ath-5 | | s E 28 | ccaccatgaagtcggcctgcaaaccca | (SEQ ID NO:71) |
| | | as E 24 | catggggaagggctccggctggaa | (SEQ ID NO:72) |
| BarH | | s E 27 | ccaccatgtagaaatgacagcaatgga | (SEQ ID NO:73) |
| | | as II E 23 | gatggggttggacaaagggttga | (SEQ ID NO:74) |
| BarH-2 | | s 24 | catgatcgacgagatcctctccaa | (SEQ ID NO:75) |
| | | int as 25 | ggttccgaagagggtattggcaact | (SEQ ID NO:76) |
| BF-2 | | s E 27 | gcgctatgaccctgagcacggagatgt | (SEQ ID NO:77) |
| | | as E 25 | ggcgcgctaacgacgttcctaacaa | (SEQ ID NO:78) |
| BMP-2 | M22489 | s 24 | cggtccttgcgccaggtcctttga | (SEQ ID NO:79) |
| | | as 26 | gtactagcgacacccacaaccctcca | (SEQ ID NO:80) |
| BMP-6 | M60315 | s 24 | cgacgcggacatggtcatgagctt | (SEQ ID NO:81) |
| | | as 25 (Stop) | ccccagcatctggtttcgagTTAgt | (SEQ ID NO:82) |
| Brain-2 | | s 24 | cgagagtcatggcgaccgcagcgt | (SEQ ID NO:83) |
| | | as 24 | ccgtgaagctgggctgcgagtaga | (SEQ ID NO:84) |
| Brain-4/ XiPOU2 | X82324 | s 23 | accATGgccacagctgcctcgaa | (SEQ ID NO:85) |
| | | int as 25 | cggagtgatcctggcaatggtgcga | (SEQ ID NO:86) |
| | | as 22 (Stop) | cctcgcttcctccagtcagaga | (SEQ ID NO:87) |
| Brain-5/ Pou6F1 | NM_002702 | s 24 (ATG) | cattaccagcgccattcccagcAT | (SEQ ID NO:88) |
| | | as 24 | cggtcgtagttgagctccttagca | (SEQ ID NO:89) |
| Cdx-4 | AF003530 | s 25 | gagcgtgtatcctgggccgtctagt | (SEQ ID NO:90) |
| | | as 26 | cagagtcactttgcsccgagcctcca | (SEQ ID NO:91) |
| Chordin | AF076612 | s 24 | gaccttcagtgccatcctgactct | (SEQ ID NO:92) |
| | | as 24 | gtgcaggtgacagtgggtatccaa | (SEQ ID NO:93) |
| Cux-2 | AB006631 | s 24 | ggcagcatccaaggcagatgaagt | (SEQ ID NO:94) |
| | | as 24 | ctccttgcccttcaccgtgagctt | (SEQ ID NO:95) |
| Dlx-1 | | s E 28 | ggagatgaccatgaccaccatgccaga | (SEQ ID NO:96) |
| | | as E 24 | cacatcagttgaggctgctgcata | (SEQ ID NO:97) |
| Dlx-2 | U51003 | s 26 | gtggctgatatgcactcgacccagat | (SEQ ID NO:98) |
| | | as 27 | cttggaccggcggttctggaaccagat | (SEQ ID NO:99) |
| Dlx-5 | | s E 31 | ccgccatgacaggagtgtttgacagaagggt | (SEQ ID NO:100) |
| | | as E 23 | ctaatagagtgtcccggaggcca | (SEQ ID NO:101) |
| Dlx-7 | AF028235 | s 26 | cagcacctaaaccagcgtttccagca | (SEQ ID NO:102) |
| | | as 25 | catcatctgaggcgaagccaggaca | (SEQ ID NO:103) |
| Emx-1 | AA775410 (5') X68879 (3') | s 24 as 24 | cgtgttccccgaggccatgaacca gatgtcctcccattggcctgctt | (SEQ ID NO:104) (SEQ ID NO:105) |
| Emx-2 | X68880 | s 25 | cacacccctattcgcctcgcagca | (SEQ ID NO:106) |
| | | as 28 | ctatttcctccggactcgcctgcttggt | (SEQ ID NO:107) |
| En-1 | | s E 25 | cgagcatggaagaacagcagccga | (SEQ ID NO:108) |
| | | as E 25 | ggctactcgctctcgtcttttgtcct | (SEQ ID NO:109) |
| En-2 | | s E 25 | ccagcatggaggagaatgaccccaa | (SEQ ID NO:110) |
| | | as E 24 | cctactcgctgtccgacttgccct | (SEQ ID NO:111) |
| GATA-1 | X17254 | N s 24 | gggatcacactgagcttgccacat | (SEQ ID NO:112) |
| | | s 25 (ATG) | cccaggttaatcccagaggctccA | (SEQ ID NO:113) |
| | | as 26 (Stop) | CAtgagctgagcggagccaccacagt | (SEQ ID NO:114) |

TABLE 9-continued

Primer Sequences

| Gene Name | GenBank ID | Oligo name | 5'-3' | |
|---|---|---|---|---|
| GATA-2 | M68891 | s 24 | caatcacctcgactcgcagggcaa | (SEQ ID NO:115) |
| | | as 26 | gaggccacaggcattgcacaggtagt | (SEQ ID NO:116) |
| GATA-3 | | s 24 | gagcacagccgaggccatggaggt | (SEQ ID NO:117) |
| | | as 24 | ccttgggcctggacttgcatccga | (SEQ ID NO:118) |
| Gbx-2 | U31468 | s E 26 (ATG) | ctggcctctaccgagcgcgtctATGa | (SEQ ID NO:129) |
| | NM_001485 | s 25 | ggagtagcaccgccttcagcataga | (SEQ ID NO:120) |
| | | as 24 | gattgtcatccgagctgtagtcca | (SEQ ID NO:121) |
| | | as E 23 (Stop) | gccctggcccttctggaccccTCA | (SEQ ID NO:122) |
| Geminin | AF067855 | s 23 (ATG) | ccatctacataATGaatcccagt | (SEQ ID NO:123) |
| | | as 22 (Stop) | gtggaggtaaacttcggcagta | (SEQ ID NO:124) |
| GLI-1 | X07384 | s 24 | gaccaagaagcgggcactgtccat | (SEQ ID NO:125) |
| | | as 26 | gcgtgagtatgacttccggcaccctt | (SEQ ID NO:126) |
| GLI-2 | AB007298 | s 25 | ctcacctccatcaatgccacgccca | (SEQ ID NO:127) |
| | | as 24 | ccaccagcatgtactgcgccttga | (SEQ ID NO:128) |
| GLI-3 | M57609 | s 25 | gcagctcttcagcaagtggctccta | (SEQ ID NO:129) |
| | | as 24 | ctctcttgagcagtccagccacct | (SEQ ID NO:130) |
| Glu Synthetase | | s 28 | ccaccatgaccacctcagcaagttccca | (SEQ ID NO:131) |
| | | as 24 | cgatgtccctgccataggctctgt | (SEQ ID NO:132) |
| Groucho-1/ TLE1 | M99435 | s E 24 | ccgaaatgcagaggcactatgtga | (SEQ ID NO:133) |
| | | as E 24 | cggagaagaagggtcctcattaga | (SEQ ID NO:134) |
| Groucho-2 | | s E 25 | gcaggatgtaccccaggaaggca | (SEQ ID NO:135) |
| | | as E 25 | cctcagggcgacgctgtccgtggaa | (SEQ ID NO:136) |
| Groucho-3/ TLE3 | | s E 23 | ccaccatgtatccgcagggcaga | (SEQ ID NO:137) |
| | | as E 24 | cgctcatctgggtgggatgttgt | (SEQ ID NO:138) |
| Groucho-4 | | s E 24 | cagagatgcagcggcattatgtca | (SEQ ID NO:139) |
| | | as E 25 | gtactgccattgggtccttaggct | (SEQ ID NO:140) |
| Hes-1 | L19314 | s E 25 (ATG) | ggaaaATGccagctgatataatgga | (SEQ ID NO:141) |
| | | s 24 | ctaccccagccagtgtcaacacga | (SEQ ID NO:142) |
| | | as 26 (Stop) | gttccgccacggcctccacatggagt | (SEQ ID NO:143) |
| Hes-2 | 4914512 | s E 34 | ccaccatgaagagcctgaagccgctgctggagaa | (SEQ ID NO:144) |
| | | s 24 | gagcctgaagccgctgctggagaa | (SEQ ID NO:145) |
| | | as 24 | ccgctctccgccacaggtgctcca | (SEQ ID NO:146) |
| Hes-3 | | s E 24 | gcccaccgatctccaagcctctga | (SEQ ID NO:147) |
| | | as E 24 | ctacgtctcaccacggtcgccaca | (SEQ ID NO:148) |
| Hes-5 | | s 26 | gtggagatgctcagtcccaaggagaa | (SEQ ID NO:149) |
| | | as 26 | ccgctggaagtggtaaagcagcttca | (SEQ ID NO:150) |
| Hey-1/ HERP2 | HRT1/ NM_012258 | s E 30 (ATG) | ccagcATGaagcgagctcaccccgagtaca | (SEQ ID NO:151) |
| | | s 24 | ggacagcgagctggacgagaccat | (SEQ ID NO:152) |
| | | as 24 | ggctcagtgcattgggagacagta | (SEQ ID NO:153) |
| | | as E 25 (Stop) | ccctcccctcattctacatcagttct | (SEQ ID NO:154) |
| Hey-2/ HERP1 | HRT2/ NM_012259 | s E 26 (ATG) | gacctcgagagcgacATGgacgaga | (SEQ ID NO:155) |
| | | s 24 | ggctactttgacgcacacgctctt | (SEQ ID NO:156) |
| | | as 25 | cactgctggtctgctgaggactgga | (SEQ ID NO:157) |
| | | as E 25 | ccaacttctgtcccccagggtcggt | (SEQ ID NO:158) |
| HeyL | | s 23 | catgaagcgacccaaggagccga | (SEQ ID NO:159) |
| | | as 25 | cagctcagaaagcccccgatttcagt | (SEQ ID NO:160) |
| Id-3 | | s 23 | cggctgctacgaggcggtgtgct | (SEQ ID NO:161) |
| | | int as 23 | ggagtgagctcggctgtctggat | (SEQ ID NO:162) |
| Irx-2a | U90304 | N s 26 (ATG) | accggtcgttccgATGgcagtggaga | (SEQ ID NO:163) |
| | | int as 24 | cgtcgttcttctccaggtcaatgt | (SEQ ID NO:164) |
| | | as 23 (Stop) | cgcgTTAaatgtcggacataccct | (SEQ ID NO:165) |

TABLE 9-continued

Primer Sequences

| Gene Name | GenBank ID | Oligo name | 5'-3' | |
|---|---|---|---|---|
| Irx-3 | U90305 (5') AI217994 (3') | s 25 (ATG) as 25 (Stop) | cagccaccatgtccttcccacactt gaaCTAggatgaggagagagccgat | (SEQ ID NO:166) (SEQ ID NO:167) |
| Lhx-2 | | s E 24 as E 24 | ccgagatggaccgcagggccaaga gtggggtgaggggttgcgagtcat | (SEQ ID NO:168) (SEQ ID NO:169) |
| Lhx-3 | | s E 25 as E 27 | gaaccatggaggcgcgcgggagct gtcagaactgagcgtggtctacctcat | (SEQ ID NO:170) (SEQ ID NO:171) |
| Lhx-4 | | s E 28 as E 26 | gacgatgcaacagattccccagtgtgct gaggatggtccatctcatcgagccaa | (SEQ ID NO:172) (SEQ ID NO:173) |
| Lhx-5 | | s E 26 as E 24 | ggctatgatggtgcactgtgctggct cttaccatacggccgcttcgttga | (SEQ ID NO:174) (SEQ ID NO:175) |
| LMO-4 | | s 27 as 24 | catggtgaatccgggcagcagctcgca ccttctggtctggcagtagtggat | (SEQ ID NO:176) (SEQ ID NO:177) |
| Med-6 | AF074723 | s 24 (ATG) as 25 (Stop) | gggaacctgtaaacgctctcggaa caaagtgctgggattacaggcgtga | (SEQ ID NO:178) (SEQ ID NO:179) |
| MitfA | | s 25 as 25 | ccatgcagtccgaatcggggatcgt ccatctgcatacaggacgctcgtga | (SEQ ID NO:180) (SEQ ID NO:181) |
| Musashi-1 | NM_002442 | s 26 as 25 | caagatgttcatcggggggactcagtt gtacccattggtgaaggctgtggca | (SEQ ID NO:182) (SEQ ID NO:183) |
| Msx-1 | M97676 | E s 27 (ATG) as 21 (Stop) | gccATGagcttctttgccactcggtgt gacctgggaccctCTAtgtca | (SEQ ID NO:184) (SEQ ID NO:185) |
| Msx-2 | S75361 | E s 25 (ATG) as 24 (Stop) | accATGgcttctccgtccaaaggca gtcttccTTAggacaggtggtaca | (SEQ ID NO:186) (SEQ ID NO:187) |
| Myt-1 | | s 24 as 24 | ggaggtccgctcggatgatgacaa cacgaagcacatgggcctgaggat | (SEQ ID NO:188) (SEQ ID NO:189) |
| Myt-2 | | s 24 as 25 | ggacacggtgttgtgctctcagaa cagttacgtggccggttccatcaca | (SEQ ID NO:190) (SEQ ID NO:191) |
| Myt-3 | | s 26 as 26 | ggaaccgaggtgccaatggattcact gaagttggagccactgtcccagccat | (SEQ ID NO:192) (SEQ ID NO:193) |
| Nestin | X65964 | N s 26 N as 24 | ggcagcgttggaacagaggttgga ctctaaactggagtggtcagggct | (SEQ ID NO:194) (SEQ ID NO:195) |
| Neuralized-1 | | s 24 (ATG) s-517 23 s-1155 24 as-1185 23 as-1932 23 as-2135 24 as 25 (Stop) | ccaccatgggtaacaacttctccagt cccgtcacttctcaccgatgcca ctcggtgagcctatgcgacctcaa ggcacgttgaggtcgcataggct ctcgggcaggctcactggcaat ctaggagctgcggtaggtcttgat gctaggagctgcggtaggtcttgat | (SEQ ID NO:196) (SEQ ID NO:197) (SEQ ID NO:198) (SEQ ID NO:199) (SEQ ID NO:200) (SEQ ID NO:201) (SEQ ID NO:202) |
| NeuroD1/ Beta2 | D82347 | s 25 E s 27 (ATG) as 25 as E 25 (Stop) | gccccagggttatgagactatcact ccaacATGaccaaatcgtacgcgaga ccgacagagcccagatgtagttctt ggtgaaactggcgtgcctCTAatca | (SEQ ID NO:203) (SEQ ID NO:204) (SEQ ID NO:205) (SEQ ID NO:206) |
| NeuroD2 | AB021742 U58681 | s 28 (5'UTR) int as 24 as 23 (Stop) | gtagagatgccacactcgctccgcggtt cgatcttggacagcttctgcgtct cggcgcgaagtcTCAgttatgaa | (SEQ ID NO:207) (SEQ ID NO:208) (SEQ ID NO:209) |
| NeuroD3 | D81215 U69205 | s 26 (5'UTR) E s 28 (ATG) as 25 as 26 (Stop) | gactccaggagacgatgcgacactca ccgccATGttaacactaccgtttgatga caagcagcctgccaccaagtttgta gacaggggaggtgaatgaccactgtt | (SEQ ID NO:210) (SEQ ID NO:211) (SEQ ID NO:212) (SEQ ID NO:213) |
| Neurgenin-1 | U67777/ AC005738 U63842 | s 24 (5'UTR) s 26 (ATG) as 24 (Stop) | ccggcgacatcactcaggagacca ctgtccgtcggtcctgcacagcgcaa gtgtaaggaatgaaacagggcgt | (SEQ ID NO:214) (SEQ ID NO:215) (SEQ ID NO:216) |

TABLE 9-continued

Primer Sequences

| Gene Name | GenBank ID | Oligo name | 5'-3' | |
|---|---|---|---|---|
| Neurgenin-2 | | s E 26 | ccaggatgttcgtcaaatctgagact | (SEQ ID NO:217) |
| | | as E 25 | cagctctagatacagtccctggcga | (SEQ ID NO:218) |
| Neurogenin-3 | AJ133776 | s 26 (5'UTR) | cctcgctgctcatcgctctctattct | (SEQ ID NO:219) |
| | | E s 26 (ATG) | ccacgATGacgcctcaaccctcgggt | (SEQ ID NO:220) |
| | | int as 26 | ctgcttgctcagtgccaactcgctct | (SEQ ID NO:221) |
| | | as 26 (Stop) | cagcgacagacaggtccttTCAcaga | (SEQ ID NO:222) |
| | | E as 26 (Stop) | cagaaaatctgagaaagccagactgcct | (SEQ ID NO:223) |
| Nkx-2B | | s 25 | ggtctcgaaccatgtcgctgaccaa | (SEQ ID NO:224) |
| | | as 24 | gggctttgagcgcgtgacatggtt | (SEQ ID NO:225) |
| Nkx-2.5 | AB021133 | s 25 | cccacgcccttctcagtcaaagaca | (SEQ ID NO:226) |
| | | as 24 | cgacgccgaagttcacgaagttgt | (SEQ ID NO:227) |
| Nkx-2.8 | AF000296 | s 25 (5'UTR) | gctaatatcccggctgccagcgcat | (SEQ ID NO:228) |
| | | as 25 (Stop) | ctgcggccTCAccagttccaggaga | (SEQ ID NO:229) |
| Noggin | U31202 | s 23 (ATG) | gcATGgagcgctgccccagccta | (SEQ ID NO:230) |
| | | as 23 (Stop) | cccgagttCTAgcacgagcactt | (SEQ ID NO:231) |
| Nova-1 | NM_002515 | s 25 (ATG) | cagcggcaggaactgcaaacATGat | (SEQ ID NO:232) |
| | | as 25 | cagccttcacagtagcacctccctt | (SEQ ID NO:233) |
| Nova-2 | AF083898 | s 24 | ggaaccacagagcgggtatgccta | (SEQ ID NO:234) |
| | | as 25 | cagggagttggtgttgtagccgtaa | (SEQ ID NO:235) |
| | | as 25 (Stop) | ggtgacccgctgactgatgaggtat | (SEQ ID NO:236) |
| NSCL-1 | | s 25 | cagtgacttctagagctcagtggca | (SEQ ID NO:237) |
| | | as 25 | ccaggcgcagaatctcaatcttgga | (SEQ ID NO:238) |
| NSCL-2 | | s 24 | ccaagcatctccaagccactgact | (SEQ ID NO:239) |
| | | as 24 | ccaggacgtggttgagataggaga | (SEQ ID NO:240) |
| Oct-2 | XB1030 | s 25 | cagtgatctggaggagctggagcaa | (SEQ ID NO:241) |
| | | as 27 | ggcgatcagcaggatctcctctgaggt | (SEQ ID NO:242) |
| Olf-1 | | s 25 | cactttgagaagcagccgccttcca | (SEQ ID NO:243) |
| | | as 25 | ccctatgatgatgacagtcgcacct | (SEQ ID NO:244) |
| Olf-1 Homo1 | | s 25 | gcagcgggctgaacctgaaggagga | (SEQ ID NO:245) |
| | | as 24 | gggcgtctcattccggttgccaca | (SEQ ID NO:246) |
| Otx-1 | AI971638 | s 25 | ctagaggacgaggcagagctggaca | (SEQ ID NO:247) |
| | | as 25 | ccacccagctgttagcatgatgtct | (SEQ ID NO:248) |
| Otx-2 | AA334301 | s 25 | cagacatcttcatgcgagaggaggt | (SEQ ID NO:249) |
| | AA317337 | as 25 | gagatggctggtgactgcattggta | (SEQ ID NO:250) |
| Pax-6 | NM_000280 | s 25 (ATG) | ccagccagagccagcATGcagaaca | (SEQ ID NO:251) |
| | | as 26 | ggttggtagacactggtgctgaaact | (SEQ ID NO:252) |
| Pbx-1 | | s 24 | gtagcctttggagatggacgagca | (SEQ iD NO:253) |
| | | as 23 | ctgcatctggatggagctgaact | (SEQ ID NO:254) |
| Phox2a | AF022722 | s 23 (ATG) | ccgATGgactactcctacctcaa | (SEQ ID NO:255) |
| | AF022724 | int as 25 | cgtggactccttggaatcgtcgtct | (SEQ ID NO:256) |
| | | as 23 (Stop) | gagtggccctgacttggtctcca | (SEQ ID NO:257) |
| Phox2b | | s E 36 (ATG) | gcagtatggctgggatggacacctcgagcctggctt | (SEQ ID NO:258) |
| | AB015671 | s 24 (ATG) | ctccagccaccttctccatatcca | (SEQ ID NO:259) |
| | | int as 25 | gctctcgtcgtccctggaagagtca | (SEQ ID NO:260) |
| | | as 25 (Stop) | cgccgcaggattccagaTCAgaaca | (SEQ ID NO:261) |
| | | as E 24 (Stop) | gccgcaggattccagatcagaaca | (SEQ ID NO:262) |
| Phox 2b | | s E 24 | ccagtatggccgggatggatacct | (SEQ ID NO:263) |
| | | as E 25 | cgcagatcgcagatcagaacatact | (SEQ ID NO:264) |
| Pitx-3 | | s E 24 | ccaccatggagttcggcctgctca | (SEQ ID NO:265) |
| | | as E 27 | ccttttcacggcgtactggcacggact | (SEQ ID NO:266) |
| Ptx-3 (mouse) | | s E 26 | ggcatggagtttgggctgcttggtga | (SEQ ID NO:267) |
| | | as E 27 | cacggcgtactggcaggggctaaggtt | (SEQ ID NO:268) |

TABLE 9-continued

Primer Sequences

| Gene Name | GenBank ID | Oligo name | 5'-3' | |
|---|---|---|---|---|
| RBP-JK | | s E 25 | ggttacatgggactggacagcgcgt | (SEQ ID NO:269) |
| | | as E 24 | ctaagtctggatgaagaggtggaa | (SEQ ID NO:270) |
| REST/NRSF/ XBR | | s 25 II Fin. | gtgaccgctgcggctacaatactaa | (SEQ ID NO:27 1) |
| | | as 25 VIII Fin. | ggacaagtaggatgcttagatttga | (SEQ ID NO:272) |
| Sall1/ Spalt1 | Y18264 Y18265 | s E 23 (ATG) | ccagcATGtcgcggaggaagcaa | (SEQ ID NO:273) |
| | | s 25 | ggaggaagcaagcgaagcctcaaca | (SEQ ID NO:274) |
| | | int as 24 | cgagttgaggtagagaggttgtga | (SEQ ID NO:275) |
| Sal2/ Spalt2 | X98834 | s 24 | gaaagcagcggaaaccccaacagt | (SEQ ID NO:276) |
| | | s E 29 | ccaggatgacttcactaccaagctgggca | (SEQ ID NO:277) |
| | | int as 25 | gcagcacccgtagctcttccaagat | (SEQ ID NO:278) |
| | | as E 25 | ggctcatgggatcgtggggtcatct | (SEQ ID NO:279) |
| Sall3 | | s E 25 | cgatcatgaagcaccgcaagggcaa | (SEQ ID NO:280) |
| | | as E 24 | gaacttcttctggcagatggggca | (SEQ ID NO:281) |
| Sharp-1 | AW449776 (5') AI819798 (3') | s E 25 (ATG) | ggaacATGgacgaaggaattcctca | (SEQ ID NO:282) |
| | | as E 24 | caagtggttgatcagctggacaca | (SEQ ID NO:283) |
| Sharp-2/ Dec-1 | NM_003670 | s E 24 (ATG) | ctagtgcagacaggagcgcgcagt | (SEQ ID NO:284) |
| | | s 25 | gagcacggagacctaccagggatgt | (SEQ ID NO:285) |
| | | as 26 | cgtgaacctgcgtccgtggtcact | (SEQ ID NO:286) |
| | | as E 23 (Stop) | gcagcaggatcccctagagagtT | (SEQ ID NO:287) |
| SHH | | s 24 | aggatgctgctgctggcgagatgt | (SEQ ID NO:288) |
| | | as 27 | gccctgctccaggtgcaccgtggccga | (SEQ ID NO:289) |
| Six-3 | AF092047 | s 29 (ATG) | gccATGgtattccgctccccctagacct | (SEQ ID NO:290) |
| | | int as 23 | gcctggtgctggagcctgttctt | (SEQ ID NO:291) |
| | | as 29 (Stop) | ggCTAtcatacatcacattccgagtcgct | (SEQ ID NO:292) |
| SMAD-6 | AF035528 | s 29 (ATG) | cgtATGgttcaggtccaaacgctcggggct | (SEQ ID NO:293) |
| | | as 26 (Stop) | ccgccaCTAtctggggttgttgagga | (SEQ ID NO:294) |
| SMAD-7 | AF010193 | s 24 (ATG) | ccccgcATGttcaggaccaaacga | (SEQ ID NO:295) |
| | | as 24 (Stop) | cacgcggctaccggctgttgaaga | (SEQ ID NO:296) |
| Sox-1 | X13436 | s 26 (ATG) | cccgATGtacagcatgatgatggaga | (SEQ ID NO:297) |
| | | as 26 | gtacatgctgatcatctcgcgcaggt | (SEQ ID NO:298) |
| Sox-2 | | s 26 (ATG) | gccATGtacaacatgatggagacgga | (SEQ ID NO:299) |
| | | as 25 (Stop) | cctccagttcgctgtccggcccTCA | (SEQ ID NO:300) |
| Sox-3 | X71135 | s 25 (ATG) | caggcagactgtgaATGcgacctgt | (SEQ ID NO:301) |
| | | as 26 (Stop) | cTCAgatgtgggtcagcggcaccgtt | (SEQ ID NO:302) |
| Sox-10 | AJ001183 | s 25 | gtgggcgttggactctttgcgagga | (SEQ ID NO:303) |
| | | s E 25 (ATG) | gcgacATGgcggaggagcaggatct | (SEQ ID NO:304) |
| | | int as 26 | gctggtacttgtagtccgggtggtct | (SEQ ID NO:305) |
| | | as 24 (Stop) | cctTTAgggccgggacagtgtcgt | (SEQ ID NO:306) |
| | | as E 26 | cacgttgccgaagtcgatgtgaggct | (SEQ ID NO:307) |
| Sox-11 | | s 24 | ggatcatggtgcagcaggcggaga | (SEQ ID NO:308) |
| | | as 25 | ccagaaacacgcacttgaccgtctt | (SEQ ID NO:309) |
| Synemin | | s 25 | gcgattgactgcctggaggatgaga | (SEQ ID NO:310) |
| | | as 25 | cgaagcacctgctgccaccttgtct | (SEQ ID NO:311) |
| TAF135 | Y11354 | s-1 26 | ctggacgaggtcttcttcaacagcga | (SEQ ID NO:312) |
| | | s-2 25 | ggaatggtcctcgtccgaagtgaga | (SEQ ID NO:313) |
| | | as-1 25 | gcatagttggcccgatgaccatgct | (SEQ ID NO:314) |
| | | as-2 26 | gggtaagctcctcttcaggaaaggca | (SEQ ID NO:315) |
| | | as-3 24 | ggtaacacggcgggttttcaccaca | (SEQ ID NO:316) |
| | | as-4 25 | gcctgctcatatctgtcgtcatcct | (SEQ ID NO:317) |
| | | as-5 24 | gtagagcagcagtgaatggcttgt | (SEQ ID NO:318) |
| TBP | | s-1 25 | ggatcagaacaacagcctgccacct | (SEQ ID NO:319) |
| | | as-1 26 | gcggtacaatcccagaacttctccgaa | (SEQ ID NO:320) |
| | | as-2 26 | ggcacgaagtgcaatggtctttaggt | (SEQ iD NO:32 1) |
| | | as-3 26 | cgtggttcgtggctctcttatcctca | (SEQ ID NO:322) |
| | | as-4 27 | cttcacatcacagctccccaccatgtt | (SEQ ID NO:323) |
| | | as-5 26 | ggaggcaagggtacatgagagccatt | (SEQ ID NO:324) |

TABLE 9-continued

Primer Sequences

| Gene Name | GenBank ID | Oligo name | 5'-3' | |
|---|---|---|---|---|
| TRAP80/ CRSP77 | AF117657 | s-1 24 | ccagtctgagcgttgcgttcggtt | (SEQ ID NO:325) |
| | | s-2 24 | ggccttgggactcagtgaggaaca | (SEQ ID NO:326) |
| | | as-1 25 | cgtctgaggattctgttttggagga | (SEQ ID NO:327) |
| | | as-2 28 | ctcggaaagggctgagagataatctggt | (SEQ ID NO:328) |
| | | as-3 24 | cggcttgctaagctgtcaatggtt | (SEQ ID NO:329) |
| | | as-4 24 | gtagacaagggctaagtgcagaca | (SEQ ID NO:330) |
| TRAP170/ EXLM1/ CXORF4/ CRSP150 | AF135802 | s-1 25 | gtgttgacggacctactgccaagga | (SEQ ID NO:331) |
| | | s-2 24 | ggtatcatgctggaaagtgcctct | (SEQ ID NO:332) |
| | | s-3 24 | gccaagcgcaagttgtctgatgat | (SEQ ID NO:333) |
| | | s-4 26 | cgttctctaccagacatacctgctca | (SEQ ID NO:334) |
| | | s-5 24 | gcagccaggaacatcaggtgctta | (SEQ ID NO:335) |
| | | as-1 25 | gggagtgcagtctctatggaagagt | (SEQ ID NO:336) |
| | | as-2 26 | caccttccacttgcactccttgatgt | (SEQ ID NO:337) |
| | | as-3 25 | gtggacgactgtggcagaatggaga | (SEQ ID NO:338) |
| | | as-4 26 | ggtcaagagttccatgtggactagca | (SEQ ID NO:339) |
| | | as-5 26 | ctgctgtctgggaatgtctgcctgct | (SEQ ID NO:340) |
| Xanf-1/ Hesx1 | | s 25 (ATG) | ccacgagaggATGtctcccagcctt | (SEQ ID NO:341) |
| | | as 25 | cgataccaggatagcagtttactct | (SEQ ID NO:342) |
| Zic-1 | D76435 | s E 28 | ccacgatgctcctggacgccggccccca | (SEQ ID NO:343) |
| | | s 24 | cggagcagtacggccaggtgacca | (SEQ ID NO:344) |
| | | as 26 | gattcgcagggttctttcagtaatgt | (SEQ ID NO:345) |
| | | as E 26 (Stop) | gattcgcagggttctttcagtaatgt | (SEQ ID NO:346) |
| Zic-2 | AF104902 | s 24 | cgccgagatgcaggaccgtgaact | (SEQ ID NO:347) |
| | | as 24 | ggaggtgtggacgtgcatgtgctt | (SEQ ID NO:348) |
| Zic-3 | | s 23 (ATG) | gccATGacgatgctcctggacgg | (SEQ ID NO:349) |
| | | as 23 (Stop) | ccTCAgacgtaccattcgttaaa | (SEQ ID NO:350) |
| Ku p70/ p80 | | s E 24 | cggcaacatggtgcggtcggggaa | (SEQ ID NO:351) |
| | | as E 29 | ccaacatggtgcggtcggggaataaggca | (SEQ ID NO:352) |
| MRE11 | | s E 28 | ccaccatgagtactgcagatgcacttga | (SEQ ID NO:353) |
| | | as E 28 | cctgtatcttgcatgtttctcagggcca | (SEQ ID NO:354) |
| NBSI/ nibrin | | s E 19 | ccacgatgtggaaactgct | (SEQ ID NO:355) |
| | | as E 24 | gcctgaagtagatgcttactagga | (SEQ ID NO:356) |
| PCNA | | s E 25 | gttgttgccactccgccaccatgtt | (SEQ ID NO:357) |
| | | as E 26 | gcctaagatccttcttcatcctcgat | (SEQ ID NO:358) |
| PIR51 | | s E 30 | cgaccatggtgcggcctgtgagacataaga | (SEQ ID NO:359) |
| | | as E 24 | ccacactcaggtgctagtggcatt | (SEQ ID NO:360) |
| RAD51B | | s E 29 | ccagcatgggtagcaagaaactaaaacga | (SEQ ID NO:361) |
| | | as E 25 | ctgtctctaggaatttccataggct | (SEQ ID NO:362) |
| RAD52 | | s E 26 | gcaagatgtctgggactgaggaagca | (SEQ ID NO:363) |
| | | as E 26 | gtggcctgagcctcagtaagatggat | (SEQ ID NO:364) |
| RAD54B | | N s E 25 | ggcgcgctaacgacgttcctaacaa | (SEQ ID NO:365) |
| | | as E 26 | cactatgtgccagtagcttgagtggt | (SEQ ID NO:366) |
| RFC 40 kD | | s E 26 | cgagaatggaggtggaggccgtctgt | (SEQ ID NO:367) |
| | | as E 24 | gtcagtcagtgaagtctctgctct | (SEQ ID NO:368) |
| RFC 140 kD | | s E 28 | ccacgatggtgccctccagcccagcggt | (SEQ ID NO:369) |
| | | as E 24 | gcccgagagtcactggttcacatt | (SEQ ID NO:370) |
| RPA 14 kD | | s E 30 | ccagcatggtggacatgatggacttgccca | (SEQ ID NO:371) |
| | | as E 24 | gatcaatcatgttgcacaatccct | (SEQ ID NO:372) |
| RPABCA | | s E 27 | cgaccatggagggaggcttgaagagga | (SEQ ID NO:373) |
| | | as E 26 | ccctctatcacagttttaggacccca | (SEQ ID NO:374) |
| XRCC2 | | s E 24 | ccgcgatgtgtagtgccttccata | (SEQ ID NO:375) |
| | | as E 24 | gcgtagtaccctgcaaaagactat | (SEQ ID NO:376) |
| XRCC3 | | s E 30 | gcaccatggatttggatctactggacctga | (SEQ ID NO:377) |
| | | as E 27 | gtgttgtgcagccgccaccgtgtcagt | (SEQ ID NO:378) |

TABLE 9-continued

Primer Sequences

| Gene Name | GenBank ID | Oligo name | 5'-3' | |
|---|---|---|---|---|
| XRCC4 | | s E 26 | ccaccatggagagaaaaataagcaga | (SEQ ID NO:379) |
| | | as E 27 | ctcatcaaagaggtcttctgggctgct | (SEQ ID NO:380) |

Methods of Diagnosis and Treatment

Development of tumor classifications based on the neoplastic molecular marker expression patterns has an important heuristic value. It allows practitioners to identify the molecular profile of a subject's tumor cell and diagnose the type of cancer with which the subject is afflicted.

Accordingly, in some embodiments, the disclosed methods are useful for diagnosing the existence of a neoplasm or tumor of any origin. For example, the tumor may be associated with carcinoma, astrocytoma, sarcoma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer. In preferred embodiments, the tumor is a neural cell tumor, lung tumor or prostate tumor.

Early and effective diagnosis of various tumor types would be a great boon to the treatment of various neoplastic diseases. Such identification capabilities would permit practitioners to fashion highly specific cancer treatments based upon the identification of the individual tumor type.

Development of a Database

The diagnosis and ultimate treatment of neoplastic disease based upon molecular markers produced directly or indirectly from a neoplastic cells is facilitated by the development and utilization of a database correlating neoplastic molecular characteristics (TAA or TAB profiles) with specific tumor sub-types. Based upon the classification of the neoplasm, treatment modalities can be proposed. Thus, in one embodiment of the disclosed invention, a database of molecular characteristics of tumor-associated antibodies (TABs) and tumor-associated antigens (TAAs) is provided.

A database of molecular characteristics of different tumors and TABs has been developed that provides information regarding a specific treatment for individual tumors based on the neoplastic molecular marker characteristics of a tumor. Namely, the database relates the molecular description of a tumor; the response of tumor cells to various stimuli; and the profiles of antibodies against TAAs in a subject's blood based upon the specific neoplastic molecular markers. The classification is made possible, in part, because each tumor cell and its attendant set of TAAs has a predictable expression pattern of regulatory genes that is reflected in the blood profile of TABs.

EXAMPLES

Molecular Classification of Specific Tumors

The examples below demonstrate the molecular classification of specific types of tumors or neoplasms. Specific classes of tumors are subdivided into subclasses based upon gene expression profiles of regulatory factors at the MRNA and protein levels. The analysis below shows that using expression profile of transcriptional regulators in biopsy material or bodily fluids and/or blood profile of antibodies against specific transcriptional regulators allows to classify variety of tumor types into molecular subclasses. These subclasses are used for diagnostic purposes. Additionally, the tumor types classified below have been shown to demonstrate specific responses to a variety of treatments.

The list of neoplastic molecular marker used in the following examples is not finite. Using the methods disclosed herein, additional factors can be added to the arrays illustrated below to expand the classification system and to increase its specificity. Notwithstanding the expandability of the methods disclosed herein, the addition of new neoplastic molecular markers to the system does not alter the basic principle of the disclosed invention.

Tumors that develop from early stages of neural lineage (e.g., stem cells), express early markers of neurogenesis, such as helix-loop-helix (HLH) transcription factors of the neurogenin family, zinc finger transcription factors of the Zic family, high mobility group transcription factors of Sox family, homeodomain transcription factors of the Emx family, and a large number of other transcription factors that are involved in suppressing neural development, such as the HLH transcription factors of the HES family, homeodomain transcription factors of the MSX family, and inhibitory SMAD transcription factors. By contrast, tumors that develop from more differentiated neural cells express genes that are characteristic for this type of neoplasms. Late expressed homeodomain transcription factors of the LIM family, HLH transcription factors, and zinc finger transcription factors are all examples of transcription factors expressed in more differentiated neural cells.

Example 1

Gene Expression Profiling of Astrocytomas

The data presented in this example relates to the classification of astrocytomas. Diffuse, fibrillary astrocytomas are the most common neural tumors. They are typically divided into three grades of malignancy: World Health Organization (WHO) grade II astrocytoma, WHO grade III anaplastic astrocytoma and WHO grade IV glioblastoma multiforme (GBM). The WHO classification system is primarily based on morphological criteria and does not reflect the molecular nature of glioma cells. By contrast, the molecular classification provided by the described methods is based upon the expression of transcription factors in tumor cells.

Biopsy material from 11 patients with different grade astrocytomas was analyzed using different antibodies against transcription factors (tumor-associated antigens) that are characteristic for the early development of the nervous system. The results of this work are shown in Table 9.

The results shown in Table 10 were generated by applying general immunohistochemical techniques. Specifically, tissues were obtained, dissected, and immediately frozen on dry ice. Sections of 10 μm thick were obtained using a cryostat. Dissected tissue on slides was dried at room temperature for 30-90 minutes and then fixed with cold acetone/methanol (50/50) 2 minutes. Once dried, the slides were then treated with 0.05% trypsin for 10 minutes at 37° C., and then washed three times with phosphate buffered saline (PBS). The slides were then air-dried slides and washed with PBS for 5 minutes. The dried slides were then incubated in 50 mM anunonium chloride for 30 minutes, followed by a wash with PBS for 5 minutes. Non-specific binding was blocked by incubating the slides in a Tween/bovine serum albumin (BSA) solution for 30-45 minutes. Following the blocking step, the slides were incubated with a primary antibody specific for the indicated neoplastic molecular marker for 90 minutes at dilutions ranging from 1:100-1:600. The antibodies utilized were either commercially available or generated using standard techniques. Unbound primary antibodies were removed from the slides with washes performed three times for 5 minutes each using PBS. Following these washes, the slides were incubated with a secondary fluorochrome-conjugated antibody for 30 minutes. The slides were then washed four times for five minutes each in PBS. After the last wash the slides were mounted. The results of this work is shown below.

TABLE 10

Astrocytoma-specific profiling

|  | S1 | S2 | S3 | GM1 | GM2 | GM3 | GM4 | AA1 | AA2 | AA3 | AA4 | AA5 | AG1 | AG2 |
|---|---|---|---|---|---|---|---|---|---|---|---|---|---|---|
| NGN1 | − | − | − | ? | + | + | + | + | ? | + | + | − | − | − |
| NGN2 | + | + | + | + | + | + | + | + | + | + | + | − | + | + |
| NeuroD1 | + | + | + | + | + | + | + | − | + | + | + | + | + | + |
| NeuroD2 | + | − | − | + | − | + | − | − | + | − | − | − | + | − |
| ATH1 | − | − | − | +? | + | + | + | − | +? | + | − | − | − | − |
| ATH5 | + | + | + | + | + | + | + | + | + | + | + | + | + | + |
| ASH1 | − | − | − | − | − | − | + | − | − | − | − | − | − | − |
| NSCL2 | − | − | − | + | − | − | − | + | − | − | − | − | − | − |
| HES2 | + | + | + | + | +? | + | − | − | − | + | + | + | − | − |
| SHARP1 | + | + | + | + | + | + | + | − | + | + | + | + | + | − |
| Hey1/HRT1 | + | + | + | + | − | + | − | − | − | + | + | + | − | − |
| Hey2/HRT2 | + | + | + | + | + | + | + | − | + | + | + | + | + | + |
| HeyL/HRT3 | + | + | + | + | − | + | − | − | + | + | + | − | + | − |
| Groucho1 | − | + | − | − | − | − | − | − | − | + | − | − | − | − |
| Groucho3 | − | − | − | − | + | − | + | − | + | + | + | − | + | − |
| Groucho4 | + | − | − | − | − | − | − | − | + | + | + | + | + | − |
| EN1 | − | + | + | − | + | − | + | − | + | + | − | − | − | − |
| EN2 | − | − | − | − | − | − | − | + | − | − | − | − | − | − |
| SOX1 | +? | − | − | + | + | + | + | − | − | + | − | − | − | − |
| SOX2 | + | + | + | + | + | + | + | + | − | − | + | + | − | − |
| SOX3 | + | + | − | + | + | + | + | + | + | + | − | + | + | + |
| SOX10 | + | + | + | − | − | − | + | − | − | +? | + | + | − | − |
| Sal2 | + | + | − | − | − | − | − | − | − | + | + | − | − | − |
| Sal3 | − | − | − | − | − | − | − | − | + | − | − | − | − | − |
| PTX3 | − | − | + | − | + | + | + | − | − | + | − | − | − | + |
| NOT1 | − | − | − | − | + | − | + | − | − | + | − | − | − | − |
| Isl1 | + | + | + | − | + | + | + | + | + | + | + | + | + | + |
| LHX2 | − | − | − | − | + | − | + | − | − | + | + | − | − | − |
| LHX3 | − | − | − | − | − | − | − | − | − | + | − | − | − | − |
| LMO4 | − | − | + | − | + | − | − | − | + | + | − | − | + | − |
| NKX2.2 | + | − | − | − | − | − | − | − | − | − | − | − | − | − |
| NKX2.9 | + | − | − | − | − | − | + | − | − | + | − | − | − | − |
| NKX5.2 | + | − | + | + | − | + | − | + | + | + | + | + | + | + |
| GBX2 |  |  |  |  |  |  |  |  |  |  | + |  |  | − |
| Brn5 | + | + | + | + | − | + | + | + | + | − | + | + | + | + |

Abbreviations to Table 10:
S, control subject;
GM, glioblastoma multiforme;
AA, grade 2 astrocytoma;
AG, anaplastic glioma;
numbers refer to different subjects;
+, expressed;
−, not expressed;
+?, unable to identify/detect;
empty - no data.

Abbreviations to Table 10: S, control subject; GM, glioblastoma multiform; AA, grade 2astrocytoma; AG, anaplasti glioma; numbers refer to different subjects; =, expressed; −m, not expressed; =?, unable to identify/detect; empty—no data.

The analysis of these results demonstrate that individual tumors express unique sets of transcriptional regulators. For example, the characteristic differences of glioblastomas multiforme (GM) compared to anaplastic gliomas (AG) and grade 2 astrocytomas (AA) is the expression of Sox family of transcription factors.

Identity of Subclasses of Glioblastoma Multiforme Tumors

Five distinct subclasses of glioblastoma multiforme tumors were identified as follows: Subclass I: High expression of negative regulators of neural differentiation such as Msx genes and no expression of neuronal genes such as Neurogenins, Emx-s and Lim-s and negative regulators of HES family. Subclass II: High expression of HES genes and TGFβ signaling cascade molecules (SMADs), no neuronal genes. Subclass III: High expression of HES genes and neural genes of Neurogenin, NeuroD and ASH family. Subclass IV: High expression of HES genes and homeodomain genes of Lim and Emx family, no expression of NeuroD and ASH family HLH transcription factors. Subclass V: Moderate expression of HES and Msx family genes, no expression of neural homeodomain genes.

Example 2

Antibodies against Transcription Factors in the Blood of Subjects with Small Cell and Non Small Cell Lung Cancer—A Clinical Study Lung cancer is one of the most common neoplastic diseases in the United States, representing about 15% of all cancer cases and accounting for over one-fourth (28%) of cancer deaths in the United States (Hammar, 1994). It is the number one killer by cancer and in fact, kills more people than colon, prostate and breast cancer combined. Lung cancer is especially common among men in North America, Europe, and Oceania. There are many types of lung cancer, but most can be categorized into two basic types, small cell and non-small cell. Non-small cell lung cancer (NSCLC) that develops from lung neuroendocrine (NE) cells is a heterogeneous group of 3 clinically distinct types of tumors, including large cell carcinoma, and typical and atypical carcinoids. 80% of all lung tumors are diagnosed as NSCLCs. Carcinoids represent a rare group of tumors of NE system accounting for 1% to 3% of all lung tumors.

Identification of SCLC and NSCLC using auto-antibody profile from an afflicted subject's blood allows for noninvasive diagnosis of lung cancer. SCLC is characterized by the presence of the following set of antibodies against transcription factors NeuroD2, ATH5, Sox1, Sox2 and LMO4. When blood contains antibodies against these transcription factors then lung cancer patient has 80% probability to have SCLC. NSCLC is identifiable by the Groucho1, Sox2, Sox3 and Nkx5.2 antibodies.

Blood from 4 non-cancer patients, 7 patients diagnosed with well-developed small cell lung cancer (SCLC), and 8 patients diagnosed with well-developed non-small cell lung cancer (NSCLC) was used to identify diagnostic markers for the molecular distinction of the SCLC and NSCLC disease states. The blood sera from these individuals was dot blot analyzed for the presence of transcription factor-specific TABs.

This analysis showed that these two tumor types are well-discriminated by different sets of diagnostic markers in the blood (Table 11). The analysis of this data indicates that the SCLC neoplastic disease state is characterized by the presence antibodies against transcription factors NeuroD2, ATH5, Sox1, Sox2, and LMO4 in the subject's blood. The NSCLC neoplastic disease state is characterized by the presence of antibodies against HeyL/HRT3, Sox1, Sox2, and Nkx5.2.

TABLE 11

Lung Cancer-Specific TAB Profile

| | control | | | | SCLC | | | | | | | NSCLC | | | | | | | |
|---|---|---|---|---|---|---|---|---|---|---|---|---|---|---|---|---|---|---|---|
| | 1 | 2 | 3 | 4 | 1 | 2 | 3 | 4 | 5 | 6 | 7 | 1 | 2 | 3 | 4 | 5 | 6 | 7 | 8 |
| NGN1 | + | | | | | | | | | | | | | | | | | | |
| NGN2 | | | | | + | + | + | | + | | | | + | | | | | | |
| NGN3 | | | | | | | | | | | | | | | | | | + | |
| NeuroD1 | | | | | + | | | | | | | | | | | | | | |
| NeuroD2 | | | | | + | + | + | + | + | + | + | | + | | | + | | | |
| NeuroD3 | | | | | | | | | | | | | | | | | | | |
| ATH1 | | | | | | | | ? | | | | | | | | | | | |
| ATH5 | | | | | + | + | + | | + | + | + | | + | | | + | | | |
| ASH1 | | | | | | | | | | | | | | | | | | | |
| NSCL1 | | + | | | | | | | | | | | | | | | | | |
| NSCL2 | | | | | | + | | + | | | | | + | | | | | | |
| HES1 | | | | | | | | | | | | | | | | | | | |
| HES2 | | | | | + | | | + | + | | | | | + | | | | | + |
| HES3 | | | | | | | | | | | | | | | | | | | |
| HES5 | | | | | | | | | | | | | | | | | | | |
| SHARP1 | | | | | + | | | | + | | | | | | | | | | |
| SHARP2 | | | | | | | | | | | | | | | | | | | |
| Hey1/HRT1 | | | | | | | | | | | | | | | | | | | |
| Hey2/HRT2 | | + | | | | | | | | | | | | | | | | | |
| HeyL/HRT3 | | | | | | | | | | | | | | + | | + | + | + | + |
| Groucho1 | | | | | | + | | + | | | | | | + | | | | | |
| Groucho2 | | | | | | | | | | | | | | | | | | | |
| Groucho3 | | | | | | | | | | | | | | | | | | | |
| Groucho4 | | | | | | | | | | | | | | | | | | | |

TABLE 11-continued

Lung Cancer-Specific TAB Profile

| | control | | | | SCLC | | | | | | | NSCLC | | | | | | | |
|---|---|---|---|---|---|---|---|---|---|---|---|---|---|---|---|---|---|---|---|
| | 1 | 2 | 3 | 4 | 1 | 2 | 3 | 4 | 5 | 6 | 7 | 1 | 2 | 3 | 4 | 5 | 6 | 7 | 8 |
| EN1 | | + | | | | | | | | | | | | | | | | | |
| EN2 | | | | | | | | | | | | | | | | | | | |
| SOX1 | | | | | + | + | + | | + | | + | + | + | + | | + | | + | |
| SOX2 | | + | | | + | + | + | | + | | + | | + | + | + | + | | | |
| SOX3 | | | | | | | | | | | | | | | | | | | |
| SOX10 | | | | | | | + | + | | + | + | + | | | | + | | + | |
| SOX11 | | | | | | | + | | | + | | | | | | + | | + | |
| RBP-Jk | | | | | | | | | | | | | | | | | | | |
| Sall1 | | | | | | | | + | | + | | | + | | + | | | | + |
| Sal2 | | | | | | + | | | | | | | | | | | | | |
| Sal3 | | | | | | | | | | | | | | | | | | | |
| Phox2A | + | | | | | | | | + | | | | | | + | | | | |
| Phox2B | | | | | | | | | | | | | | | | | + | | |
| PTX3 | | | + | | | | | | | | | | | | | | | | |
| NOT1 | | | | | | | | | | | | | | | | | | | |
| Isl1 | | | | | + | + | | | + | | | | | | + | | | | |
| LHX2 | | | | | + | | | | + | | | | | + | | + | | | |
| LHX3 | | | | | | | | | | | | | | | | | | | |
| LHX4 | | | | | | | | | | | | | | | | | | | |
| LHX5 | | | | | | | | | | | | | | | | | | | |
| LMO4 | | | | | + | + | + | | + | + | | | | | + | | | | |
| NKX2.2 | | | | | | | | | | | | | | | | | | | |
| NKX2.9 | | | | | | | | | | | | | | | | | | | |
| NKX.5.1 | | | | | | | | | | | | | | | | | | | + |
| NKX5.2 | | | | | | | | | | | | + | + | + | | | + | + | |
| DLX1 | | | | | | | | | | | | | | | | | | | |
| DLX2 | | | | | | | | | | | | | | | | | | | |
| DLX5 | | | | | | | | | | | | | | | | | | | |
| GBX2 | | | | | | + | | | + | + | | | | | + | | | | |
| Brn5 | | | | | | | + | | | + | | | | | + | | | + | |

Abbreviations to Table 11:
control, control subject;
SCLC, small cell lung cancer;
NSCLC, non-small cell lung cancer;
numbers refer to different subjects;
+, expressed;
?, not able to identify/detect;
empty, not expressed.

Abbreviations to Table 11:control, control subject; SCLC, small cell lung cancer; NSCLC, non-small cell lung cancer; numbers refer to different subjects; +, expressed; ?, not able to identify/detect; empty, not expressed.

Example 3

Profile of Auto-Antibodies Against Transcription Factors in the Blood of Subjects with Prostate Cancer: A Clinical Study Prostate cancer is the most common form of neoplastic disease in men. Prostate cancer is the second leading cause of cancer death after lung cancer. 80% of men over the age of 65 who have cancer have prostate cancer (data of American Cancer Society). One in five men will develop prostate cancer in their lifetime. Next to age, race tends to be important cause of this cancer, since African-American males have the highest rate of prostate cancer in the world, and they tend to be diagnosed at late stage. Adenocarcinoma of the prostate is one of the most common tumors in men and accounts for 10% of deaths from malignant disease in males in the United States. Only a small proportion of these cases becomes clinically apparent prior to death, the remainder being latent carcinoma. Although some immunological diagnostic assays are available, the only reliable procedure for definitive diagnosis of prostatic carcinoma is by open perineal biopsy. Needle biopsies and cytologic studies of prostatic fluid are unreliable for the diagnosis of early cancer but are useful methods of obtaining a histological diagnosis in the more advanced cases.

To evaluate presence of TABs against transcriptional regulators in patients' blood as a diagnostic marker for molecular subgroups of prostate cancer, the blood serum of 10 noncancer patients and of 21 patients diagnosed with well-developed tumors was analyzed. It was established that these tumors exhibited neuroendocrine-like differentiation by examining the levels of chromogranin A in the blood sera, which were exceedingly higher in the blood of patients with cancer than in the sera of the control group. Blood samples were collected during the period of 1990-1995, aliquoted and stored at −80° C. None of the samples had been previously thawed. All patients with prostate cancer have been receiving treatment, either androgen ablation therapy or radiotherapy.

Peptides (see Tables 1-8) in the concentration of 1 mg/ml ($H_2O$) were blotted in 0.25 µl volumes onto nitrocellulose filter. The dried filter was exposed to a blocking solution (PBS, 1% Tween 20, 1% casein, 1% goat serum; and 5 mM EDTA) overnight at 4° C. After four washes with PBS, 0.1% Tween 20, the filter was incubated with goat anti-human Ig-conjugated to alkaline phosphatase secondary antibody (Dako) which had been diluted 1:1000 in the blocking solution. After four washes with PBS, 0.1% Tween 20, color reaction for peroxidase was performed using a mix of diaminobenzidine (DAB, Sigma-D-5637; 10 mg in 5 ml methanol)

and chloronaphtole (30 mg in 5 ml methanol) as a substrate. Each time a fresh substrate solution (0.5 ml of DAB stock+0.5 ml chloronaphtole stock+4 ml PBS+5 microliters of H₂O₂) was made. Finally, densitometric analyses or alternatively qualitative evaluation of the filters was performed to determine the presence or absence of a signal on the blot.

TABLE 12

Profile of Auto-Antibodies Against Transcription Factors In The Blood Of Subjects With Prostate Cancer

| | control patients | | | | | | | | | | Prostate carcinoma patients | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 | 7 | 8 |
| NGN1 | | | | | | | | | | | 1 | | | | | | 1 | |
| NGN2 | | | | | | | 1 | | | | 1 | 1 | | | | 1 | | |
| NGN3 | | | | | | | | | | | | | 1 | | | | 1 | 1 |
| NeuroD1 | | | | | | | | | | | 1 | | | | | | 1 | |
| NeuroD2 | | | 1 | | | | | | | | 1 | 1 | | 1 | 1 | 1 | | |
| NeuroD3 | | | | | | | | | | | | | | | | | | |
| ATH1 | | | | | | | | | | | 1 | 1 | | 1 | 1 | 1 | | |
| ATH5 | | | | | | | | | | | 1 | 1 | 1 | 1 | 1 | 1 | | 1 |
| ASH1 | | | | | | | | | | | | | | | | | | |
| NSCL1 | | | | | | | | | | | | | | | | | | |
| NSCL2 | | | | | | | | | | | | | | | | | 1 | |
| HES1 | | | | | | | | | | | | | | | | | | |
| HES2 | | | | | | | | | | | 1 | | 1 | | 1 | 1 | | 1 |
| HES3 | | | | 1 | | 1 | | | | | 1 | | | | | | | |
| HES5 | | | | | | | | | | | | | | | | | | |
| SHARP1 | | | | | | | | | | | | 1 | | | | | 1 | 1 |
| SHARP2 | | | | | | | | | | | | 1 | | | | | | |
| Hey1/HRT1 | | | | | | | | | | | | | | | | | | |
| Hey2/HRT2 | | | | | | | | | | | | | | | | | | |
| HeyL/HRT3 | | | | | | | | | | | | | | 1 | 1 | 1 | | |
| Groucho1 | | | | | | | | | | | | | | | | | | |
| Groucho2 | | | | | | | | | | | | | | | | | 1 | |
| Groucho3 | | | | | | | | | | | | | | | | | | |
| Groucho4 | | | | | | | | | | | | | | | | | | |
| EN1 | | | 1 | | | | | | | 1 | | | | | | | | |
| EN2 | | | | | | | | | | | | | | | | | | |
| SOX1 | | | | | | | | | | | 1 | | 1 | | 1 | 1 | | 1 |
| SOX2 | | | 1 | | | 1 | | | | | 1 | 1 | 1 | | 1 | 1 | 1 | 1 |
| SOX3 | | | | | | | | | | | | | | 1 | | | 1 | 1 |
| SOX10 | | | | | | | | | | | 1 | | | | | | | |
| SOX11 | | | | | | | | | | | | | | | | | | |
| RBP-Jk | | | | | | | | | | | | | | | | | | |
| Sall1 | | | | | | | | | | | | | 1 | | | | 1 | 1 |
| Sal2 | | | | | | | | | | | | | | | | | | |
| Sal3 | | | | | | | | | | | | | | | | | | |
| Phox2A | 1 | | | | | | | | | | | | | | | | | |
| Phox2B | | | | | | | | | | | | | | | | | | |
| PTX3 | | | | | | | | | | | 1 | 1 | | | | | | |
| NOT1 | | | | | | | 1 | | | | | | | | | | | |
| Isl1 | | | | | | | | | | | 1 | 1 | | 1 | 1 | 1 | | |
| LHX2 | | | | | | | | | | | | | | | | | | |
| LHX3 | | | | | | | | | | | 1 | 1 | 1 | | | | 1 | |
| LHX4 | | | | | 1 | | | | | | | | | | | | | |
| LHX5 | | | | | | | | | | | | | | | | | | |
| LMO4 | | | | | | | | | | | 1 | 1 | | 1 | 1 | 1 | | |
| NKX2.2 | | | | | | | | | | | | | 1 | | | | 1 | 1 |
| NKX2.9 | | | | | | | | | | | | | | | | | | |
| NKX.5.1 | | | | | | | | | | | | | | | | | | |
| NKX5.2 | | | | | | | | | | | | | | | | | | |
| DLX1 | | | | | | | | | | | | | | | | | | |
| DLX2 | | | | | | | | | | | | | | | | | | |
| DLX5 | | | | | | | | | | | | | | | | | | |
| GBX2 | | | 1 | | | 1 | | | | | 1 | 1 | | 1 | 1 | 1 | | |
| Brn5 | | | | | | | | | | | 1 | 1 | | 1 | | | | 1 |

| | Prostate carcinoma patients | | | | | | | | | | | | |
|---|---|---|---|---|---|---|---|---|---|---|---|---|---|
| | 9 | 10 | 11 | 12 | 13 | 14 | 15 | 16 | 17 | 18 | 19 | 20 | 21 |
| NGN1 | | | | | | | 1 | | | 1 | | | |
| NGN2 | 1 | | | | | | 1 | | | | | 1 | 1 |
| NGN3 | | | | | | | 1 | | | 1 | | 1 | 1 |
| NeuroD1 | | | | | | | | | | 1 | | | |
| NeuroD2 | 1 | 1 | | 1 | 1 | 1 | | | | 1 | | 1 | 1 |
| NeuroD3 | | | | | | | | | | | | | |
| ATH1 | 1 | 1 | | 1 | 1 | 1 | | | | 1 | | 1 | |

TABLE 12-continued

Profile of Auto-Antibodies Against Transcription Factors In The Blood Of Subjects With Prostate Cancer

| | 1 | 2 | 3 | 4 | 5 | 6 | 7 | 8 | 9 | 10 | 11 | 12 | 13 |
|---|---|---|---|---|---|---|---|---|---|---|---|---|---|
| ATH5 | 1 | 1 | | 1 | 1 | 1 | 1 | 1 | 1 | 1 | | 1 | 1 |
| ASH1 | | | | | | | | | | | | | |
| NSCL1 | | | | | | | | | | | | | |
| NSCL2 | | | | | | | | | | 1 | | | |
| HES1 | | | | | | | | | | | | | |
| HES2 | | 1 | 1 | | 1 | | 1 | 1 | | | | 1 | 1 |
| HES3 | | | | | | | | | | | | | |
| HES5 | | | | | | | | | | | | | |
| SHARP1 | | | 1 | | | | 1 | 1 | 1 | | | | 1 |
| SHARP2 | | | | | | | 1 | | 1 | | | | |
| Hey1/HRT1 | | | | | | | | | | | | | |
| Hey2/HRT2 | | | | | | | | | | | | | |
| HeyL/HRT3 | | | | 1 | | | | | | | | | |
| Groucho1 | | | | | | | | | | | | | |
| Groucho2 | | | | | | | | | | | | | |
| Groucho3 | | | | | | | | | | 1 | | | |
| Groucho4 | | | | | | | | | | | | | |
| EN1 | | | | | | | | | | | | | |
| EN2 | | | | | | | | | | | | | |
| SOX1 | | 1 | 1 | | 1 | | 1 | 1 | 1 | | 1 | 1 | |
| SOX2 | 1 | | 1 | | 1 | 1 | | | 1 | 1 | | | 1 |
| SOX3 | | | | 1 | | | 1 | 1 | 1 | | 1 | 1 | |
| SOX10 | | | 1 | | | | | 1 | | | | | 1 |
| SOX11 | | | | | | | | | | | | | |
| RBP-Jk | | | | | | | | | | | | | |
| Sall1 | | | | 1 | | | 1 | 1 | 1 | | 1 | | 1 |
| Sal2 | | | | | | | | | | | | | |
| Sal3 | | | | | | | | | | | | | |
| Phox2A | | | | | | | | | | | | | |
| Phox2B | | | | | | | | | | | | | |
| PTX3 | | | | | | | 1 | | | | | | |
| NOT1 | | | | | | | | | | | | | |
| Isl1 | 1 | 1 | | 1 | 1 | 1 | | | | 1 | | 1 | |
| LHX2 | | | | | | | | | | | | | |
| LHX3 | | | 1 | | 1 | 1 | 1 | | | | 1 | | |
| LHX4 | | | | | | | | | | | | | |
| LHX5 | | | | | | | | | | | | | |
| LMO4 | 1 | 1 | | 1 | 1 | 1 | | | | | 1 | | |
| NKX2.2 | | | | | | | 1 | 1 | 1 | | 1 | | |
| NKX2.9 | | | | | | | | | | | | | |
| NKX.5.1 | | | | | | | | | | | | | |
| NKX5.2 | | | | | | | | | | | | | |
| DLX1 | | | | | | | | | | | | | |
| DLX2 | | | | | | | | | | | | | |
| DLX5 | | | | | | | | | | | | | |
| GBX2 | 1 | 1 | | 1 | 1 | 1 | | | | | 1 | | 1 |
| Brn5 | | | 1 | 1 | 1 | 1 | | | 1 | 1 | | | 1 |

Abbreviations to Table 12:
numbers in the top row of the Table refer to different subjects;
1, presence of the TAB;
empty, absence of the TAB.

Abbreviations to Table 12: numbers in the top row of the Table refer to different subjects; 1, presence of the TAB; empty, absence of the TAB.

Based on the presence of TABs in the blood of the patients diagnosed with prostate carcinoma, two subgroups of patients were identified. Group I typically had antibodies against: NeuroD2, ATH1, Isl1, LMO4, GBX2, including patients 1,2,4,5,6,9,10,12,13,14,18,20. Five of them (41.6%) are dead already. Group II had antibodies against: Nkx2.2, Sall1, Sharp1; including patients 3,7,8,15,16,17,19. In this group only one patient (14.3%) has died. Based on the survival data, it was also observed that patients with prostate carcinoma of group II respond better to hormone and radiotherapy.

Example 4

Gene Expression Profiling of Neuroblastomas

The expression of various regulatory genes expressed at early stages of neurogenesis were examined in five different human neuroblastomas. All neuroblastomas exhibit expression of a variety transcription regulatory factors that demarcate the highly mitotic active region in the nervous system—the subventricular zone. However, neuroblastomas can be clearly identified by the presence and extent of different signaling pathways that are implicated during neurogenesis, particularly by the presence of molecular markers such as BMP/TGFβ, SHH, and Notch. Furthermore, in different neuroblastomas proneural genes ASH-1 and Neurogenin1 are expressed in complementary fashion. In addition, several other bHLH genes (e.g., Hes5, Hey1, NeuroD1, NeuroD2, and NeuroD3(6)) exhibit similar neuroblastoma-specific restriction, as do Neurogenin1 and ASH1, forming the signatures for the molecular classification of neuroblastomas.

Briefly, the expression of various transcriptional regulatory factors in different human neuroblastomas was examined using RT-PCR analysis. First strand cDNAs were synthesized with reverse transcriptase (Superscript$^{II}$, Life Technologies Inc.) using 5-10 μg of mRNA from different cell lines as a template. PCR reactions were performed in the volume of 25 μl containing 1/10 of RT reaction as a template and GC-Rich PCR System or the Expand™ Long Distance PCR System kit (Roche) according to manufacturer's instructions. DNA was amplified using in most cases the following conditions: 94° C. (2 min); 35-40 cycles of 94° C. (30s), 56° C. (40s), 72° C. (150s). For all combinations of primers, the annealing temperature and the number of cycles was optimized beforehand. All amplified PCR products were sequenced to rule out false positives using fmol® DNA Cycle Sequencing System (Promega. The amplified RT-PCR products were resolved on 1.0-1.2% agarose gel.

TABLE 13

RT-PCR Analysis of Neuroblastomas

| | control | | | | | GDNF + TGFβ1 | | | | |
|---|---|---|---|---|---|---|---|---|---|---|
| | 1 | 2 | 3 | 4 | 5 | 1 | 2 | 3 | 4 | 5 |
| Gata-2 | 1 | 1 | 1 | 1 | 1 | 1 | 1 | 1 | 1 | 1 |
| Gata-3 | 1 | 1 | 1 | 1 | 1 | 1 | 1 | 1 | 1 | 1 |
| Pbx-1 | 1 | 1 | 1 | 1 | 1 | 1 | 1 | 1 | 1 | 1 |
| LMO4 | 1 | 1 | 1 | 1 | 1 | 1 | 1 | 1 | 1 | 1 |
| Sox2 | 1 | 1 | 0 | 0 | 0 | 1 | 1 | 0 | 0 | 1 |
| Sox11 | 1 | 1 | 1 | 1 | 1 | 1 | 1 | 1 | 1 | 1 |
| Bmp-2 | 1 | 1 | 0 | 0 | 0 | 1 | 0 | 0 | 0 | 0 |
| Bmp-6 | 1 | 1 | 0 | 0 | 0 | 1 | 0 | 0 | 0 | 0 |
| noggin | 1 | 1 | 0 | 0 | 0 | 1 | 1 | 0 | 0 | 0 |
| chordin | 1 | 1 | 0 | 0 | 0 | 1 | 0 | 0 | 0 | 0 |
| SMAD6 | 1 | 1 | 0 | 0 | 0 | 1 | 0 | 0 | 0 | 0 |
| SMAD7 | 1 | 1 | 1 | 1 | 1 | 1 | 1 | 1 | 1 | 1 |
| Msx1 | 1 | 1 | 0 | 0 | 0 | 1 | 1 | 0 | 0 | 0 |
| Msx2 | 1 | 1 | 0 | 0 | 0 | 1 | 1 | 0 | 0 | 0 |
| Gli1 | 1 | 1 | 0 | 0 | 0 | 1 | 1 | 0 | 0 | 0 |
| Gli2 | 1 | 1 | 1 | 1 | 1 | 1 | 1 | 1 | 1 | 1 |
| Gli3 | 1 | 1 | 0 | 1 | 0 | 1 | 1 | 0 | 1 | 0 |
| Zic1 | 1 | 0 | 0 | 0 | 1 | 1 | 0 | 0 | 0 | 0 |
| Zic2 | 1 | 1 | 0 | 0 | 0 | 1 | 1 | 0 | 0 | 0 |
| Zic3 | 1 | 0 | 0 | 0 | 0 | 1 | 0 | 0 | 0 | 0 |
| Irx2a | 1 | 1 | 1 | 1 | 1 | 1 | 0 | 0 | 1 | 1 |
| Irx3 | 1 | 0 | 1 | 0 | 0 | 0 | 0 | 0 | 0 | 0 |
| NN1 | 0 | 0 | 0 | 0 | 0 | 0 | 0 | 0 | 0 | 0 |
| NN3 | 0 | 0 | 1 | 0 | 0 | 0 | 0 | 1 | 0 | 0 |
| Ash-1 | 0 | 0 | 1 | 1 | 1 | 1 | 1 | 1 | 1 | 1 |
| Olf-1 | 1 | 1 | 1 | 1 | 1 | 1 | 1 | 1 | 1 | 1 |
| Olf-1H | 1 | 1 | 1 | 1 | 1 | 1 | 1 | 1 | 1 | 1 |
| NeuroD1 | 0 | 0 | 1 | 1 | 1 | 1 | 1 | 1 | 1 | 1 |
| NeuroD2 | 1 | 1 | 1 | 1 | 1 | 1 | 0 | 0 | 0 | 0 |
| NeuroD3 | 1 | 1 | 0 | 0 | 0 | 1 | 1 | 0 | 0 | 0 |
| NSCL1 | 1 | 1 | 1 | 1 | 1 | 1 | 1 | 1 | 1 | 1 |
| NSCL2 | 1 | 1 | 1 | 0 | 0 | 0 | 0 | 0 | 0 | 0 |
| Hes-1 | 1 | 1 | 1 | 1 | 1 | 1 | 1 | 1 | 1 | 1 |
| Hes-5 | 0 | 0 | 1 | 1 | 1 | 0 | 0 | 1 | 1 | 1 |
| Hey1 | 0 | 0 | 1 | 1 | 1 | 1 | 1 | 1 | 1 | 1 |
| Hey2 | 1 | 1 | 1 | 0 | 0 | 1 | 1 | 1 | 1 | 1 |
| HeyL | 1 | 1 | 0 | 1 | 0 | 1 | 0 | 1 | 1 | 0 |
| MyT-1 | 0 | 1 | 1 | 1 | 0 | 1 | 1 | 1 | 1 | 1 |
| MyT-2 | 0 | 0 | 1 | 0 | 0 | 0 | 1 | 0 | 0 | 1 |
| MyT-3 | 0 | 0 | 0 | 0 | 0 | 0 | 0 | 0 | 0 | 0 |
| Otx1 | 1 | 1 | 0 | 0 | 0 | 0 | 1 | 1 | 1 | 1 |
| Otx2 | 1 | 0 | 0 | 0 | 0 | 0 | 0 | 0 | 0 | 1 |
| Pax6 | 1 | 1 | 0 | 0 | 1 | 0 | 0 | 0 | 0 | 0 |
| Brn4 | 1 | 1 | 1 | 1 | 0 | 1 | 0 | 0 | 0 | 1 |
| Brn5 | 1 | 1 | 1 | 1 | 1 | 1 | 1 | 0 | 0 | 0 |

TABLE 13-continued

RT-PCR Analysis of Neuroblastomas

| | control | | | | | GDNF + TGFβ1 | | | | |
|---|---|---|---|---|---|---|---|---|---|---|
| | 1 | 2 | 3 | 4 | 5 | 1 | 2 | 3 | 4 | 5 |
| Dlx2 | 1 | 1 | 0 | 0 | 0 | 1 | 1 | 1 | 1 | 1 |
| Dlx7 | 1 | 1 | 1 | 1 | 1 | 1 | 1 | 0 | 1 | 0 |
| Nkx2.5 | 0 | 1 | 1 | 1 | 0 | 1 | 1 | 1 | 1 | 1 |
| Neu | 0 | 0 | 1 | 1 | 1 | 1 | 1 | 1 | 1 | 1 |
| Med6 | 1 | 1 | 1 | 1 | 1 | 1 | 1 | 0 | 0 | 0 |
| GFAP | 0 | 0 | 0 | 0 | 1 | 1 | 1 | 1 | 1 | 1 |
| βIIItub | 0 | 0 | 1 | 0 | 1 | 1 | 1 | 1 | 1 | 1 |

N.B.: The numbers in the top row of the Table refer to different subjects; a "1" value refers to mRNA expression; and a "0" value connotes no expression of mRNA.

The effect of growth factors on the proliferation and differentiation of five human neuroblastomas (Table 14) was also examined. The data established that transcriptional regulatory factor networks operational in human neuroblastoma cells are involved in neural differentiation of human neuroblastoma cells in response to growth factor treatment. The change in expression patterns of transcriptional regulatory factors upon growth factor-treatment of neuroblastomas is compared to the extent of neural differentiation of these tumor cells as examined by the expression of various neural-specific markers. Two major adaptations were observed in the TF networks of NBs upon GF (GDNF and TGFβ1) treatment. The first adaptation included genes that exhibited cell-autonomous regulation and showed no change in their expression upon treatment. This group of genes comprised mostly of early negative regulators and TFs characterizing the fate switches to specific neural lineages. The second adaptation included genes that exhibited signal-dependent regulation and their expression was affected by GF treatment. This group comprised mostly of TFs associated with specification of neuronal identity, e.g proneural and neurogenic genes. Ultimately, using cluster analysis methods, we demonstrated that information relevant to NB classification that considers cellular potential of a tumor for GF-induced differentiation can be reduced to distinct sets of at least 5 transcription regulators which are implicated in neurogenesis. These observations suggest a basic strategy for NB diagnostics and therapeutics whereby a relatively small number of TFs, which are followed as identifiers of development and cell function, could be used to classify tumors according to their cellular potential for differentiation.

Results of the analyses demonstrate that neuroblastomas have specific responses to growth factors, and likely this response depends on the expression profile of regulatory factors which can be exploited as a prognostic marker for therapeutic outcome.

TABLE 14

The effect of GDNF and TGFβ1 on the proliferation of neuroblastomas

| | 1 | 2 | 3 | 4 | 5 |
|---|---|---|---|---|---|
| TGFβ1/ GDNF | 3.6↑ | 3.6↓ | 2.3↑ | NE | NE |

Human NB cells were grown for 6 days on laminin-coated 24-well plate in DMEM/F-12/B27 media in the presence of GDNF (100 ng/ml) and TGFβ1 (100 ng/ml). After 6 days cells were dissociated and an aliquot of cells was counted using hemocytometer. Values represent the relative change (in folds) in cell number normalized to the relative change in cell number of GF-untreated cultures. Abbreviations: NE,—no effect in comparison with control; ↑—enhanced proliferation in comparison with control; ↓—reduced proliferation in comparison with control.

These data indicate that individual neuroblastomas reflect a certain stage of neural development, characterized by the expression of stage-specific regulatory genes. These observations suggest a basic strategy for neuroblastoma diagnostics and therapeutics whereby a relatively small number of transcriptional regulatory factors, which are followed as identifiers of cell function and development, could be used to monitor and promote cellular potential for differentiation in tumors.

Example 5

Gene Expression Profiling of Non Small Cell Lung Cancer

Gene expression profiling of NSCLC cells was performed using RT-PCR techniques, establishing that individual NSCLCs reflect a certain stage of neural development, characterized by the expression of stage-specific regulatory genes, and revealing that Zic family of TFs, MyT-2, Hes-5, SMAD6 forming the signatures of the molecular marker-based classification of carcinoids.

Total RNA was isolated from 500,000 cells using an acid-phenol extraction method as described Timmusk et al., Neuron 10(3), 475-489 (1993). RT-PCR analyses was performed as detailed in Palm et al., Brain Res. Mol. Brain Res. 78(1-2), 192-195 (2000) using 45 cycles in each amplification. Primer sets were designed in a manner that sense and antisense primers recognized different exons facilitating the discrimination between RT-PCR amplification products of genomic DNA and mRNA. (Table 9). All amplified PCR products were sequenced to rule out false positives. The results from this work are shown in Table 15.

TABLE 15

| RT-PCR Analysis of NSCLC | | | | | | | | | | |
|---|---|---|---|---|---|---|---|---|---|---|
| | control | | | | | GDNF + TGFβ1 | | | | |
| | 1 | 2 | 3 | 4 | 5 | 1 | 2 | 3 | 4 | 5 |
| Gata-2 | 1 | 1 | 1 | 1 | 1 | 1 | 1 | 1 | 1 | 1 |
| Gata-3 | 1 | 1 | 0 | 0 | 0 | 1 | 1 | 0 | 0 | 1 |
| Olf-1 | 0 | 1 | 1 | 0 | 1 | 0 | 1 | 1 | 0 | 1 |
| Olf-1H | 1 | 1 | 1 | 1 | 1 | 1 | 1 | 1 | 0 | 1 |
| Pbx-1 | 1 | 1 | 1 | 1 | 0 | 1 | 1 | 1 | 1 | 0 |
| LMO4 | 1 | 1 | 1 | 1 | 1 | 1 | 1 | 1 | 1 | 1 |
| Id3 | 1 | 1 | 1 | 1 | 1 | 1 | 1 | 1 | 1 | 1 |
| Dlx2 | 1 | 1 | 1 | 1 | 1 | 1 | 1 | 1 | 1 | 1 |
| Sox2 | 1 | 1 | 1 | 1 | 0 | 1 | 1 | 1 | 1 | 1 |
| Sox11 | 0 | 0 | 1 | 1 | 1 | 0 | 0 | 1 | 1 | 1 |
| Bmp-2 | 1 | 1 | 1 | 1 | 1 | 1 | 1 | 1 | 1 | 1 |
| Bmp-6 | 1 | 1 | 1 | 1 | 0 | 1 | 1 | 1 | 1 | 1 |
| noggin | 0 | 1 | 1 | 0 | 0 | 0 | 1 | 1 | 0 | 0 |
| chordin | 1 | 1 | 1 | 1 | 1 | 1 | 1 | 1 | 1 | 1 |
| SMAD6 | 1 | 1 | 0 | 0 | 1 | 1 | 1 | 1 | 0 | 1 |
| SMAD7 | 1 | 1 | 1 | 1 | 1 | 1 | 1 | 1 | 1 | 1 |
| Msx1 | 1 | 1 | 1 | 0 | 0 | 1 | 1 | 1 | 0 | 0 |
| Msx2 | 0 | 1 | 0 | 0 | 0 | 1 | 0 | 0 | 0 | 0 |
| Hes-1 | 1 | 0 | 0 | 1 | 1 | 1 | 1 | 1 | 1 | 1 |
| Hes-5 | 1 | 1 | 1 | 0 | 1 | 1 | 1 | 1 | 0 | 1 |
| Hey1 | 1 | 1 | 1 | 1 | 1 | 1 | 1 | 1 | 1 | 1 |
| Hey2 | 1 | 1 | 1 | 1 | 0 | 1 | 1 | 1 | 0 | 1 |
| HeyL | 1 | 1 | 1 | 1 | 1 | 1 | 0 | 1 | 1 | 1 |
| MyT-1 | 1 | 1 | 1 | 1 | 1 | 0 | 1 | 1 | 1 | 1 |
| MyT-2 | 0 | 1 | 1 | 0 | 1 | 0 | 1 | 1 | 0 | 1 |
| MyT-3 | 1 | 1 | 1 | 1 | 1 | 1 | 1 | 1 | 1 | 1 |
| SHH | 1 | 1 | 0 | 0 | 0 | 0 | 1 | 0 | 0 | 0 |
| Gli1 | 1 | 1 | 0 | 1 | 0 | 1 | 1 | 1 | 0 | 1 |
| Gli2 | 1 | 0 | 1 | 0 | 1 | 0 | 0 | 0 | 0 | 0 |
| Gli3 | 0 | 1 | 0 | 0 | 0 | 0 | 0 | 1 | 0 | 0 |
| Zic1 | 0 | 0 | 0 | 1 | 0 | 0 | 0 | 0 | 1 | 0 |
| Zic2 | 1 | 1 | 1 | 1 | 0 | 0 | 1 | 1 | 0 | 0 |
| Zic3 | 0 | 0 | 1 | 0 | 0 | 0 | 1 | 1 | 0 | 0 |
| Irx2a | 1 | 1 | 0 | 1 | 1 | 0 | 1 | 1 | 1 | 1 |
| Irx3 | 0 | 0 | 0 | 0 | 0 | 0 | 0 | 0 | 0 | 0 |
| NN1 | 0 | 0 | 0 | 0 | 0 | 0 | 0 | 0 | 0 | 0 |
| NN3 | 0 | 1 | 1 | 1 | 1 | 0 | 1 | 1 | 1 | 0 |
| Ash-1 | 1 | 1 | 1 | 1 | 0 | 1 | 1 | 1 | 1 | 0 |
| NeuroD1 | 1 | 1 | 0 | 1 | 1 | 1 | 1 | 0 | 1 | 1 |
| NeuroD2 | 1 | 1 | 0 | 1 | 1 | 1 | 1 | 1 | 1 | 1 |
| NeuroD3 | 0 | 0 | 0 | 0 | 1 | 0 | 0 | 0 | 0 | 1 |
| NSCL1 | 1 | 1 | 1 | 1 | 1 | 1 | 1 | 1 | 1 | 1 |
| NSCL2 | 0 | 0 | 0 | 0 | 1 | 0 | 0 | 0 | 0 | 1 |
| Emx1 | 1 | 1 | 1 | 1 | 0 | 1 | 1 | 1 | 0 | 1 |
| Emx2 | 0 | 0 | 0 | 0 | 1 | 0 | 0 | 0 | 0 | 1 |
| Gbx2 | 1 | 1 | 1 | 0 | 1 | 0 | 1 | 1 | 1 | 0 |
| Otx1 | 1 | 1 | 1 | 1 | 1 | 1 | 1 | 1 | 1 | 1 |
| Otx2 | 0 | 0 | 0 | 0 | 0 | 0 | 0 | 0 | 0 | 0 |
| Pax6 | 1 | 0 | 0 | 1 | 1 | 1 | 0 | 0 | 1 | 1 |
| Okt2 | 1 | 1 | 1 | 1 | 1 | 1 | 1 | 1 | 1 | 1 |
| Brn2 | 1 | 0 | 1 | 0 | 0 | 0 | 0 | 1 | 1 | 0 |
| Brn4 | 0 | 0 | 0 | 1 | 0 | 0 | 0 | 0 | 0 | 1 |
| Brn5 | 1 | 1 | 1 | 1 | 1 | 1 | 1 | 1 | 1 | 1 |
| Dlx7 | 1 | 1 | 0 | 1 | 1 | 1 | 1 | 1 | 1 | 1 |
| Nkx2.5 | 1 | 1 | 0 | 0 | 0 | 1 | 1 | 0 | 0 | 0 |
| Internexin | 1 | 1 | 0 | 0 | 0 | 1 | 1 | 0 | 0 | 0 |
| GFAP | 0 | 0 | 0 | 0 | 0 | 0 | 0 | 0 | 0 | 0 |
| A2B5 | 1 | 1 | 1 | 1 | 1 | 1 | 1 | 1 | 1 | 1 |
| βIIItub | 1 | 1 | 1 | 1 | 1 | 1 | 1 | 1 | 0 | 1 |
| MAP2 | 0 | 0 | 0 | 0 | 1 | 0 | 0 | 1 | 0 | 1 |
| NF 311 | 0 | 0 | 0 | 0 | 1 | 0 | 0 | 0 | 0 | 1 |
| NF-P | 1 | 1 | 1 | 1 | 1 | 1 | 1 | 1 | 1 | 1 |
| RARb | 1 | 1 | 1 | 1 | 1 | 0 | 1 | 1 | 1 | 1 |
| RXRa | 1 | 1 | 1 | 1 | 1 | 1 | 0 | 1 | 1 | 1 |
| RXRb | 0 | 1 | 1 | 1 | 1 | 0 | 1 | 1 | 1 | 1 |
| desmin | 1 | 1 | 1 | 1 | 0 | 1 | 1 | 1 | 1 | 1 |
| SM-act | 0 | 0 | 0 | 0 | 0 | 0 | 1 | 0 | 1 | 0 |
| crhomogA | 1 | 1 | 1 | 1 | 1 | 1 | 1 | 1 | 1 | 1 |
| GRP | 1 | 1 | 1 | 1 | 1 | 1 | 1 | 1 | 1 | 1 |
| SR | 1 | 1 | 1 | 1 | 1 | 1 | 1 | 1 | 1 | 1 |
| NSE | 1 | 1 | 1 | 1 | 1 | 1 | 1 | 1 | 1 | 1 |

N.B.: The numbers in the top row of the Table refer to different subjects; a value of "1" reflects mRNA expression; and a value of "0" connotes the absence of mRNA expression.

The effect of different external stimuli, such as various growth factors and cytokines and their combinations, on proliferation and differentiation in human NSCLCs was also examined in this example. For this purpose, cells in culture were treated with different biologically active factors that are known to stimulate differentiation or apoptosis. Suitable biologically active factors include a host of cytokines, such as TGF-β1, and different neurotrophic factors such as NGF, BDNF, NT-3, NT-4, alone or in combination. It will be appreciated, however, that any factor that affects cell survival and differentiation may be employed to evaluate the response of tumor subtypes to different treatment protocols. Correlation between the gene expression profile and response in proliferation/differentiation to treatments was identified (Table 16). The data established that certain external signals (GDNF+TGFβ1) resulted in the activation of mixed developmental programs (neurons/astrocytes/oligodendrocytes/smooth muscle cells) in different NSCLCs. O4, CNPase weak immunoreactivity was examined in the same cells that were MAP2+, A2B5, and desmin-positive. These data suggest that such activation of mixed differentiation programs finalizes in the execution of programmed cell death, and this type of a suicidal mechanism (through activation of "too many" developmental programs) as such presents an attractive target for cancer drug therapy.

TABLE 16

Effect of TGFβ1, GDNF and BMP4 on the proliferation of lung tumor cells.

|  | 1 | 2 | 3 | 4 | 5 |
|---|---|---|---|---|---|
| +TGFβ1 | — | — | — | — | — |
| +GDNF | — | 3.0 ± 0.7↑ | — | — | — |
| +GDNF + TGFβ1 | 6.0 ± 1.0↓ | — | — | — | 3.9 ± 0.9↑ |
| +NT-4 | — | — | — | — | — |
| +NT-4 + TGFβ1 | — | 2.6 ± 0.3↑ | — | — | — |
| +BMP-4 | 2.6 ± 0.7↑ | 2.4 ± 0.2↑ | — | — | — |
| +BMP-4 +TGFβ1 | — | — | — | — | — |

Human NSCLC cells were grown for 6 days on laminin-coated 24-well plates in DMEM/F-12 media supplemented with B27 in the presence of TGFβ1 (100 pg/ml), GDNF (100 ng/ml) and BMP4 (100 ng/ml). After 6 days cells were dissociated and cell number determined using hemocytometer. Values represent the relative change (in folds) in cell number normalized to the cell number of untreated cultures. Three independent experiments were performed to assess the changes in cell number. ↑—enhanced proliferation compared to control; ↓—reduced proliferation compared to control.

CONCLUSION

We have discovered that the various neoplastic molecular markers can be used to diagnose and direct the treatment of neoplastic diseases. The forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the invention.

What is claimed is:

1. An array for identifying a neoplastic source sample, comprising a plurality of neoplastic molecular markers arranged in an assayable format, said molecular markers being differentially expressed in a sample obtained from a subject afflicted with small cell lung cancer as compared to a comparable sample obtained from a subject not afflicted with small cell lung cancer;

wherein said neoplastic molecular markers comprise protein markers of NeuroD2, ATH5, Sox1, Sox2, and LMO4; and wherein said protein markers are used to detect the presence of small cell lung cancer.

2. The array of claim 1, wherein said protein markers comprise peptides of NeuroD2, ATH5, Sox1, Sox2, and LMO4.

3. The array of claim 1, wherein said neoplastic molecular markers further comprise at least one protein marker selected from the group consisting of HES2, Isl1, Lhx2, NeuroD1, NGN2, NSCL2, Sharp1, Groucho1, Sox10, Sox11, Sall1, GBX2, and Brn5, or combinations thereof.

* * * * *

SEQUENCE LISTING

```
<160> NUMBER OF SEQ ID NOS: 380

<210> SEQ ID NO 1
<211> LENGTH: 15
<212> TYPE: PRT
<213> ORGANISM: Artificial Sequence
<220> FEATURE:
<223> OTHER INFORMATION: Probe

<400> SEQUENCE: 1

Gln Asp Asp Glu Gln Glu Arg Arg Arg Arg Gly Arg Thr Arg
 1               5                  10                  15

<210> SEQ ID NO 2
<211> LENGTH: 13
<212> TYPE: PRT
<213> ORGANISM: Artificial Sequence
<220> FEATURE:
<223> OTHER INFORMATION: Probe

<400> SEQUENCE: 2

Cys Lys Arg Arg Pro Ser Arg Ser Arg Ala Val Ser Arg
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Probe

<400> SEQUENCE: 3

Gln Arg Arg Ser Arg Arg Lys Lys Ala Asn Asp Arg Glu Arg
 1               5                  10

<210> SEQ ID NO 4
<211> LENGTH: 16
<212> TYPE: PRT
<213> ORGANISM: Artificial Sequence
<220> FEATURE:
<223> OTHER INFORMATION: Probe
```

-continued

```
<400> SEQUENCE: 4

Asp Asp Asp Gln Lys Pro Lys Arg Arg Gly Pro Lys Lys Lys Lys Met
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Probe

<400> SEQUENCE: 5

Gln Asp Ser Ser Pro Asp His Glu Lys Ser Tyr His
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Probe

<400> SEQUENCE: 6

Gly Thr Leu Asp Asn Ser Lys Ser Met Lys Pro
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Probe

<400> SEQUENCE: 7

Ser Phe Asn Asn Asp Lys Lys Leu Ser Lys Tyr Glu Thr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Probe

<400> SEQUENCE: 8

Gly Leu Arg Cys Glu Gln Arg Gly Arg Asp His Pro Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Probe

<400> SEQUENCE: 9

Ala Asp Gly Gln Pro Ser Gly Gly Gly His Lys Ser Ala
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Probe
```

```
<400> SEQUENCE: 10

Pro Thr His Ser Glu Thr Glu Ser Gly Phe Ser Asp Cys Gly Gly Gly
 1               5                  10                  15

Ala

<210> SEQ ID NO 11
<211> LENGTH: 16
<212> TYPE: PRT
<213> ORGANISM: Artificial Sequence
<220> FEATURE:
<223> OTHER INFORMATION: Probe

<400> SEQUENCE: 11

Ala Ala Asp Ser Asp His Pro Ser Ser Ala His Ser Asp Pro Glu Ser
 1               5                  10                  15

<210> SEQ ID NO 12
<211> LENGTH: 11
<212> TYPE: PRT
<213> ORGANISM: Artificial Sequence
<220> FEATURE:
<223> OTHER INFORMATION: Probe

<400> SEQUENCE: 12

Thr Pro Asp Lys Pro Lys Thr Ala Ser Glu His
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Probe

<400> SEQUENCE: 13

Ser Leu Lys Pro Leu Leu Glu Lys Arg Arg Arg Ala Arg
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Probe

<400> SEQUENCE: 14

Arg Arg Glu Gly Ser Thr Thr Asp Ser Ala Asn Pro
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Probe

<400> SEQUENCE: 15

Ser Leu His Gln Asp Tyr Ser Glu Gly Tyr Ser Trp Cys
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Probe
```

```
<400> SEQUENCE: 16

Cys Lys Pro Lys Arg Ser Leu Lys Arg Asp Asp Thr Lys Asp Thr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Probe

<400> SEQUENCE: 17

Val Tyr Lys Ser Arg Arg Gly Ile Lys Arg Ser Glu Asp Ser Lys Glu
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Probe

<400> SEQUENCE: 18

Thr Ala Ser Pro Thr Glu Pro His His Gln Gly Arg Leu Gly
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Probe

<400> SEQUENCE: 19

Ser Pro Gln Gln Thr Ser Ser Gly Thr Asn Asn Lys Pro Tyr Arg Pro
1               5                   10                  15

Trp

<210> SEQ ID NO 20
<211> LENGTH: 14
<212> TYPE: PRT
<213> ORGANISM: Artificial Sequence
<220> FEATURE:
<223> OTHER INFORMATION: Probe

<400> SEQUENCE: 20

Ser Thr Pro Ser Ser Ser Gln Met Gln Ala Arg Lys Lys Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Probe

<400> SEQUENCE: 21

Thr Trp Tyr Gln Asn Arg Arg Thr Lys Trp Lys Arg
1               5                   10

<210> SEQ ID NO 22
<211> LENGTH: 15
<212> TYPE: PRT
<213> ORGANISM: Artificial Sequence
<220> FEATURE:
```

<223> OTHER INFORMATION: Probe

<400> SEQUENCE: 22

Phe Lys Asn Arg Arg Ala Lys Trp Arg Lys Arg Glu Arg Ser Gln
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: Probe

<400> SEQUENCE: 23

Ala Gly His Ser Gln Pro Asp Gly Ala Tyr Ser Ser Ala
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Probe

<400> SEQUENCE: 24

His Gln His Gln Gln Pro Pro Ser Gly Gly Gly Ala Gly Pro Gly Gly
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: Probe

<400> SEQUENCE: 25

His Pro Ser Gln Glu Ser Pro Thr Leu Pro Glu Ser Ser Ala Thr Asp
1               5                   10                  15

Ser

<210> SEQ ID NO 26
<211> LENGTH: 13
<212> TYPE: PRT
<213> ORGANISM: Artificial Sequence
<220> FEATURE:
<223> OTHER INFORMATION: Probe

<400> SEQUENCE: 26

Gly Ser Asp Ser Gln Gln Lys Lys Lys Gly Thr His His
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Probe

<400> SEQUENCE: 27

Pro Arg Thr Arg Lys Leu Lys Lys Lys Lys Asn Glu Lys
1               5                   10

<210> SEQ ID NO 28
<211> LENGTH: 14
<212> TYPE: PRT
<213> ORGANISM: Artificial Sequence

```
<220> FEATURE:
<223> OTHER INFORMATION: Probe

<400> SEQUENCE: 28

Ala Pro Gly Asn His Gln His Pro His Arg Ile Thr Asn Phe
 1               5                  10

<210> SEQ ID NO 29
<211> LENGTH: 16
<212> TYPE: PRT
<213> ORGANISM: Artificial Sequence
<220> FEATURE:
<223> OTHER INFORMATION: Probe

<400> SEQUENCE: 29

Ser Thr Arg Arg Arg Gln Arg Pro Ala Ser Ser Arg Arg Ser Arg Cys
 1               5                  10                  15

<210> SEQ ID NO 30
<211> LENGTH: 13
<212> TYPE: PRT
<213> ORGANISM: Artificial Sequence
<220> FEATURE:
<223> OTHER INFORMATION: Probe

<400> SEQUENCE: 30

Gly Gly Asn Glu Gly Ser Pro Cys Pro Cys Pro Gly
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: Probe

<400> SEQUENCE: 31

Pro Pro Gln Asp Ser Ser Ser Lys Ser Pro Glu Pro Ser
 1               5                  10

<210> SEQ ID NO 32
<211> LENGTH: 15
<212> TYPE: PRT
<213> ORGANISM: Artificial Sequence
<220> FEATURE:
<223> OTHER INFORMATION: Probe

<400> SEQUENCE: 32

Gln Asp Ala Lys Pro Arg Val Arg Arg Glu Gln Gln Thr Cys Val
 1               5                  10                  15

<210> SEQ ID NO 33
<211> LENGTH: 14
<212> TYPE: PRT
<213> ORGANISM: Artificial Sequence
<220> FEATURE:
<223> OTHER INFORMATION: Probe

<400> SEQUENCE: 33

Asp Glu Arg Pro Ala His Lys Asp Gly Pro Thr Glu Ala Ser
 1               5                  10

<210> SEQ ID NO 34
<211> LENGTH: 13
<212> TYPE: PRT
<213> ORGANISM: Artificial Sequence
<220> FEATURE:
```

-continued

<223> OTHER INFORMATION: Probe

<400> SEQUENCE: 34

Pro His Gly Pro Lys Glu Pro Ser Pro Lys His His Thr
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Probe

<400> SEQUENCE: 35

Cys Ser Ser Glu Asp Asp Ser Lys Glu Ser Thr Cys Ser Pro Thr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Probe

<400> SEQUENCE: 36

Gly Ser Ser Gly Lys Lys Ser Asp Ser Ser Arg Asp Asp Glu Ser
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Probe

<400> SEQUENCE: 37

Lys Pro Ser Thr Pro Glu Ser Pro Ala Lys Ser Glu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Probe

<400> SEQUENCE: 38

Leu Arg Pro His Val His Lys Gln Pro Glu Lys Thr Thr Arg
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Probe

<400> SEQUENCE: 39

Arg Asp Gln Pro Tyr Pro Ser Ser Gln Lys Thr Lys Arg Met Arg Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Probe

```
<400> SEQUENCE: 40

Cys Phe Ser Arg Gly Glu Ser Val Tyr Cys Lys Asp Asp Phe Phe
 1               5                  10                  15

<210> SEQ ID NO 41
<211> LENGTH: 17
<212> TYPE: PRT
<213> ORGANISM: Artificial Sequence
<220> FEATURE:
<223> OTHER INFORMATION: Probe

<400> SEQUENCE: 41

Glu Asp Tyr Glu Thr Ala Lys Gln Asn Asp Ser Glu Ala Gly Ala
 1               5                  10                  15

Lys

<210> SEQ ID NO 42
<211> LENGTH: 17
<212> TYPE: PRT
<213> ORGANISM: Artificial Sequence
<220> FEATURE:
<223> OTHER INFORMATION: Probe

<400> SEQUENCE: 42

Pro Leu Gln Asp Asp Pro Lys Glu Thr Asp Asn Ser Thr Ser Ser Asp
 1               5                  10                  15

Lys

<210> SEQ ID NO 43
<211> LENGTH: 13
<212> TYPE: PRT
<213> ORGANISM: Artificial Sequence
<220> FEATURE:
<223> OTHER INFORMATION: Probe

<400> SEQUENCE: 43

Cys Ser Thr Cys Arg Asn Arg Leu Val Pro Gly Asp Arg
 1               5                  10

<210> SEQ ID NO 44
<211> LENGTH: 15
<212> TYPE: PRT
<213> ORGANISM: Artificial Sequence
<220> FEATURE:
<223> OTHER INFORMATION: Probe

<400> SEQUENCE: 44

Asp Asn Gly Ser Phe Leu Arg Arg Arg Lys Arg Phe Lys Arg Gln
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Probe

<400> SEQUENCE: 45

Ser Glu Pro Ser Gly Ser Pro Pro Ala Pro Ala His Ser Arg Ala
 1               5                  10                  15

<210> SEQ ID NO 46
<211> LENGTH: 12
<212> TYPE: PRT
```

```
<213> ORGANISM: Artificial Sequence
<220> FEATURE:
<223> OTHER INFORMATION: Probe

<400> SEQUENCE: 46

Gly Asn Gln Lys Asn Ser Pro Asp Arg Val Lys Arg
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Probe

<400> SEQUENCE: 47

Gln Pro Pro Ser Met Ser Ser Pro Pro Pro Pro Ala
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Probe

<400> SEQUENCE: 48

Lys Lys Asp His Pro Asp Tyr Lys Tyr Gln Pro Arg Arg Arg Lys Asn
1               5                   10                  15
Gly

<210> SEQ ID NO 49
<211> LENGTH: 14
<212> TYPE: PRT
<213> ORGANISM: Artificial Sequence
<220> FEATURE:
<223> OTHER INFORMATION: Probe

<400> SEQUENCE: 49

Asp Tyr Pro Asp Tyr Lys Tyr Arg Pro Arg Lys Lys Pro Lys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Probe

<400> SEQUENCE: 50

Ala Ser Gln Ser Tyr Ser Tyr His Ser Ser Gly Glu Tyr Ser
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Probe

<400> SEQUENCE: 51

Asp Gly Asp Thr Glu Lys Gly Gln Pro Ser Arg Pro Thr Lys Ser Lys
1               5                   10                  15
Asp
```

<210> SEQ ID NO 52
<211> LENGTH: 14
<212> TYPE: PRT
<213> ORGANISM: Artificial Sequence
<220> FEATURE:
<223> OTHER INFORMATION: Probe

<400> SEQUENCE: 52

Pro Asp Ser Leu Asp Gln Pro Gln Pro Met Glu Gln Gly Ser
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Probe

<400> SEQUENCE: 53

Gly Tyr Ala Asp Ser Pro Ser Ala Thr Pro Ala Ser Arg Ser Pro Gln
1               5                   10                  15

Arg

<210> SEQ ID NO 54
<211> LENGTH: 14
<212> TYPE: PRT
<213> ORGANISM: Artificial Sequence
<220> FEATURE:
<223> OTHER INFORMATION: Probe

<400> SEQUENCE: 54

Ser Pro Ser Thr Asp Asn Pro Thr Thr Ser Ser Leu Ser Pro
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Probe

<400> SEQUENCE: 55

Asn Ser Lys Asp Thr Thr Lys Thr Pro Ser Ala
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Probe

<400> SEQUENCE: 56

Lys Pro Ser Gln Lys Lys Gln Ser Leu Lys Asn Thr Asp
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Probe

<400> SEQUENCE: 57

Asp Asp Lys Lys His His Asp Ala Glu His His Arg Asp Arg Glu Pro
1               5                   10                  15

-continued

Gly Thr

<210> SEQ ID NO 58
<211> LENGTH: 16
<212> TYPE: PRT
<213> ORGANISM: Artificial Sequence
<220> FEATURE:
<223> OTHER INFORMATION: Probe

<400> SEQUENCE: 58

Lys Glu Pro Ser Gly Pro Tyr Glu Ser Asp Glu Asp Lys Ser Asp Tyr
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Probe

<400> SEQUENCE: 59

Ser Thr Pro Ser Ser Lys Thr Lys Asp Leu Gly His Asn Asp Lys Ser
1               5                   10                  15

Ser

<210> SEQ ID NO 60
<211> LENGTH: 14
<212> TYPE: PRT
<213> ORGANISM: Artificial Sequence
<220> FEATURE:
<223> OTHER INFORMATION: Probe

<400> SEQUENCE: 60

Asp Tyr Ser Ser Glu Ser Lys Lys Gln Lys Thr Glu Glu Lys
1               5                   10

<210> SEQ ID NO 61
<211> LENGTH: 24
<212> TYPE: DNA
<213> ORGANISM: Artificial Sequence
<220> FEATURE:
<223> OTHER INFORMATION: Probe

<400> SEQUENCE: 61
gagcgcagcc ttagtaggag agga                                          24

<210> SEQ ID NO 62
<211> LENGTH: 24
<212> TYPE: DNA
<213> ORGANISM: Artificial Sequence
<220> FEATURE:
<223> OTHER INFORMATION: Probe

<400> SEQUENCE: 62
ccctctctgt tcctgcaccc aagt                                          24

<210> SEQ ID NO 63
<211> LENGTH: 27
<212> TYPE: DNA
<213> ORGANISM: Artificial Sequence
<220> FEATURE:
<223> OTHER INFORMATION: Probe

<400> SEQUENCE: 63
ccagcatgga aagctctgcc aagatgg                                       27

```
<210> SEQ ID NO 64
<211> LENGTH: 25
<212> TYPE: DNA
<213> ORGANISM: Artificial Sequence
<220> FEATURE:
<223> OTHER INFORMATION: Probe

<400> SEQUENCE: 64
gacttgcttg ggcgctgact tgtga                                        25

<210> SEQ ID NO 65
<211> LENGTH: 26
<212> TYPE: DNA
<213> ORGANISM: Artificial Sequence
<220> FEATURE:
<223> OTHER INFORMATION: Probe

<400> SEQUENCE: 65
gagcgcagtg tctccacctt actcat                                       26

<210> SEQ ID NO 66
<211> LENGTH: 26
<212> TYPE: DNA
<213> ORGANISM: Artificial Sequence
<220> FEATURE:
<223> OTHER INFORMATION: Probe

<400> SEQUENCE: 66
ccagttggtg aagtcgagaa gctcct                                       26

<210> SEQ ID NO 67
<211> LENGTH: 25
<212> TYPE: DNA
<213> ORGANISM: Artificial Sequence
<220> FEATURE:
<223> OTHER INFORMATION: Probe

<400> SEQUENCE: 67
ctccattggc tgagaagaca cgcga                                        25

<210> SEQ ID NO 68
<211> LENGTH: 26
<212> TYPE: DNA
<213> ORGANISM: Artificial Sequence
<220> FEATURE:
<223> OTHER INFORMATION: Probe

<400> SEQUENCE: 68
gcgtccgagc ctttgcagtg caatgt                                       26

<210> SEQ ID NO 69
<211> LENGTH: 25
<212> TYPE: DNA
<213> ORGANISM: Artificial Sequence
<220> FEATURE:
<223> OTHER INFORMATION: Probe

<400> SEQUENCE: 69
ctccttccta acttgcctca tccga                                        25

<210> SEQ ID NO 70
<211> LENGTH: 24
<212> TYPE: DNA
<213> ORGANISM: Artificial Sequence
<220> FEATURE:
<223> OTHER INFORMATION: Probe
```

```
<400> SEQUENCE: 70
gtagcagctc ggacaaggcg ttga                                          24

<210> SEQ ID NO 71
<211> LENGTH: 28
<212> TYPE: DNA
<213> ORGANISM: Artificial Sequence
<220> FEATURE:
<223> OTHER INFORMATION: Probe

<400> SEQUENCE: 71
ccaccatgaa gtcggcctgc aaaccccca                                     28

<210> SEQ ID NO 72
<211> LENGTH: 24
<212> TYPE: DNA
<213> ORGANISM: Artificial Sequence
<220> FEATURE:
<223> OTHER INFORMATION: Probe

<400> SEQUENCE: 72
catggggaag ggctccggct ggaa                                          24

<210> SEQ ID NO 73
<211> LENGTH: 27
<212> TYPE: DNA
<213> ORGANISM: Artificial Sequence
<220> FEATURE:
<223> OTHER INFORMATION: Probe

<400> SEQUENCE: 73
ccaccatgta gaaatgacag caatgga                                       27

<210> SEQ ID NO 74
<211> LENGTH: 23
<212> TYPE: DNA
<213> ORGANISM: Artificial Sequence
<220> FEATURE:
<223> OTHER INFORMATION: Probe

<400> SEQUENCE: 74
gatggggttg gacaaagggt tga                                           23

<210> SEQ ID NO 75
<211> LENGTH: 24
<212> TYPE: DNA
<213> ORGANISM: Artificial Sequence
<220> FEATURE:
<223> OTHER INFORMATION: Probe

<400> SEQUENCE: 75
catgatcgac gagatcctct ccaa                                          24

<210> SEQ ID NO 76
<211> LENGTH: 25
<212> TYPE: DNA
<213> ORGANISM: Artificial Sequence
<220> FEATURE:
<223> OTHER INFORMATION: Probe

<400> SEQUENCE: 76
ggttccgaag agggtattgg caact                                         25

<210> SEQ ID NO 77
```

<211> LENGTH: 27
<212> TYPE: DNA
<213> ORGANISM: Artificial Sequence
<220> FEATURE:
<223> OTHER INFORMATION: Probe

<400> SEQUENCE: 77
gcgctatgac cctgagcacg gagatgt           27

<210> SEQ ID NO 78
<211> LENGTH: 25
<212> TYPE: DNA
<213> ORGANISM: Artificial Sequence
<220> FEATURE:
<223> OTHER INFORMATION: Probe

<400> SEQUENCE: 78
ggcgcgctaa cgacgttcct aacaa             25

<210> SEQ ID NO 79
<211> LENGTH: 24
<212> TYPE: DNA
<213> ORGANISM: Artificial Sequence
<220> FEATURE:
<223> OTHER INFORMATION: Probe

<400> SEQUENCE: 79
cggtccttgc gccaggtcct ttga              24

<210> SEQ ID NO 80
<211> LENGTH: 26
<212> TYPE: DNA
<213> ORGANISM: Artificial Sequence
<220> FEATURE:
<223> OTHER INFORMATION: Probe

<400> SEQUENCE: 80
gtactagcga cacccacaac cctcca            26

<210> SEQ ID NO 81
<211> LENGTH: 24
<212> TYPE: DNA
<213> ORGANISM: Artificial Sequence
<220> FEATURE:
<223> OTHER INFORMATION: Probe

<400> SEQUENCE: 81
cgacgcggac atggtcatga gctt              24

<210> SEQ ID NO 82
<211> LENGTH: 25
<212> TYPE: DNA
<213> ORGANISM: Artificial Sequence
<220> FEATURE:
<223> OTHER INFORMATION: Probe

<400> SEQUENCE: 82
ccccagcatc tggtttcgag ttagt             25

<210> SEQ ID NO 83
<211> LENGTH: 24
<212> TYPE: DNA
<213> ORGANISM: Artificial Sequence
<220> FEATURE:
<223> OTHER INFORMATION: Probe

<400> SEQUENCE: 83

```
cgagagtcat ggcgaccgca gcgt                                              24

<210> SEQ ID NO 84
<211> LENGTH: 24
<212> TYPE: DNA
<213> ORGANISM: Artificial Sequence
<220> FEATURE:
<223> OTHER INFORMATION: Probe

<400> SEQUENCE: 84
ccgtgaagct gggctgcgag taga                                              24

<210> SEQ ID NO 85
<211> LENGTH: 23
<212> TYPE: DNA
<213> ORGANISM: Artificial Sequence
<220> FEATURE:
<223> OTHER INFORMATION: Probe

<400> SEQUENCE: 85
accatggcca cagctgcctc gaa                                               23

<210> SEQ ID NO 86
<211> LENGTH: 25
<212> TYPE: DNA
<213> ORGANISM: Artificial Sequence
<220> FEATURE:
<223> OTHER INFORMATION: Probe

<400> SEQUENCE: 86
cggagtgatc ctggcaatgg tgcga                                             25

<210> SEQ ID NO 87
<211> LENGTH: 22
<212> TYPE: DNA
<213> ORGANISM: Artificial Sequence
<220> FEATURE:
<223> OTHER INFORMATION: Probe

<400> SEQUENCE: 87
cctcgcttcc tccagtcaga ga                                                22

<210> SEQ ID NO 88
<211> LENGTH: 24
<212> TYPE: DNA
<213> ORGANISM: Artificial Sequence
<220> FEATURE:
<223> OTHER INFORMATION: Probe

<400> SEQUENCE: 88
cattaccagc gccattccca gcat                                              24

<210> SEQ ID NO 89
<211> LENGTH: 24
<212> TYPE: DNA
<213> ORGANISM: Artificial Sequence
<220> FEATURE:
<223> OTHER INFORMATION: Probe

<400> SEQUENCE: 89
cggtcgtagt tgagctcctt agca                                              24

<210> SEQ ID NO 90
<211> LENGTH: 25
<212> TYPE: DNA
```

<213> ORGANISM: Artificial Sequence
<220> FEATURE:
<223> OTHER INFORMATION: Probe

<400> SEQUENCE: 90
gagcgtgtat cctgggccgt ctagt                                          25

<210> SEQ ID NO 91
<211> LENGTH: 26
<212> TYPE: DNA
<213> ORGANISM: Artificial Sequence
<220> FEATURE:
<223> OTHER INFORMATION: Probe

<400> SEQUENCE: 91
cagagtcact ttgcsccgag cctcca                                         26

<210> SEQ ID NO 92
<211> LENGTH: 24
<212> TYPE: DNA
<213> ORGANISM: Artificial Sequence
<220> FEATURE:
<223> OTHER INFORMATION: Probe

<400> SEQUENCE: 92
gaccttcagt gccatcctga ctct                                           24

<210> SEQ ID NO 93
<211> LENGTH: 24
<212> TYPE: DNA
<213> ORGANISM: Artificial Sequence
<220> FEATURE:
<223> OTHER INFORMATION: Probe

<400> SEQUENCE: 93
gtgcaggtga cagtgggtat ccaa                                           24

<210> SEQ ID NO 94
<211> LENGTH: 24
<212> TYPE: DNA
<213> ORGANISM: Artificial Sequence
<220> FEATURE:
<223> OTHER INFORMATION: Probe

<400> SEQUENCE: 94
ggcagcatcc aaggcagatg aagt                                           24

<210> SEQ ID NO 95
<211> LENGTH: 24
<212> TYPE: DNA
<213> ORGANISM: Artificial Sequence
<220> FEATURE:
<223> OTHER INFORMATION: Probe

<400> SEQUENCE: 95
ctccttgccc ttcaccgtga gctt                                           24

<210> SEQ ID NO 96
<211> LENGTH: 27
<212> TYPE: DNA
<213> ORGANISM: Artificial Sequence
<220> FEATURE:
<223> OTHER INFORMATION: Probe

<400> SEQUENCE: 96
ggagatgacc atgaccacca tgccaga                                        27

<210> SEQ ID NO 97
<211> LENGTH: 24
<212> TYPE: DNA
<213> ORGANISM: Artificial Sequence
<220> FEATURE:
<223> OTHER INFORMATION: Probe

<400> SEQUENCE: 97
cacatcagtt gaggctgctg cata                                          24

<210> SEQ ID NO 98
<211> LENGTH: 26
<212> TYPE: DNA
<213> ORGANISM: Artificial Sequence
<220> FEATURE:
<223> OTHER INFORMATION: Probe

<400> SEQUENCE: 98
gtggctgata tgcactcgac ccagat                                        26

<210> SEQ ID NO 99
<211> LENGTH: 27
<212> TYPE: DNA
<213> ORGANISM: Artificial Sequence
<220> FEATURE:
<223> OTHER INFORMATION: Probe

<400> SEQUENCE: 99
cttggaccgg cggttctgga accagat                                       27

<210> SEQ ID NO 100
<211> LENGTH: 31
<212> TYPE: DNA
<213> ORGANISM: Artificial Sequence
<220> FEATURE:
<223> OTHER INFORMATION: Probe

<400> SEQUENCE: 100
ccgccatgac aggagtgttt gacagaaggg t                                  31

<210> SEQ ID NO 101
<211> LENGTH: 23
<212> TYPE: DNA
<213> ORGANISM: Artificial Sequence
<220> FEATURE:
<223> OTHER INFORMATION: Probe

<400> SEQUENCE: 101
ctaatagagt gtcccggagg cca                                           23

<210> SEQ ID NO 102
<211> LENGTH: 26
<212> TYPE: DNA
<213> ORGANISM: Artificial Sequence
<220> FEATURE:
<223> OTHER INFORMATION: Probe

<400> SEQUENCE: 102
cagcacctaa accagcgttt ccagca                                        26

<210> SEQ ID NO 103
<211> LENGTH: 25
<212> TYPE: DNA
<213> ORGANISM: Artificial Sequence
<220> FEATURE:

```
<223> OTHER INFORMATION: Probe

<400> SEQUENCE: 103
catcatctga ggcgaagcca ggaca                                            25

<210> SEQ ID NO 104
<211> LENGTH: 24
<212> TYPE: DNA
<213> ORGANISM: Artificial Sequence
<220> FEATURE:
<223> OTHER INFORMATION: Probe

<400> SEQUENCE: 104
cgtgttcccc gaggccatga acca                                             24

<210> SEQ ID NO 105
<211> LENGTH: 24
<212> TYPE: DNA
<213> ORGANISM: Artificial Sequence
<220> FEATURE:
<223> OTHER INFORMATION: Probe

<400> SEQUENCE: 105
gatgtcctcc ccattggcct gctt                                             24

<210> SEQ ID NO 106
<211> LENGTH: 25
<212> TYPE: DNA
<213> ORGANISM: Artificial Sequence
<220> FEATURE:
<223> OTHER INFORMATION: Probe

<400> SEQUENCE: 106
cacaccccct attcgcctcg cagca                                            25

<210> SEQ ID NO 107
<211> LENGTH: 28
<212> TYPE: DNA
<213> ORGANISM: Artificial Sequence
<220> FEATURE:
<223> OTHER INFORMATION: Probe

<400> SEQUENCE: 107
ctatttcctc cggactcgcc tgcttggt                                         28

<210> SEQ ID NO 108
<211> LENGTH: 25
<212> TYPE: DNA
<213> ORGANISM: Artificial Sequence
<220> FEATURE:
<223> OTHER INFORMATION: Probe

<400> SEQUENCE: 108
cgagcatgga agaacagcag ccgga                                            25

<210> SEQ ID NO 109
<211> LENGTH: 25
<212> TYPE: DNA
<213> ORGANISM: Artificial Sequence
<220> FEATURE:
<223> OTHER INFORMATION: Probe

<400> SEQUENCE: 109
ggctactcgc tctcgtcttt gtcct                                            25
```

<210> SEQ ID NO 110
<211> LENGTH: 25
<212> TYPE: DNA
<213> ORGANISM: Artificial Sequence
<220> FEATURE:
<223> OTHER INFORMATION: Probe

<400> SEQUENCE: 110
ccagcatgga ggagaatgac cccaa                                               25

<210> SEQ ID NO 111
<211> LENGTH: 24
<212> TYPE: DNA
<213> ORGANISM: Artificial Sequence
<220> FEATURE:
<223> OTHER INFORMATION: Probe

<400> SEQUENCE: 111
cctactcgct gtccgacttg ccct                                                24

<210> SEQ ID NO 112
<211> LENGTH: 24
<212> TYPE: DNA
<213> ORGANISM: Artificial Sequence
<220> FEATURE:
<223> OTHER INFORMATION: Probe

<400> SEQUENCE: 112
gggatcacac tgagcttgcc acat                                                24

<210> SEQ ID NO 113
<211> LENGTH: 25
<212> TYPE: DNA
<213> ORGANISM: Artificial Sequence
<220> FEATURE:
<223> OTHER INFORMATION: Probe

<400> SEQUENCE: 113
cccaggttaa tccccagagg ctcca                                               25

<210> SEQ ID NO 114
<211> LENGTH: 26
<212> TYPE: DNA
<213> ORGANISM: Artificial Sequence
<220> FEATURE:
<223> OTHER INFORMATION: Probe

<400> SEQUENCE: 114
catgagctga gcggagccac cacagt                                              26

<210> SEQ ID NO 115
<211> LENGTH: 24
<212> TYPE: DNA
<213> ORGANISM: Artificial Sequence
<220> FEATURE:
<223> OTHER INFORMATION: Probe

<400> SEQUENCE: 115
caatcacctc gactcgcagg gcaa                                                24

<210> SEQ ID NO 116
<211> LENGTH: 26
<212> TYPE: DNA
<213> ORGANISM: Artificial Sequence
<220> FEATURE:
<223> OTHER INFORMATION: Probe

```
<400> SEQUENCE: 116
gaggccacag gcattgcaca ggtagt                                    26

<210> SEQ ID NO 117
<211> LENGTH: 24
<212> TYPE: DNA
<213> ORGANISM: Artificial Sequence
<220> FEATURE:
<223> OTHER INFORMATION: Probe

<400> SEQUENCE: 117
gagcacagcc gaggccatgg aggt                                      24

<210> SEQ ID NO 118
<211> LENGTH: 24
<212> TYPE: DNA
<213> ORGANISM: Artificial Sequence
<220> FEATURE:
<223> OTHER INFORMATION: Probe

<400> SEQUENCE: 118
ccttgggcct ggacttgcat ccga                                      24

<210> SEQ ID NO 119
<211> LENGTH: 26
<212> TYPE: DNA
<213> ORGANISM: Artificial Sequence
<220> FEATURE:
<223> OTHER INFORMATION: Probe

<400> SEQUENCE: 119
ctggcctcta ccgagcgcgt ctatga                                    26

<210> SEQ ID NO 120
<211> LENGTH: 25
<212> TYPE: DNA
<213> ORGANISM: Artificial Sequence
<220> FEATURE:
<223> OTHER INFORMATION: Probe

<400> SEQUENCE: 120
ggagtagcac cgccttcagc ataga                                     25

<210> SEQ ID NO 121
<211> LENGTH: 24
<212> TYPE: DNA
<213> ORGANISM: Artificial Sequence
<220> FEATURE:
<223> OTHER INFORMATION: Probe

<400> SEQUENCE: 121
gattgtcatc cgagctgtag tcca                                      24

<210> SEQ ID NO 122
<211> LENGTH: 23
<212> TYPE: DNA
<213> ORGANISM: Artificial Sequence
<220> FEATURE:
<223> OTHER INFORMATION: Probe

<400> SEQUENCE: 122
gccctggccc ttctggaccc tca                                       23

<210> SEQ ID NO 123
<211> LENGTH: 23
```

```
<212> TYPE: DNA
<213> ORGANISM: Artificial Sequence
<220> FEATURE:
<223> OTHER INFORMATION: Probe

<400> SEQUENCE: 123
ccatctacat aatgaatccc agt                                           23

<210> SEQ ID NO 124
<211> LENGTH: 22
<212> TYPE: DNA
<213> ORGANISM: Artificial Sequence
<220> FEATURE:
<223> OTHER INFORMATION: Probe

<400> SEQUENCE: 124
gtggaggtaa acttcggcag ta                                            22

<210> SEQ ID NO 125
<211> LENGTH: 24
<212> TYPE: DNA
<213> ORGANISM: Artificial Sequence
<220> FEATURE:
<223> OTHER INFORMATION: Probe

<400> SEQUENCE: 125
gaccaagaag cgggcactgt ccat                                          24

<210> SEQ ID NO 126
<211> LENGTH: 26
<212> TYPE: DNA
<213> ORGANISM: Artificial Sequence
<220> FEATURE:
<223> OTHER INFORMATION: Probe

<400> SEQUENCE: 126
gcgtgagtat gacttccggc accctt                                        26

<210> SEQ ID NO 127
<211> LENGTH: 25
<212> TYPE: DNA
<213> ORGANISM: Artificial Sequence
<220> FEATURE:
<223> OTHER INFORMATION: Probe

<400> SEQUENCE: 127
ctcacctcca tcaatgccac gccca                                         25

<210> SEQ ID NO 128
<211> LENGTH: 24
<212> TYPE: DNA
<213> ORGANISM: Artificial Sequence
<220> FEATURE:
<223> OTHER INFORMATION: Probe

<400> SEQUENCE: 128
ccaccagcat gtactgcgcc ttga                                          24

<210> SEQ ID NO 129
<211> LENGTH: 25
<212> TYPE: DNA
<213> ORGANISM: Artificial Sequence
<220> FEATURE:
<223> OTHER INFORMATION: Probe

<400> SEQUENCE: 129
```
gcagctcttc agcaagtggc tccta					25

<210> SEQ ID NO 130
<211> LENGTH: 24
<212> TYPE: DNA
<213> ORGANISM: Artificial Sequence
<220> FEATURE:
<223> OTHER INFORMATION: Probe

<400> SEQUENCE: 130
ctctcttgag cagtccagcc acct					24

<210> SEQ ID NO 131
<211> LENGTH: 28
<212> TYPE: DNA
<213> ORGANISM: Artificial Sequence
<220> FEATURE:
<223> OTHER INFORMATION: Probe

<400> SEQUENCE: 131
ccaccatgac cacctcagca agttccca					28

<210> SEQ ID NO 132
<211> LENGTH: 24
<212> TYPE: DNA
<213> ORGANISM: Artificial Sequence
<220> FEATURE:
<223> OTHER INFORMATION: Probe

<400> SEQUENCE: 132
cgatgtccct gccataggct ctgt					24

<210> SEQ ID NO 133
<211> LENGTH: 24
<212> TYPE: DNA
<213> ORGANISM: Artificial Sequence
<220> FEATURE:
<223> OTHER INFORMATION: Probe

<400> SEQUENCE: 133
ccgaaatgca gaggcactat gtga					24

<210> SEQ ID NO 134
<211> LENGTH: 24
<212> TYPE: DNA
<213> ORGANISM: Artificial Sequence
<220> FEATURE:
<223> OTHER INFORMATION: Probe

<400> SEQUENCE: 134
cggagaagaa gggtcctcat taga					24

<210> SEQ ID NO 135
<211> LENGTH: 25
<212> TYPE: DNA
<213> ORGANISM: Artificial Sequence
<220> FEATURE:
<223> OTHER INFORMATION: Probe

<400> SEQUENCE: 135
gcaggatgta cccccaggga aggca					25

<210> SEQ ID NO 136
<211> LENGTH: 25
<212> TYPE: DNA
<213> ORGANISM: Artificial Sequence

```
<220> FEATURE:
<223> OTHER INFORMATION: Probe

<400> SEQUENCE: 136
cctcagggcg acgctgtccg tggaa                                          25

<210> SEQ ID NO 137
<211> LENGTH: 23
<212> TYPE: DNA
<213> ORGANISM: Artificial Sequence
<220> FEATURE:
<223> OTHER INFORMATION: Probe

<400> SEQUENCE: 137
ccaccatgta tccgcagggc aga                                            23

<210> SEQ ID NO 138
<211> LENGTH: 24
<212> TYPE: DNA
<213> ORGANISM: Artificial Sequence
<220> FEATURE:
<223> OTHER INFORMATION: Probe

<400> SEQUENCE: 138
cgctcatctg gggtgggatg ttgt                                           24

<210> SEQ ID NO 139
<211> LENGTH: 24
<212> TYPE: DNA
<213> ORGANISM: Artificial Sequence
<220> FEATURE:
<223> OTHER INFORMATION: Probe

<400> SEQUENCE: 139
cagagatgca gcggcattat gtca                                           24

<210> SEQ ID NO 140
<211> LENGTH: 25
<212> TYPE: DNA
<213> ORGANISM: Artificial Sequence
<220> FEATURE:
<223> OTHER INFORMATION: Probe

<400> SEQUENCE: 140
gtactgccat tggggtcctt aggct                                          25

<210> SEQ ID NO 141
<211> LENGTH: 25
<212> TYPE: DNA
<213> ORGANISM: Artificial Sequence
<220> FEATURE:
<223> OTHER INFORMATION: Probe

<400> SEQUENCE: 141
ggaaaatgcc agctgatata atgga                                          25

<210> SEQ ID NO 142
<211> LENGTH: 24
<212> TYPE: DNA
<213> ORGANISM: Artificial Sequence
<220> FEATURE:
<223> OTHER INFORMATION: Probe

<400> SEQUENCE: 142
ctaccccagc cagtgtcaac acga                                           24
```

<210> SEQ ID NO 143
<211> LENGTH: 26
<212> TYPE: DNA
<213> ORGANISM: Artificial Sequence
<220> FEATURE:
<223> OTHER INFORMATION: Probe

<400> SEQUENCE: 143
gttccgccac ggcctccaca tggagt                                         26

<210> SEQ ID NO 144
<211> LENGTH: 34
<212> TYPE: DNA
<213> ORGANISM: Artificial Sequence
<220> FEATURE:
<223> OTHER INFORMATION: Probe

<400> SEQUENCE: 144
ccaccatgaa gagcctgaag ccgctgctgg agaa                                34

<210> SEQ ID NO 145
<211> LENGTH: 24
<212> TYPE: DNA
<213> ORGANISM: Artificial Sequence
<220> FEATURE:
<223> OTHER INFORMATION: Probe

<400> SEQUENCE: 145
gagcctgaag ccgctgctgg agaa                                           24

<210> SEQ ID NO 146
<211> LENGTH: 24
<212> TYPE: DNA
<213> ORGANISM: Artificial Sequence
<220> FEATURE:
<223> OTHER INFORMATION: Probe

<400> SEQUENCE: 146
ccgctctccg ccacaggtgc tcca                                           24

<210> SEQ ID NO 147
<211> LENGTH: 24
<212> TYPE: DNA
<213> ORGANISM: Artificial Sequence
<220> FEATURE:
<223> OTHER INFORMATION: Probe

<400> SEQUENCE: 147
gcccaccgat ctccaagcct ctga                                           24

<210> SEQ ID NO 148
<211> LENGTH: 24
<212> TYPE: DNA
<213> ORGANISM: Artificial Sequence
<220> FEATURE:
<223> OTHER INFORMATION: Probe

<400> SEQUENCE: 148
ctacgtctca ccacggtcgc caca                                           24

<210> SEQ ID NO 149
<211> LENGTH: 26
<212> TYPE: DNA
<213> ORGANISM: Artificial Sequence
<220> FEATURE:
<223> OTHER INFORMATION: Probe

<400> SEQUENCE: 149
gtggagatgc tcagtcccaa ggagaa                                          26

<210> SEQ ID NO 150
<211> LENGTH: 26
<212> TYPE: DNA
<213> ORGANISM: Artificial Sequence
<220> FEATURE:
<223> OTHER INFORMATION: Probe

<400> SEQUENCE: 150
ccgctggaag tggtaaagca gcttca                                          26

<210> SEQ ID NO 151
<211> LENGTH: 30
<212> TYPE: DNA
<213> ORGANISM: Artificial Sequence
<220> FEATURE:
<223> OTHER INFORMATION: Probe

<400> SEQUENCE: 151
ccagcatgaa gcgagctcac cccgagtaca                                      30

<210> SEQ ID NO 152
<211> LENGTH: 24
<212> TYPE: DNA
<213> ORGANISM: Artificial Sequence
<220> FEATURE:
<223> OTHER INFORMATION: Probe

<400> SEQUENCE: 152
ggacagcgag ctggacgaga ccat                                            24

<210> SEQ ID NO 153
<211> LENGTH: 24
<212> TYPE: DNA
<213> ORGANISM: Artificial Sequence
<220> FEATURE:
<223> OTHER INFORMATION: Probe

<400> SEQUENCE: 153
ggctcagtgc attgggagac agta                                            24

<210> SEQ ID NO 154
<211> LENGTH: 25
<212> TYPE: DNA
<213> ORGANISM: Artificial Sequence
<220> FEATURE:
<223> OTHER INFORMATION: Probe

<400> SEQUENCE: 154
ccctccctca ttctacatca gttct                                           25

<210> SEQ ID NO 155
<211> LENGTH: 26
<212> TYPE: DNA
<213> ORGANISM: Artificial Sequence
<220> FEATURE:
<223> OTHER INFORMATION: Probe

<400> SEQUENCE: 155
gacctccgag agcgacatgg acgaga                                          26

<210> SEQ ID NO 156

```
<211> LENGTH: 24
<212> TYPE: DNA
<213> ORGANISM: Artificial Sequence
<220> FEATURE:
<223> OTHER INFORMATION: Probe

<400> SEQUENCE: 156
ggctactttg acgcacacgc tctt                                              24

<210> SEQ ID NO 157
<211> LENGTH: 25
<212> TYPE: DNA
<213> ORGANISM: Artificial Sequence
<220> FEATURE:
<223> OTHER INFORMATION: Probe

<400> SEQUENCE: 157
cactgctggt ctgctgagga ctgga                                             25

<210> SEQ ID NO 158
<211> LENGTH: 25
<212> TYPE: DNA
<213> ORGANISM: Artificial Sequence
<220> FEATURE:
<223> OTHER INFORMATION: Probe

<400> SEQUENCE: 158
ccaacttctg tcccccaggg tcggt                                             25

<210> SEQ ID NO 159
<211> LENGTH: 23
<212> TYPE: DNA
<213> ORGANISM: Artificial Sequence
<220> FEATURE:
<223> OTHER INFORMATION: Probe

<400> SEQUENCE: 159
catgaagcga cccaaggagc cga                                               23

<210> SEQ ID NO 160
<211> LENGTH: 25
<212> TYPE: DNA
<213> ORGANISM: Artificial Sequence
<220> FEATURE:
<223> OTHER INFORMATION: Probe

<400> SEQUENCE: 160
cagctcagaa agccccgatt tcagt                                             25

<210> SEQ ID NO 161
<211> LENGTH: 23
<212> TYPE: DNA
<213> ORGANISM: Artificial Sequence
<220> FEATURE:
<223> OTHER INFORMATION: Probe

<400> SEQUENCE: 161
cggctgctac gaggcggtgt gct                                               23

<210> SEQ ID NO 162
<211> LENGTH: 23
<212> TYPE: DNA
<213> ORGANISM: Artificial Sequence
<220> FEATURE:
<223> OTHER INFORMATION: Probe

<400> SEQUENCE: 162
```
ggagtgagct cggctgtctg gat                                          23

<210> SEQ ID NO 163
<211> LENGTH: 26
<212> TYPE: DNA
<213> ORGANISM: Artificial Sequence
<220> FEATURE:
<223> OTHER INFORMATION: Probe

<400> SEQUENCE: 163
accggtcgtt ccgatggcag tggaga                                       26

<210> SEQ ID NO 164
<211> LENGTH: 24
<212> TYPE: DNA
<213> ORGANISM: Artificial Sequence
<220> FEATURE:
<223> OTHER INFORMATION: Probe

<400> SEQUENCE: 164
cgtcgttctt ctccaggtca atgt                                         24

<210> SEQ ID NO 165
<211> LENGTH: 23
<212> TYPE: DNA
<213> ORGANISM: Artificial Sequence
<220> FEATURE:
<223> OTHER INFORMATION: Probe

<400> SEQUENCE: 165
cgcgttaaat gtcggacata cct                                          23

<210> SEQ ID NO 166
<211> LENGTH: 25
<212> TYPE: DNA
<213> ORGANISM: Artificial Sequence
<220> FEATURE:
<223> OTHER INFORMATION: Probe

<400> SEQUENCE: 166
cagccaccat gtccttccca cactt                                        25

<210> SEQ ID NO 167
<211> LENGTH: 25
<212> TYPE: DNA
<213> ORGANISM: Artificial Sequence
<220> FEATURE:
<223> OTHER INFORMATION: Probe

<400> SEQUENCE: 167
gaactaggat gaggagagag ccgat                                        25

<210> SEQ ID NO 168
<211> LENGTH: 24
<212> TYPE: DNA
<213> ORGANISM: Artificial Sequence
<220> FEATURE:
<223> OTHER INFORMATION: Probe

<400> SEQUENCE: 168
ccgagatgga ccgcagggcc aaga                                         24

<210> SEQ ID NO 169
<211> LENGTH: 24
<212> TYPE: DNA

```
<213> ORGANISM: Artificial Sequence
<220> FEATURE:
<223> OTHER INFORMATION: Probe

<400> SEQUENCE: 169
gtggggtgag gggttgcgag tcat                                              24

<210> SEQ ID NO 170
<211> LENGTH: 25
<212> TYPE: DNA
<213> ORGANISM: Artificial Sequence
<220> FEATURE:
<223> OTHER INFORMATION: Probe

<400> SEQUENCE: 170
gaaccatgga ggcgcgcggg gagct                                             25

<210> SEQ ID NO 171
<211> LENGTH: 27
<212> TYPE: DNA
<213> ORGANISM: Artificial Sequence
<220> FEATURE:
<223> OTHER INFORMATION: Probe

<400> SEQUENCE: 171
gtcagaactg agcgtggtct acctcat                                           27

<210> SEQ ID NO 172
<211> LENGTH: 28
<212> TYPE: DNA
<213> ORGANISM: Artificial Sequence
<220> FEATURE:
<223> OTHER INFORMATION: Probe

<400> SEQUENCE: 172
gacgatgcaa cagattcccc agtgtgct                                          28

<210> SEQ ID NO 173
<211> LENGTH: 26
<212> TYPE: DNA
<213> ORGANISM: Artificial Sequence
<220> FEATURE:
<223> OTHER INFORMATION: Probe

<400> SEQUENCE: 173
gaggatggtc catctcatcg agccaa                                            26

<210> SEQ ID NO 174
<211> LENGTH: 26
<212> TYPE: DNA
<213> ORGANISM: Artificial Sequence
<220> FEATURE:
<223> OTHER INFORMATION: Probe

<400> SEQUENCE: 174
ggctatgatg gtgcactgtg ctggct                                            26

<210> SEQ ID NO 175
<211> LENGTH: 24
<212> TYPE: DNA
<213> ORGANISM: Artificial Sequence
<220> FEATURE:
<223> OTHER INFORMATION: Probe

<400> SEQUENCE: 175
cttaccatac ggccgcttcg ttga                                              24
```

<210> SEQ ID NO 176
<211> LENGTH: 27
<212> TYPE: DNA
<213> ORGANISM: Artificial Sequence
<220> FEATURE:
<223> OTHER INFORMATION: Probe

<400> SEQUENCE: 176
catggtgaat ccgggcagca gctcgca                                        27

<210> SEQ ID NO 177
<211> LENGTH: 24
<212> TYPE: DNA
<213> ORGANISM: Artificial Sequence
<220> FEATURE:
<223> OTHER INFORMATION: Probe

<400> SEQUENCE: 177
ccttctggtc tggcagtagt ggat                                           24

<210> SEQ ID NO 178
<211> LENGTH: 24
<212> TYPE: DNA
<213> ORGANISM: Artificial Sequence
<220> FEATURE:
<223> OTHER INFORMATION: Probe

<400> SEQUENCE: 178
gggaacctgt aaacgctctc ggaa                                           24

<210> SEQ ID NO 179
<211> LENGTH: 25
<212> TYPE: DNA
<213> ORGANISM: Artificial Sequence
<220> FEATURE:
<223> OTHER INFORMATION: Probe

<400> SEQUENCE: 179
caaagtgctg ggattacagg cgtga                                          25

<210> SEQ ID NO 180
<211> LENGTH: 25
<212> TYPE: DNA
<213> ORGANISM: Artificial Sequence
<220> FEATURE:
<223> OTHER INFORMATION: Probe

<400> SEQUENCE: 180
ccatgcagtc cgaatcgggg atcgt                                          25

<210> SEQ ID NO 181
<211> LENGTH: 25
<212> TYPE: DNA
<213> ORGANISM: Artificial Sequence
<220> FEATURE:
<223> OTHER INFORMATION: Probe

<400> SEQUENCE: 181
ccatctgcat acaggacgct cgtga                                          25

<210> SEQ ID NO 182
<211> LENGTH: 26
<212> TYPE: DNA
<213> ORGANISM: Artificial Sequence
<220> FEATURE:

```
<223> OTHER INFORMATION: Probe

<400> SEQUENCE: 182
caagatgttc atcgggggac tcagtt                                            26

<210> SEQ ID NO 183
<211> LENGTH: 25
<212> TYPE: DNA
<213> ORGANISM: Artificial Sequence
<220> FEATURE:
<223> OTHER INFORMATION: Probe

<400> SEQUENCE: 183
gtacccattg gtgaaggctg tggca                                             25

<210> SEQ ID NO 184
<211> LENGTH: 27
<212> TYPE: DNA
<213> ORGANISM: Artificial Sequence
<220> FEATURE:
<223> OTHER INFORMATION: Probe

<400> SEQUENCE: 184
gccatgagct tctttgccac tcggtgt                                           27

<210> SEQ ID NO 185
<211> LENGTH: 21
<212> TYPE: DNA
<213> ORGANISM: Artificial Sequence
<220> FEATURE:
<223> OTHER INFORMATION: Probe

<400> SEQUENCE: 185
gacctgggac cctctatgtc a                                                 21

<210> SEQ ID NO 186
<211> LENGTH: 25
<212> TYPE: DNA
<213> ORGANISM: Artificial Sequence
<220> FEATURE:
<223> OTHER INFORMATION: Probe

<400> SEQUENCE: 186
accatggctt ctccgtccaa aggca                                             25

<210> SEQ ID NO 187
<211> LENGTH: 24
<212> TYPE: DNA
<213> ORGANISM: Artificial Sequence
<220> FEATURE:
<223> OTHER INFORMATION: Probe

<400> SEQUENCE: 187
gtcttcctta ggacaggtgg taca                                              24

<210> SEQ ID NO 188
<211> LENGTH: 24
<212> TYPE: DNA
<213> ORGANISM: Artificial Sequence
<220> FEATURE:
<223> OTHER INFORMATION: Probe

<400> SEQUENCE: 188
ggaggtccgc tcggatgatg acaa                                              24
```

```
<210> SEQ ID NO 189
<211> LENGTH: 24
<212> TYPE: DNA
<213> ORGANISM: Artificial Sequence
<220> FEATURE:
<223> OTHER INFORMATION: Probe

<400> SEQUENCE: 189
cacgaagcac atgggcctga ggat                                              24

<210> SEQ ID NO 190
<211> LENGTH: 24
<212> TYPE: DNA
<213> ORGANISM: Artificial Sequence
<220> FEATURE:
<223> OTHER INFORMATION: Probe

<400> SEQUENCE: 190
ggacacggtg ttgtgctctc agaa                                              24

<210> SEQ ID NO 191
<211> LENGTH: 25
<212> TYPE: DNA
<213> ORGANISM: Artificial Sequence
<220> FEATURE:
<223> OTHER INFORMATION: Probe

<400> SEQUENCE: 191
cagttacgtg gccggttcca tcaca                                             25

<210> SEQ ID NO 192
<211> LENGTH: 26
<212> TYPE: DNA
<213> ORGANISM: Artificial Sequence
<220> FEATURE:
<223> OTHER INFORMATION: Probe

<400> SEQUENCE: 192
ggaaccgagg tgccaatgga ttcact                                            26

<210> SEQ ID NO 193
<211> LENGTH: 26
<212> TYPE: DNA
<213> ORGANISM: Artificial Sequence
<220> FEATURE:
<223> OTHER INFORMATION: Probe

<400> SEQUENCE: 193
gaagttggag ccactgtccc agccat                                            26

<210> SEQ ID NO 194
<211> LENGTH: 24
<212> TYPE: DNA
<213> ORGANISM: Artificial Sequence
<220> FEATURE:
<223> OTHER INFORMATION: Probe

<400> SEQUENCE: 194
ggcagcgttg gaacagaggt tgga                                              24

<210> SEQ ID NO 195
<211> LENGTH: 24
<212> TYPE: DNA
<213> ORGANISM: Artificial Sequence
<220> FEATURE:
<223> OTHER INFORMATION: Probe
```

```
<400> SEQUENCE: 195
ctctaaactg gagtggtcag ggct                                           24

<210> SEQ ID NO 196
<211> LENGTH: 26
<212> TYPE: DNA
<213> ORGANISM: Artificial Sequence
<220> FEATURE:
<223> OTHER INFORMATION: Probe

<400> SEQUENCE: 196
ccaccatggg taacaacttc tccagt                                         26

<210> SEQ ID NO 197
<211> LENGTH: 23
<212> TYPE: DNA
<213> ORGANISM: Artificial Sequence
<220> FEATURE:
<223> OTHER INFORMATION: Probe

<400> SEQUENCE: 197
cccgtcactt ctcaccgatg cca                                            23

<210> SEQ ID NO 198
<211> LENGTH: 24
<212> TYPE: DNA
<213> ORGANISM: Artificial Sequence
<220> FEATURE:
<223> OTHER INFORMATION: Probe

<400> SEQUENCE: 198
ctcggtgagc ctatgcgacc tcaa                                           24

<210> SEQ ID NO 199
<211> LENGTH: 23
<212> TYPE: DNA
<213> ORGANISM: Artificial Sequence
<220> FEATURE:
<223> OTHER INFORMATION: Probe

<400> SEQUENCE: 199
ggcacgttga ggtcgcatag gct                                            23

<210> SEQ ID NO 200
<211> LENGTH: 23
<212> TYPE: DNA
<213> ORGANISM: Artificial Sequence
<220> FEATURE:
<223> OTHER INFORMATION: Probe

<400> SEQUENCE: 200
ctcgggcagg ctcactggcg aat                                            23

<210> SEQ ID NO 201
<211> LENGTH: 24
<212> TYPE: DNA
<213> ORGANISM: Artificial Sequence
<220> FEATURE:
<223> OTHER INFORMATION: Probe

<400> SEQUENCE: 201
ctaggagctg cggtaggtct tgat                                           24

<210> SEQ ID NO 202
<211> LENGTH: 25
```

```
<212> TYPE: DNA
<213> ORGANISM: Artificial Sequence
<220> FEATURE:
<223> OTHER INFORMATION: Probe

<400> SEQUENCE: 202
gctaggagct gcggtaggtc ttgat                                            25

<210> SEQ ID NO 203
<211> LENGTH: 25
<212> TYPE: DNA
<213> ORGANISM: Artificial Sequence
<220> FEATURE:
<223> OTHER INFORMATION: Probe

<400> SEQUENCE: 203
gccccagggt tatgagacta tcact                                            25

<210> SEQ ID NO 204
<211> LENGTH: 27
<212> TYPE: DNA
<213> ORGANISM: Artificial Sequence
<220> FEATURE:
<223> OTHER INFORMATION: Probe

<400> SEQUENCE: 204
ccaacatgac caaatcgtac agcgaga                                          27

<210> SEQ ID NO 205
<211> LENGTH: 25
<212> TYPE: DNA
<213> ORGANISM: Artificial Sequence
<220> FEATURE:
<223> OTHER INFORMATION: Probe

<400> SEQUENCE: 205
ccgacagagc ccagatgtag ttctt                                            25

<210> SEQ ID NO 206
<211> LENGTH: 25
<212> TYPE: DNA
<213> ORGANISM: Artificial Sequence
<220> FEATURE:
<223> OTHER INFORMATION: Probe

<400> SEQUENCE: 206
ggtgaaactg gcgtgcctct aatca                                            25

<210> SEQ ID NO 207
<211> LENGTH: 28
<212> TYPE: DNA
<213> ORGANISM: Artificial Sequence
<220> FEATURE:
<223> OTHER INFORMATION: Probe

<400> SEQUENCE: 207
gtagagatgc cacactcgct ccgcggtt                                         28

<210> SEQ ID NO 208
<211> LENGTH: 24
<212> TYPE: DNA
<213> ORGANISM: Artificial Sequence
<220> FEATURE:
<223> OTHER INFORMATION: Probe

<400> SEQUENCE: 208
```

```
cgatcttgga cagcttctgc gtct                                              24
```

<210> SEQ ID NO 209
<211> LENGTH: 23
<212> TYPE: DNA
<213> ORGANISM: Artificial Sequence
<220> FEATURE:
<223> OTHER INFORMATION: Probe

<400> SEQUENCE: 209

```
cggcgcgaag tctcagttat gaa                                               23
```

<210> SEQ ID NO 210
<211> LENGTH: 26
<212> TYPE: DNA
<213> ORGANISM: Artificial Sequence
<220> FEATURE:
<223> OTHER INFORMATION: Probe

<400> SEQUENCE: 210

```
gactccagga gacgatgcga cactca                                            26
```

<210> SEQ ID NO 211
<211> LENGTH: 28
<212> TYPE: DNA
<213> ORGANISM: Artificial Sequence
<220> FEATURE:
<223> OTHER INFORMATION: Probe

<400> SEQUENCE: 211

```
ccgccatgtt aacactaccg tttgatga                                          28
```

<210> SEQ ID NO 212
<211> LENGTH: 25
<212> TYPE: DNA
<213> ORGANISM: Artificial Sequence
<220> FEATURE:
<223> OTHER INFORMATION: Probe

<400> SEQUENCE: 212

```
caagcagcct gccaccaagt ttgta                                             25
```

<210> SEQ ID NO 213
<211> LENGTH: 26
<212> TYPE: DNA
<213> ORGANISM: Artificial Sequence
<220> FEATURE:
<223> OTHER INFORMATION: Probe

<400> SEQUENCE: 213

```
gacaggggag gtgaatgacc actgtt                                            26
```

<210> SEQ ID NO 214
<211> LENGTH: 24
<212> TYPE: DNA
<213> ORGANISM: Artificial Sequence
<220> FEATURE:
<223> OTHER INFORMATION: Probe

<400> SEQUENCE: 214

```
ccggcgacat cactcaggag acca                                              24
```

<210> SEQ ID NO 215
<211> LENGTH: 26
<212> TYPE: DNA
<213> ORGANISM: Artificial Sequence
<220> FEATURE:
<223> OTHER INFORMATION: Probe

<400> SEQUENCE: 215
ctgtccgtcg gtcctgcaca gcgcaa                                           26

<210> SEQ ID NO 216
<211> LENGTH: 24
<212> TYPE: DNA
<213> ORGANISM: Artificial Sequence
<220> FEATURE:
<223> OTHER INFORMATION: Probe

<400> SEQUENCE: 216
gtggtaagga atgaaacagg gcgt                                             24

<210> SEQ ID NO 217
<211> LENGTH: 26
<212> TYPE: DNA
<213> ORGANISM: Artificial Sequence
<220> FEATURE:
<223> OTHER INFORMATION: Probe

<400> SEQUENCE: 217
ccaggatgtt cgtcaaatct gagact                                           26

<210> SEQ ID NO 218
<211> LENGTH: 25
<212> TYPE: DNA
<213> ORGANISM: Artificial Sequence
<220> FEATURE:
<223> OTHER INFORMATION: Probe

<400> SEQUENCE: 218
cagctctaga tacagtccct ggcga                                            25

<210> SEQ ID NO 219
<211> LENGTH: 26
<212> TYPE: DNA
<213> ORGANISM: Artificial Sequence
<220> FEATURE:
<223> OTHER INFORMATION: Probe

<400> SEQUENCE: 219
cctcgctgct catcgctctc tattct                                           26

<210> SEQ ID NO 220
<211> LENGTH: 26
<212> TYPE: DNA
<213> ORGANISM: Artificial Sequence
<220> FEATURE:
<223> OTHER INFORMATION: Probe

<400> SEQUENCE: 220
ccacgatgac gcctcaaccc tcgggt                                           26

<210> SEQ ID NO 221
<211> LENGTH: 26
<212> TYPE: DNA
<213> ORGANISM: Artificial Sequence
<220> FEATURE:
<223> OTHER INFORMATION: Probe

<400> SEQUENCE: 221
ctgcttgctc agtgccaact cgctct                                           26

```
<210> SEQ ID NO 222
<211> LENGTH: 26
<212> TYPE: DNA
<213> ORGANISM: Artificial Sequence
<220> FEATURE:
<223> OTHER INFORMATION: Probe

<400> SEQUENCE: 222
cagcgacaga caggtccttt cacaga                                          26

<210> SEQ ID NO 223
<211> LENGTH: 28
<212> TYPE: DNA
<213> ORGANISM: Artificial Sequence
<220> FEATURE:
<223> OTHER INFORMATION: Probe

<400> SEQUENCE: 223
cagaaaatct gagaaagcca gactgcct                                        28

<210> SEQ ID NO 224
<211> LENGTH: 25
<212> TYPE: DNA
<213> ORGANISM: Artificial Sequence
<220> FEATURE:
<223> OTHER INFORMATION: Probe

<400> SEQUENCE: 224
ggtctcgaac catgtcgctg accaa                                           25

<210> SEQ ID NO 225
<211> LENGTH: 24
<212> TYPE: DNA
<213> ORGANISM: Artificial Sequence
<220> FEATURE:
<223> OTHER INFORMATION: Probe

<400> SEQUENCE: 225
gggctttgag cgcgtgacat ggtt                                            24

<210> SEQ ID NO 226
<211> LENGTH: 25
<212> TYPE: DNA
<213> ORGANISM: Artificial Sequence
<220> FEATURE:
<223> OTHER INFORMATION: Probe

<400> SEQUENCE: 226
cccacgccct tctcagtcaa agaca                                           25

<210> SEQ ID NO 227
<211> LENGTH: 24
<212> TYPE: DNA
<213> ORGANISM: Artificial Sequence
<220> FEATURE:
<223> OTHER INFORMATION: Probe

<400> SEQUENCE: 227
cgacgccgaa gttcacgaag ttgt                                            24

<210> SEQ ID NO 228
<211> LENGTH: 25
<212> TYPE: DNA
<213> ORGANISM: Artificial Sequence
<220> FEATURE:
<223> OTHER INFORMATION: Probe
```

<400> SEQUENCE: 228
gctaatatcc cggctgccag cgcat                                  25

<210> SEQ ID NO 229
<211> LENGTH: 25
<212> TYPE: DNA
<213> ORGANISM: Artificial Sequence
<220> FEATURE:
<223> OTHER INFORMATION: Probe

<400> SEQUENCE: 229
ctgcggcctc accagttcca ggaga                                  25

<210> SEQ ID NO 230
<211> LENGTH: 23
<212> TYPE: DNA
<213> ORGANISM: Artificial Sequence
<220> FEATURE:
<223> OTHER INFORMATION: Probe

<400> SEQUENCE: 230
gcatggagcg ctgccccagc cta                                    23

<210> SEQ ID NO 231
<211> LENGTH: 23
<212> TYPE: DNA
<213> ORGANISM: Artificial Sequence
<220> FEATURE:
<223> OTHER INFORMATION: Probe

<400> SEQUENCE: 231
cccgagttct agcacgagca ctt                                    23

<210> SEQ ID NO 232
<211> LENGTH: 25
<212> TYPE: DNA
<213> ORGANISM: Artificial Sequence
<220> FEATURE:
<223> OTHER INFORMATION: Probe

<400> SEQUENCE: 232
cagcggcagg aactgcaaac atgat                                  25

<210> SEQ ID NO 233
<211> LENGTH: 25
<212> TYPE: DNA
<213> ORGANISM: Artificial Sequence
<220> FEATURE:
<223> OTHER INFORMATION: Probe

<400> SEQUENCE: 233
cagccttcac agtagcacct ccctt                                  25

<210> SEQ ID NO 234
<211> LENGTH: 24
<212> TYPE: DNA
<213> ORGANISM: Artificial Sequence
<220> FEATURE:
<223> OTHER INFORMATION: Probe

<400> SEQUENCE: 234
ggaaccacag agcgggtatg ccta                                   24

<210> SEQ ID NO 235

<211> LENGTH: 25
<212> TYPE: DNA
<213> ORGANISM: Artificial Sequence
<220> FEATURE:
<223> OTHER INFORMATION: Probe

<400> SEQUENCE: 235
cagggagttg gtgttgtagc cgtaa                                              25

<210> SEQ ID NO 236
<211> LENGTH: 25
<212> TYPE: DNA
<213> ORGANISM: Artificial Sequence
<220> FEATURE:
<223> OTHER INFORMATION: Probe

<400> SEQUENCE: 236
ggtgacccgc tgactgatga ggtat                                              25

<210> SEQ ID NO 237
<211> LENGTH: 25
<212> TYPE: DNA
<213> ORGANISM: Artificial Sequence
<220> FEATURE:
<223> OTHER INFORMATION: Probe

<400> SEQUENCE: 237
cagtgacttc tagagctcag tggca                                              25

<210> SEQ ID NO 238
<211> LENGTH: 25
<212> TYPE: DNA
<213> ORGANISM: Artificial Sequence
<220> FEATURE:
<223> OTHER INFORMATION: Probe

<400> SEQUENCE: 238
ccaggcgcag aatctcaatc ttgga                                              25

<210> SEQ ID NO 239
<211> LENGTH: 24
<212> TYPE: DNA
<213> ORGANISM: Artificial Sequence
<220> FEATURE:
<223> OTHER INFORMATION: Probe

<400> SEQUENCE: 239
ccaagcatct ccaagccact gact                                               24

<210> SEQ ID NO 240
<211> LENGTH: 24
<212> TYPE: DNA
<213> ORGANISM: Artificial Sequence
<220> FEATURE:
<223> OTHER INFORMATION: Probe

<400> SEQUENCE: 240
ccaggacgtg gttgagatag gaga                                               24

<210> SEQ ID NO 241
<211> LENGTH: 25
<212> TYPE: DNA
<213> ORGANISM: Artificial Sequence
<220> FEATURE:
<223> OTHER INFORMATION: Probe

<400> SEQUENCE: 241
cagtgatctg gaggagctgg agcaa                                              25

<210> SEQ ID NO 242
<211> LENGTH: 27
<212> TYPE: DNA
<213> ORGANISM: Artificial Sequence
<220> FEATURE:
<223> OTHER INFORMATION: Probe

<400> SEQUENCE: 242
ggcgatcagc aggatctcct ctgaggt                                            27

<210> SEQ ID NO 243
<211> LENGTH: 25
<212> TYPE: DNA
<213> ORGANISM: Artificial Sequence
<220> FEATURE:
<223> OTHER INFORMATION: Probe

<400> SEQUENCE: 243
cactttgaga agcagccgcc ttcca                                              25

<210> SEQ ID NO 244
<211> LENGTH: 25
<212> TYPE: DNA
<213> ORGANISM: Artificial Sequence
<220> FEATURE:
<223> OTHER INFORMATION: Probe

<400> SEQUENCE: 244
ccctatgatg atgacagtcg cacct                                              25

<210> SEQ ID NO 245
<211> LENGTH: 25
<212> TYPE: DNA
<213> ORGANISM: Artificial Sequence
<220> FEATURE:
<223> OTHER INFORMATION: Probe

<400> SEQUENCE: 245
gcagcgggct gaacctgaag gagga                                              25

<210> SEQ ID NO 246
<211> LENGTH: 24
<212> TYPE: DNA
<213> ORGANISM: Artificial Sequence
<220> FEATURE:
<223> OTHER INFORMATION: Probe

<400> SEQUENCE: 246
gggcgtctca ttccggttgc caca                                               24

<210> SEQ ID NO 247
<211> LENGTH: 25
<212> TYPE: DNA
<213> ORGANISM: Artificial Sequence
<220> FEATURE:
<223> OTHER INFORMATION: Probe

<400> SEQUENCE: 247
ctagaggacg aggcagagct ggaca                                              25

<210> SEQ ID NO 248
<211> LENGTH: 25
<212> TYPE: DNA

-continued

```
<213> ORGANISM: Artificial Sequence
<220> FEATURE:
<223> OTHER INFORMATION: Probe

<400> SEQUENCE: 248
ccacccagct gttagcatga tgtct                                          25

<210> SEQ ID NO 249
<211> LENGTH: 25
<212> TYPE: DNA
<213> ORGANISM: Artificial Sequence
<220> FEATURE:
<223> OTHER INFORMATION: Probe

<400> SEQUENCE: 249
cagacatctt catgcgagag gaggt                                          25

<210> SEQ ID NO 250
<211> LENGTH: 25
<212> TYPE: DNA
<213> ORGANISM: Artificial Sequence
<220> FEATURE:
<223> OTHER INFORMATION: Probe

<400> SEQUENCE: 250
gagatggctg gtgactgcat tggta                                          25

<210> SEQ ID NO 251
<211> LENGTH: 25
<212> TYPE: DNA
<213> ORGANISM: Artificial Sequence
<220> FEATURE:
<223> OTHER INFORMATION: Probe

<400> SEQUENCE: 251
ccagccagag ccagcatgca gaaca                                          25

<210> SEQ ID NO 252
<211> LENGTH: 26
<212> TYPE: DNA
<213> ORGANISM: Artificial Sequence
<220> FEATURE:
<223> OTHER INFORMATION: Probe

<400> SEQUENCE: 252
ggttggtaga cactggtgct gaaact                                         26

<210> SEQ ID NO 253
<211> LENGTH: 24
<212> TYPE: DNA
<213> ORGANISM: Artificial Sequence
<220> FEATURE:
<223> OTHER INFORMATION: Probe

<400> SEQUENCE: 253
gtagcctttg gagatggacg agca                                           24

<210> SEQ ID NO 254
<211> LENGTH: 23
<212> TYPE: DNA
<213> ORGANISM: Artificial Sequence
<220> FEATURE:
<223> OTHER INFORMATION: Probe

<400> SEQUENCE: 254
ctgcatctgg atggagctga act                                            23
```

<210> SEQ ID NO 255
<211> LENGTH: 23
<212> TYPE: DNA
<213> ORGANISM: Artificial Sequence
<220> FEATURE:
<223> OTHER INFORMATION: Probe

<400> SEQUENCE: 255
ccgatggact actcctacct caa                                        23

<210> SEQ ID NO 256
<211> LENGTH: 25
<212> TYPE: DNA
<213> ORGANISM: Artificial Sequence
<220> FEATURE:
<223> OTHER INFORMATION: Probe

<400> SEQUENCE: 256
cgtggactcc ttggaatcgt cgtct                                      25

<210> SEQ ID NO 257
<211> LENGTH: 23
<212> TYPE: DNA
<213> ORGANISM: Artificial Sequence
<220> FEATURE:
<223> OTHER INFORMATION: Probe

<400> SEQUENCE: 257
gagtggccct gacttggtct cca                                        23

<210> SEQ ID NO 258
<211> LENGTH: 36
<212> TYPE: DNA
<213> ORGANISM: Artificial Sequence
<220> FEATURE:
<223> OTHER INFORMATION: Probe

<400> SEQUENCE: 258
gcagtatggc tgggatggac acctcgagcc tggctt                          36

<210> SEQ ID NO 259
<211> LENGTH: 24
<212> TYPE: DNA
<213> ORGANISM: Artificial Sequence
<220> FEATURE:
<223> OTHER INFORMATION: Probe

<400> SEQUENCE: 259
ctccagccac cttctccata tcca                                       24

<210> SEQ ID NO 260
<211> LENGTH: 25
<212> TYPE: DNA
<213> ORGANISM: Artificial Sequence
<220> FEATURE:
<223> OTHER INFORMATION: Probe

<400> SEQUENCE: 260
gctctcgtcg tccctggaag agtca                                      25

<210> SEQ ID NO 261
<211> LENGTH: 25
<212> TYPE: DNA
<213> ORGANISM: Artificial Sequence
<220> FEATURE:

-continued

<223> OTHER INFORMATION: Probe

<400> SEQUENCE: 261
cgccgcagga ttccagatca gaaca                                    25

<210> SEQ ID NO 262
<211> LENGTH: 24
<212> TYPE: DNA
<213> ORGANISM: Artificial Sequence
<220> FEATURE:
<223> OTHER INFORMATION: Probe

<400> SEQUENCE: 262
gccgcaggat tccagatcag aaca                                     24

<210> SEQ ID NO 263
<211> LENGTH: 24
<212> TYPE: DNA
<213> ORGANISM: Artificial Sequence
<220> FEATURE:
<223> OTHER INFORMATION: Probe

<400> SEQUENCE: 263
ccagtatggc cgggatggat acct                                     24

<210> SEQ ID NO 264
<211> LENGTH: 25
<212> TYPE: DNA
<213> ORGANISM: Artificial Sequence
<220> FEATURE:
<223> OTHER INFORMATION: Probe

<400> SEQUENCE: 264
cgcagatcgc agatcagaac atact                                    25

<210> SEQ ID NO 265
<211> LENGTH: 24
<212> TYPE: DNA
<213> ORGANISM: Artificial Sequence
<220> FEATURE:
<223> OTHER INFORMATION: Probe

<400> SEQUENCE: 265
ccaccatgga gttcggcctg ctca                                     24

<210> SEQ ID NO 266
<211> LENGTH: 27
<212> TYPE: DNA
<213> ORGANISM: Artificial Sequence
<220> FEATURE:
<223> OTHER INFORMATION: Probe

<400> SEQUENCE: 266
cctttccacg gcgtactggc acggact                                  27

<210> SEQ ID NO 267
<211> LENGTH: 26
<212> TYPE: DNA
<213> ORGANISM: Artificial Sequence
<220> FEATURE:
<223> OTHER INFORMATION: Probe

<400> SEQUENCE: 267
ggcatggagt ttgggctgct tggtga                                   26

```
<210> SEQ ID NO 268
<211> LENGTH: 27
<212> TYPE: DNA
<213> ORGANISM: Artificial Sequence
<220> FEATURE:
<223> OTHER INFORMATION: Probe

<400> SEQUENCE: 268
cacggcgtac tggcaggggc taaggtt                                        27

<210> SEQ ID NO 269
<211> LENGTH: 25
<212> TYPE: DNA
<213> ORGANISM: Artificial Sequence
<220> FEATURE:
<223> OTHER INFORMATION: Probe

<400> SEQUENCE: 269
ggttacatgg gactggacag cgcgt                                          25

<210> SEQ ID NO 270
<211> LENGTH: 24
<212> TYPE: DNA
<213> ORGANISM: Artificial Sequence
<220> FEATURE:
<223> OTHER INFORMATION: Probe

<400> SEQUENCE: 270
ctaagtctgg atgaagaggt ggaa                                           24

<210> SEQ ID NO 271
<211> LENGTH: 25
<212> TYPE: DNA
<213> ORGANISM: Artificial Sequence
<220> FEATURE:
<223> OTHER INFORMATION: Probe

<400> SEQUENCE: 271
gtgaccgctg cggctacaat actaa                                          25

<210> SEQ ID NO 272
<211> LENGTH: 25
<212> TYPE: DNA
<213> ORGANISM: Artificial Sequence
<220> FEATURE:
<223> OTHER INFORMATION: Probe

<400> SEQUENCE: 272
ggacaagtag gatgcttaga tttga                                          25

<210> SEQ ID NO 273
<211> LENGTH: 23
<212> TYPE: DNA
<213> ORGANISM: Artificial Sequence
<220> FEATURE:
<223> OTHER INFORMATION: Probe

<400> SEQUENCE: 273
ccagcatgtc gcggaggaag caa                                            23

<210> SEQ ID NO 274
<211> LENGTH: 25
<212> TYPE: DNA
<213> ORGANISM: Artificial Sequence
<220> FEATURE:
<223> OTHER INFORMATION: Probe
```

```
<400> SEQUENCE: 274
ggaggaagca agcgaagcct caaca                                      25

<210> SEQ ID NO 275
<211> LENGTH: 24
<212> TYPE: DNA
<213> ORGANISM: Artificial Sequence
<220> FEATURE:
<223> OTHER INFORMATION: Probe

<400> SEQUENCE: 275
cgagttgagg tagagaggtt gtga                                       24

<210> SEQ ID NO 276
<211> LENGTH: 24
<212> TYPE: DNA
<213> ORGANISM: Artificial Sequence
<220> FEATURE:
<223> OTHER INFORMATION: Probe

<400> SEQUENCE: 276
gaaagcagcg gaaaccccaa cagt                                       24

<210> SEQ ID NO 277
<211> LENGTH: 29
<212> TYPE: DNA
<213> ORGANISM: Artificial Sequence
<220> FEATURE:
<223> OTHER INFORMATION: Probe

<400> SEQUENCE: 277
ccaggatgac ttcactacca agctgggca                                  29

<210> SEQ ID NO 278
<211> LENGTH: 25
<212> TYPE: DNA
<213> ORGANISM: Artificial Sequence
<220> FEATURE:
<223> OTHER INFORMATION: Probe

<400> SEQUENCE: 278
gcagcacccg tagctcttcc aagat                                      25

<210> SEQ ID NO 279
<211> LENGTH: 25
<212> TYPE: DNA
<213> ORGANISM: Artificial Sequence
<220> FEATURE:
<223> OTHER INFORMATION: Probe

<400> SEQUENCE: 279
ggctcatggg atcgtggggt catct                                      25

<210> SEQ ID NO 280
<211> LENGTH: 25
<212> TYPE: DNA
<213> ORGANISM: Artificial Sequence
<220> FEATURE:
<223> OTHER INFORMATION: Probe

<400> SEQUENCE: 280
cgatcatgaa gcaccgcaag ggcaa                                      25

<210> SEQ ID NO 281
<211> LENGTH: 24
```

```
<212> TYPE: DNA
<213> ORGANISM: Artificial Sequence
<220> FEATURE:
<223> OTHER INFORMATION: Probe

<400> SEQUENCE: 281
gaacttcttc tggcagatgg ggca                                          24

<210> SEQ ID NO 282
<211> LENGTH: 25
<212> TYPE: DNA
<213> ORGANISM: Artificial Sequence
<220> FEATURE:
<223> OTHER INFORMATION: Probe

<400> SEQUENCE: 282
ggaacatgga cgaaggaatt cctca                                         25

<210> SEQ ID NO 283
<211> LENGTH: 24
<212> TYPE: DNA
<213> ORGANISM: Artificial Sequence
<220> FEATURE:
<223> OTHER INFORMATION: Probe

<400> SEQUENCE: 283
caagtggttg atcagctgga caca                                          24

<210> SEQ ID NO 284
<211> LENGTH: 24
<212> TYPE: DNA
<213> ORGANISM: Artificial Sequence
<220> FEATURE:
<223> OTHER INFORMATION: Probe

<400> SEQUENCE: 284
ctagtgcaga caggagcgcg cagt                                          24

<210> SEQ ID NO 285
<211> LENGTH: 25
<212> TYPE: DNA
<213> ORGANISM: Artificial Sequence
<220> FEATURE:
<223> OTHER INFORMATION: Probe

<400> SEQUENCE: 285
gagcacggag acctaccagg gatgt                                         25

<210> SEQ ID NO 286
<211> LENGTH: 24
<212> TYPE: DNA
<213> ORGANISM: Artificial Sequence
<220> FEATURE:
<223> OTHER INFORMATION: Probe

<400> SEQUENCE: 286
cgtgaacctg cgtccgtggt cact                                          24

<210> SEQ ID NO 287
<211> LENGTH: 23
<212> TYPE: DNA
<213> ORGANISM: Artificial Sequence
<220> FEATURE:
<223> OTHER INFORMATION: Probe

<400> SEQUENCE: 287
```

-continued

| | |
|---|---|
| gcagcaggat ccctagaga gtt | 23 |

<210> SEQ ID NO 288
<211> LENGTH: 24
<212> TYPE: DNA
<213> ORGANISM: Artificial Sequence
<220> FEATURE:
<223> OTHER INFORMATION: Probe

<400> SEQUENCE: 288

| | |
|---|---|
| aggatgctgc tgctggcgag atgt | 24 |

<210> SEQ ID NO 289
<211> LENGTH: 27
<212> TYPE: DNA
<213> ORGANISM: Artificial Sequence
<220> FEATURE:
<223> OTHER INFORMATION: Probe

<400> SEQUENCE: 289

| | |
|---|---|
| gccctgctcc aggtgcaccg tggccga | 27 |

<210> SEQ ID NO 290
<211> LENGTH: 29
<212> TYPE: DNA
<213> ORGANISM: Artificial Sequence
<220> FEATURE:
<223> OTHER INFORMATION: Probe

<400> SEQUENCE: 290

| | |
|---|---|
| gccatggtat tccgctcccc cctagacct | 29 |

<210> SEQ ID NO 291
<211> LENGTH: 23
<212> TYPE: DNA
<213> ORGANISM: Artificial Sequence
<220> FEATURE:
<223> OTHER INFORMATION: Probe

<400> SEQUENCE: 291

| | |
|---|---|
| gcctggtgct ggagcctgtt ctt | 23 |

<210> SEQ ID NO 292
<211> LENGTH: 29
<212> TYPE: DNA
<213> ORGANISM: Artificial Sequence
<220> FEATURE:
<223> OTHER INFORMATION: Probe

<400> SEQUENCE: 292

| | |
|---|---|
| ggctatcata catcacattc cgagtcgct | 29 |

<210> SEQ ID NO 293
<211> LENGTH: 29
<212> TYPE: DNA
<213> ORGANISM: Artificial Sequence
<220> FEATURE:
<223> OTHER INFORMATION: Probe

<400> SEQUENCE: 293

| | |
|---|---|
| cgtatgttca ggtccaaacg ctcggggct | 29 |

<210> SEQ ID NO 294
<211> LENGTH: 26
<212> TYPE: DNA
<213> ORGANISM: Artificial Sequence

```
<220> FEATURE:
<223> OTHER INFORMATION: Probe

<400> SEQUENCE: 294
ccgccactat ctggggttgt tgagga                                          26

<210> SEQ ID NO 295
<211> LENGTH: 24
<212> TYPE: DNA
<213> ORGANISM: Artificial Sequence
<220> FEATURE:
<223> OTHER INFORMATION: Probe

<400> SEQUENCE: 295
ccccgcatgt tcaggaccaa acga                                            24

<210> SEQ ID NO 296
<211> LENGTH: 24
<212> TYPE: DNA
<213> ORGANISM: Artificial Sequence
<220> FEATURE:
<223> OTHER INFORMATION: Probe

<400> SEQUENCE: 296
cacgcggcta ccggctgttg aaga                                            24

<210> SEQ ID NO 297
<211> LENGTH: 26
<212> TYPE: DNA
<213> ORGANISM: Artificial Sequence
<220> FEATURE:
<223> OTHER INFORMATION: Probe

<400> SEQUENCE: 297
cccgatgtac agcatgatga tggaga                                          26

<210> SEQ ID NO 298
<211> LENGTH: 26
<212> TYPE: DNA
<213> ORGANISM: Artificial Sequence
<220> FEATURE:
<223> OTHER INFORMATION: Probe

<400> SEQUENCE: 298
gtacatgctg atcatctcgc gcaggt                                          26

<210> SEQ ID NO 299
<211> LENGTH: 26
<212> TYPE: DNA
<213> ORGANISM: Artificial Sequence
<220> FEATURE:
<223> OTHER INFORMATION: Probe

<400> SEQUENCE: 299
gccatgtaca acatgatgga gacgga                                          26

<210> SEQ ID NO 300
<211> LENGTH: 25
<212> TYPE: DNA
<213> ORGANISM: Artificial Sequence
<220> FEATURE:
<223> OTHER INFORMATION: Probe

<400> SEQUENCE: 300
cctccagttc gctgtccggc cctca                                           25
```

<210> SEQ ID NO 301
<211> LENGTH: 25
<212> TYPE: DNA
<213> ORGANISM: Artificial Sequence
<220> FEATURE:
<223> OTHER INFORMATION: Probe

<400> SEQUENCE: 301
caggcagact gtgaatgcga cctgt                                    25

<210> SEQ ID NO 302
<211> LENGTH: 26
<212> TYPE: DNA
<213> ORGANISM: Artificial Sequence
<220> FEATURE:
<223> OTHER INFORMATION: Probe

<400> SEQUENCE: 302
ctcagatgtg ggtcagcggc accgtt                                   26

<210> SEQ ID NO 303
<211> LENGTH: 25
<212> TYPE: DNA
<213> ORGANISM: Artificial Sequence
<220> FEATURE:
<223> OTHER INFORMATION: Probe

<400> SEQUENCE: 303
gtgggcgttg gactctttgc gagga                                    25

<210> SEQ ID NO 304
<211> LENGTH: 25
<212> TYPE: DNA
<213> ORGANISM: Artificial Sequence
<220> FEATURE:
<223> OTHER INFORMATION: Probe

<400> SEQUENCE: 304
gcgacatggc ggaggagcag gatct                                    25

<210> SEQ ID NO 305
<211> LENGTH: 26
<212> TYPE: DNA
<213> ORGANISM: Artificial Sequence
<220> FEATURE:
<223> OTHER INFORMATION: Probe

<400> SEQUENCE: 305
gctggtactt gtagtccggg tggtct                                   26

<210> SEQ ID NO 306
<211> LENGTH: 24
<212> TYPE: DNA
<213> ORGANISM: Artificial Sequence
<220> FEATURE:
<223> OTHER INFORMATION: Probe

<400> SEQUENCE: 306
cctttagggc cgggacagtg tcgt                                     24

<210> SEQ ID NO 307
<211> LENGTH: 26
<212> TYPE: DNA
<213> ORGANISM: Artificial Sequence
<220> FEATURE:
<223> OTHER INFORMATION: Probe

```
<400> SEQUENCE: 307
cacgttgccg aagtcgatgt gaggct                                      26

<210> SEQ ID NO 308
<211> LENGTH: 24
<212> TYPE: DNA
<213> ORGANISM: Artificial Sequence
<220> FEATURE:
<223> OTHER INFORMATION: Probe

<400> SEQUENCE: 308
ggatcatggt gcagcaggcg gaga                                        24

<210> SEQ ID NO 309
<211> LENGTH: 25
<212> TYPE: DNA
<213> ORGANISM: Artificial Sequence
<220> FEATURE:
<223> OTHER INFORMATION: Probe

<400> SEQUENCE: 309
ccagaaacac gcacttgacc gtctt                                       25

<210> SEQ ID NO 310
<211> LENGTH: 25
<212> TYPE: DNA
<213> ORGANISM: Artificial Sequence
<220> FEATURE:
<223> OTHER INFORMATION: Probe

<400> SEQUENCE: 310
gcgattgact gcctggagga tgaga                                       25

<210> SEQ ID NO 311
<211> LENGTH: 25
<212> TYPE: DNA
<213> ORGANISM: Artificial Sequence
<220> FEATURE:
<223> OTHER INFORMATION: Probe

<400> SEQUENCE: 311
cgaagcacct gctgccacct tgtct                                       25

<210> SEQ ID NO 312
<211> LENGTH: 26
<212> TYPE: DNA
<213> ORGANISM: Artificial Sequence
<220> FEATURE:
<223> OTHER INFORMATION: Probe

<400> SEQUENCE: 312
ctggacgagg tcttcttcaa cagcga                                      26

<210> SEQ ID NO 313
<211> LENGTH: 25
<212> TYPE: DNA
<213> ORGANISM: Artificial Sequence
<220> FEATURE:
<223> OTHER INFORMATION: Probe

<400> SEQUENCE: 313
ggaatggtcc tcgtccgaag tgaga                                       25

<210> SEQ ID NO 314
```

```
<211> LENGTH: 25
<212> TYPE: DNA
<213> ORGANISM: Artificial Sequence
<220> FEATURE:
<223> OTHER INFORMATION: Probe

<400> SEQUENCE: 314
gcatagttgg cccgatgacc atgct                                              25

<210> SEQ ID NO 315
<211> LENGTH: 26
<212> TYPE: DNA
<213> ORGANISM: Artificial Sequence
<220> FEATURE:
<223> OTHER INFORMATION: Probe

<400> SEQUENCE: 315
gggtaagctc ctcttcagga aaggca                                             26

<210> SEQ ID NO 316
<211> LENGTH: 24
<212> TYPE: DNA
<213> ORGANISM: Artificial Sequence
<220> FEATURE:
<223> OTHER INFORMATION: Probe

<400> SEQUENCE: 316
ggtaacacgg cgggtttcac caca                                               24

<210> SEQ ID NO 317
<211> LENGTH: 25
<212> TYPE: DNA
<213> ORGANISM: Artificial Sequence
<220> FEATURE:
<223> OTHER INFORMATION: Probe

<400> SEQUENCE: 317
gcctgctcat atctgtcgtc atcct                                              25

<210> SEQ ID NO 318
<211> LENGTH: 24
<212> TYPE: DNA
<213> ORGANISM: Artificial Sequence
<220> FEATURE:
<223> OTHER INFORMATION: Probe

<400> SEQUENCE: 318
gtagagcagc agtgaatggc ttgt                                               24

<210> SEQ ID NO 319
<211> LENGTH: 25
<212> TYPE: DNA
<213> ORGANISM: Artificial Sequence
<220> FEATURE:
<223> OTHER INFORMATION: Probe

<400> SEQUENCE: 319
ggatcagaac aacagcctgc cacct                                              25

<210> SEQ ID NO 320
<211> LENGTH: 26
<212> TYPE: DNA
<213> ORGANISM: Artificial Sequence
<220> FEATURE:
<223> OTHER INFORMATION: Probe

<400> SEQUENCE: 320
```
gcggtacaat cccagaactc tccgaa      26

<210> SEQ ID NO 321
<211> LENGTH: 26
<212> TYPE: DNA
<213> ORGANISM: Artificial Sequence
<220> FEATURE:
<223> OTHER INFORMATION: Probe

<400> SEQUENCE: 321
ggcacgaagt gcaatggtct ttaggt      26

<210> SEQ ID NO 322
<211> LENGTH: 26
<212> TYPE: DNA
<213> ORGANISM: Artificial Sequence
<220> FEATURE:
<223> OTHER INFORMATION: Probe

<400> SEQUENCE: 322
cgtggttcgt ggctctctta tcctca      26

<210> SEQ ID NO 323
<211> LENGTH: 27
<212> TYPE: DNA
<213> ORGANISM: Artificial Sequence
<220> FEATURE:
<223> OTHER INFORMATION: Probe

<400> SEQUENCE: 323
cttcacatca cagctcccca ccatgtt      27

<210> SEQ ID NO 324
<211> LENGTH: 26
<212> TYPE: DNA
<213> ORGANISM: Artificial Sequence
<220> FEATURE:
<223> OTHER INFORMATION: Probe

<400> SEQUENCE: 324
ggaggcaagg gtacatgaga gccatt      26

<210> SEQ ID NO 325
<211> LENGTH: 24
<212> TYPE: DNA
<213> ORGANISM: Artificial Sequence
<220> FEATURE:
<223> OTHER INFORMATION: Probe

<400> SEQUENCE: 325
ccagtctgag cgttgcgttc ggtt      24

<210> SEQ ID NO 326
<211> LENGTH: 24
<212> TYPE: DNA
<213> ORGANISM: Artificial Sequence
<220> FEATURE:
<223> OTHER INFORMATION: Probe

<400> SEQUENCE: 326
ggccttggga ctcagtgagg aaca      24

<210> SEQ ID NO 327
<211> LENGTH: 25
<212> TYPE: DNA

```
<213> ORGANISM: Artificial Sequence
<220> FEATURE:
<223> OTHER INFORMATION: Probe

<400> SEQUENCE: 327
cgtctgagga ttctgttttg gagga                                              25

<210> SEQ ID NO 328
<211> LENGTH: 28
<212> TYPE: DNA
<213> ORGANISM: Artificial Sequence
<220> FEATURE:
<223> OTHER INFORMATION: Probe

<400> SEQUENCE: 328
ctcggaaagg gctgagagat aatctggt                                           28

<210> SEQ ID NO 329
<211> LENGTH: 24
<212> TYPE: DNA
<213> ORGANISM: Artificial Sequence
<220> FEATURE:
<223> OTHER INFORMATION: Probe

<400> SEQUENCE: 329
cggcttgcta agctgtcaat ggtt                                               24

<210> SEQ ID NO 330
<211> LENGTH: 24
<212> TYPE: DNA
<213> ORGANISM: Artificial Sequence
<220> FEATURE:
<223> OTHER INFORMATION: Probe

<400> SEQUENCE: 330
gtagacaagg gctaagtgca gaca                                               24

<210> SEQ ID NO 331
<211> LENGTH: 25
<212> TYPE: DNA
<213> ORGANISM: Artificial Sequence
<220> FEATURE:
<223> OTHER INFORMATION: Probe

<400> SEQUENCE: 331
gtgttgacgg acctactgcc aagga                                              25

<210> SEQ ID NO 332
<211> LENGTH: 24
<212> TYPE: DNA
<213> ORGANISM: Artificial Sequence
<220> FEATURE:
<223> OTHER INFORMATION: Probe

<400> SEQUENCE: 332
ggtatcatgc tggaaagtgc ctct                                               24

<210> SEQ ID NO 333
<211> LENGTH: 24
<212> TYPE: DNA
<213> ORGANISM: Artificial Sequence
<220> FEATURE:
<223> OTHER INFORMATION: Probe

<400> SEQUENCE: 333
gccaagcgca agttgtctga tgat                                               24
```

<210> SEQ ID NO 334
<211> LENGTH: 26
<212> TYPE: DNA
<213> ORGANISM: Artificial Sequence
<220> FEATURE:
<223> OTHER INFORMATION: Probe

<400> SEQUENCE: 334
cgttctctac cagacatacc tgctca                                      26

<210> SEQ ID NO 335
<211> LENGTH: 24
<212> TYPE: DNA
<213> ORGANISM: Artificial Sequence
<220> FEATURE:
<223> OTHER INFORMATION: Probe

<400> SEQUENCE: 335
gcagccagga acatcaggtg ctta                                        24

<210> SEQ ID NO 336
<211> LENGTH: 25
<212> TYPE: DNA
<213> ORGANISM: Artificial Sequence
<220> FEATURE:
<223> OTHER INFORMATION: Probe

<400> SEQUENCE: 336
gggagtgcag tctctatgga agagt                                       25

<210> SEQ ID NO 337
<211> LENGTH: 26
<212> TYPE: DNA
<213> ORGANISM: Artificial Sequence
<220> FEATURE:
<223> OTHER INFORMATION: Probe

<400> SEQUENCE: 337
caccttccac ttgcactcct tgatgt                                      26

<210> SEQ ID NO 338
<211> LENGTH: 25
<212> TYPE: DNA
<213> ORGANISM: Artificial Sequence
<220> FEATURE:
<223> OTHER INFORMATION: Probe

<400> SEQUENCE: 338
gtggacgact gtggcagaat ggaga                                       25

<210> SEQ ID NO 339
<211> LENGTH: 26
<212> TYPE: DNA
<213> ORGANISM: Artificial Sequence
<220> FEATURE:
<223> OTHER INFORMATION: Probe

<400> SEQUENCE: 339
ggtcaagagt tccatgtgga ctagca                                      26

<210> SEQ ID NO 340
<211> LENGTH: 26
<212> TYPE: DNA
<213> ORGANISM: Artificial Sequence
<220> FEATURE:

<223> OTHER INFORMATION: Probe

<400> SEQUENCE: 340
ctgctgtctg ggaatgtctg cctgct                    26

<210> SEQ ID NO 341
<211> LENGTH: 25
<212> TYPE: DNA
<213> ORGANISM: Artificial Sequence
<220> FEATURE:
<223> OTHER INFORMATION: Probe

<400> SEQUENCE: 341
ccacgagagg atgtctccca gcctt                     25

<210> SEQ ID NO 342
<211> LENGTH: 25
<212> TYPE: DNA
<213> ORGANISM: Artificial Sequence
<220> FEATURE:
<223> OTHER INFORMATION: Probe

<400> SEQUENCE: 342
cgataccagg atagcagttt actct                     25

<210> SEQ ID NO 343
<211> LENGTH: 28
<212> TYPE: DNA
<213> ORGANISM: Artificial Sequence
<220> FEATURE:
<223> OTHER INFORMATION: Probe

<400> SEQUENCE: 343
ccacgatgct cctggacgcc ggccccca                  28

<210> SEQ ID NO 344
<211> LENGTH: 24
<212> TYPE: DNA
<213> ORGANISM: Artificial Sequence
<220> FEATURE:
<223> OTHER INFORMATION: Probe

<400> SEQUENCE: 344
cggagcagta cggccaggtg acca                      24

<210> SEQ ID NO 345
<211> LENGTH: 26
<212> TYPE: DNA
<213> ORGANISM: Artificial Sequence
<220> FEATURE:
<223> OTHER INFORMATION: Probe

<400> SEQUENCE: 345
gattcgcagg gttctttcag taatgt                    26

<210> SEQ ID NO 346
<211> LENGTH: 26
<212> TYPE: DNA
<213> ORGANISM: Artificial Sequence
<220> FEATURE:
<223> OTHER INFORMATION: Probe

<400> SEQUENCE: 346
gattcgcagg gttctttcag taatgt                    26

```
<210> SEQ ID NO 347
<211> LENGTH: 24
<212> TYPE: DNA
<213> ORGANISM: Artificial Sequence
<220> FEATURE:
<223> OTHER INFORMATION: Probe

<400> SEQUENCE: 347
cgccgagatg caggaccgtg aact                                              24

<210> SEQ ID NO 348
<211> LENGTH: 24
<212> TYPE: DNA
<213> ORGANISM: Artificial Sequence
<220> FEATURE:
<223> OTHER INFORMATION: Probe

<400> SEQUENCE: 348
ggaggtgtgg acgtgcatgt gctt                                              24

<210> SEQ ID NO 349
<211> LENGTH: 23
<212> TYPE: DNA
<213> ORGANISM: Artificial Sequence
<220> FEATURE:
<223> OTHER INFORMATION: Probe

<400> SEQUENCE: 349
gccatgacga tgctcctgga cgg                                               23

<210> SEQ ID NO 350
<211> LENGTH: 23
<212> TYPE: DNA
<213> ORGANISM: Artificial Sequence
<220> FEATURE:
<223> OTHER INFORMATION: Probe

<400> SEQUENCE: 350
cctcagacgt accattcgtt aaa                                               23

<210> SEQ ID NO 351
<211> LENGTH: 24
<212> TYPE: DNA
<213> ORGANISM: Artificial Sequence
<220> FEATURE:
<223> OTHER INFORMATION: Probe

<400> SEQUENCE: 351
cggcaacatg gtgcggtcgg ggaa                                              24

<210> SEQ ID NO 352
<211> LENGTH: 29
<212> TYPE: DNA
<213> ORGANISM: Artificial Sequence
<220> FEATURE:
<223> OTHER INFORMATION: Probe

<400> SEQUENCE: 352
ccaacatggt gcggtcgggg aataaggca                                         29

<210> SEQ ID NO 353
<211> LENGTH: 28
<212> TYPE: DNA
<213> ORGANISM: Artificial Sequence
<220> FEATURE:
<223> OTHER INFORMATION: Probe
```

<400> SEQUENCE: 353
ccaccatgag tactgcagat gcacttga                                              28

<210> SEQ ID NO 354
<211> LENGTH: 28
<212> TYPE: DNA
<213> ORGANISM: Artificial Sequence
<220> FEATURE:
<223> OTHER INFORMATION: Probe

<400> SEQUENCE: 354
cctgtatctt gcatgtttct cagggcca                                              28

<210> SEQ ID NO 355
<211> LENGTH: 19
<212> TYPE: DNA
<213> ORGANISM: Artificial Sequence
<220> FEATURE:
<223> OTHER INFORMATION: Probe

<400> SEQUENCE: 355
ccacgatgtg gaaactgct                                                        19

<210> SEQ ID NO 356
<211> LENGTH: 24
<212> TYPE: DNA
<213> ORGANISM: Artificial Sequence
<220> FEATURE:
<223> OTHER INFORMATION: Probe

<400> SEQUENCE: 356
gcctgaagta gatgcttact agga                                                  24

<210> SEQ ID NO 357
<211> LENGTH: 25
<212> TYPE: DNA
<213> ORGANISM: Artificial Sequence
<220> FEATURE:
<223> OTHER INFORMATION: Probe

<400> SEQUENCE: 357
gttgttgcca ctccgccacc atgtt                                                 25

<210> SEQ ID NO 358
<211> LENGTH: 26
<212> TYPE: DNA
<213> ORGANISM: Artificial Sequence
<220> FEATURE:
<223> OTHER INFORMATION: Probe

<400> SEQUENCE: 358
gcctaagatc cttcttcatc ctcgat                                                26

<210> SEQ ID NO 359
<211> LENGTH: 30
<212> TYPE: DNA
<213> ORGANISM: Artificial Sequence
<220> FEATURE:
<223> OTHER INFORMATION: Probe

<400> SEQUENCE: 359
cgaccatggt gcggcctgtg agacataaga                                            30

<210> SEQ ID NO 360
<211> LENGTH: 24

```
<212> TYPE: DNA
<213> ORGANISM: Artificial Sequence
<220> FEATURE:
<223> OTHER INFORMATION: Probe

<400> SEQUENCE: 360
ccacactcag gtgctagtgg catt                                          24

<210> SEQ ID NO 361
<211> LENGTH: 29
<212> TYPE: DNA
<213> ORGANISM: Artificial Sequence
<220> FEATURE:
<223> OTHER INFORMATION: Probe

<400> SEQUENCE: 361
ccagcatggg tagcaagaaa ctaaaacga                                     29

<210> SEQ ID NO 362
<211> LENGTH: 25
<212> TYPE: DNA
<213> ORGANISM: Artificial Sequence
<220> FEATURE:
<223> OTHER INFORMATION: Probe

<400> SEQUENCE: 362
ctgtctctag gaatttccat aggct                                         25

<210> SEQ ID NO 363
<211> LENGTH: 26
<212> TYPE: DNA
<213> ORGANISM: Artificial Sequence
<220> FEATURE:
<223> OTHER INFORMATION: Probe

<400> SEQUENCE: 363
gcaagatgtc tgggactgag gaagca                                        26

<210> SEQ ID NO 364
<211> LENGTH: 26
<212> TYPE: DNA
<213> ORGANISM: Artificial Sequence
<220> FEATURE:
<223> OTHER INFORMATION: Probe

<400> SEQUENCE: 364
gtggcctgag cctcagtaag atggat                                        26

<210> SEQ ID NO 365
<211> LENGTH: 25
<212> TYPE: DNA
<213> ORGANISM: Artificial Sequence
<220> FEATURE:
<223> OTHER INFORMATION: Probe

<400> SEQUENCE: 365
ggcgcgctaa cgacgttcct aacaa                                         25

<210> SEQ ID NO 366
<211> LENGTH: 26
<212> TYPE: DNA
<213> ORGANISM: Artificial Sequence
<220> FEATURE:
<223> OTHER INFORMATION: Probe

<400> SEQUENCE: 366
```
cactatgtgc cagtagcttg agtggt                                           26

<210> SEQ ID NO 367
<211> LENGTH: 26
<212> TYPE: DNA
<213> ORGANISM: Artificial Sequence
<220> FEATURE:
<223> OTHER INFORMATION: Probe

<400> SEQUENCE: 367
cgagaatgga ggtggaggcc gtctgt                                           26

<210> SEQ ID NO 368
<211> LENGTH: 24
<212> TYPE: DNA
<213> ORGANISM: Artificial Sequence
<220> FEATURE:
<223> OTHER INFORMATION: Probe

<400> SEQUENCE: 368
gtcagtcagt gaagtctctg ctct                                             24

<210> SEQ ID NO 369
<211> LENGTH: 28
<212> TYPE: DNA
<213> ORGANISM: Artificial Sequence
<220> FEATURE:
<223> OTHER INFORMATION: Probe

<400> SEQUENCE: 369
ccacgatggt gccctccagc ccagcggt                                         28

<210> SEQ ID NO 370
<211> LENGTH: 24
<212> TYPE: DNA
<213> ORGANISM: Artificial Sequence
<220> FEATURE:
<223> OTHER INFORMATION: Probe

<400> SEQUENCE: 370
gcccgagagt cactggttca catt                                             24

<210> SEQ ID NO 371
<211> LENGTH: 30
<212> TYPE: DNA
<213> ORGANISM: Artificial Sequence
<220> FEATURE:
<223> OTHER INFORMATION: Probe

<400> SEQUENCE: 371
ccagcatggt ggacatgatg gacttgccca                                       30

<210> SEQ ID NO 372
<211> LENGTH: 24
<212> TYPE: DNA
<213> ORGANISM: Artificial Sequence
<220> FEATURE:
<223> OTHER INFORMATION: Probe

<400> SEQUENCE: 372
gatcaatcat gttgcacaat ccct                                             24

<210> SEQ ID NO 373
<211> LENGTH: 27
<212> TYPE: DNA
<213> ORGANISM: Artificial Sequence

```
<220> FEATURE:
<223> OTHER INFORMATION: Probe

<400> SEQUENCE: 373
cgaccatgga gggaggcttg aagagga                                              27

<210> SEQ ID NO 374
<211> LENGTH: 26
<212> TYPE: DNA
<213> ORGANISM: Artificial Sequence
<220> FEATURE:
<223> OTHER INFORMATION: Probe

<400> SEQUENCE: 374
ccctctatca cagttttagg acccca                                               26

<210> SEQ ID NO 375
<211> LENGTH: 24
<212> TYPE: DNA
<213> ORGANISM: Artificial Sequence
<220> FEATURE:
<223> OTHER INFORMATION: Probe

<400> SEQUENCE: 375
ccgcgatgtg tagtgccttc cata                                                 24

<210> SEQ ID NO 376
<211> LENGTH: 24
<212> TYPE: DNA
<213> ORGANISM: Artificial Sequence
<220> FEATURE:
<223> OTHER INFORMATION: Probe

<400> SEQUENCE: 376
gcgtagtacc ctgcaaaaga ctat                                                 24

<210> SEQ ID NO 377
<211> LENGTH: 30
<212> TYPE: DNA
<213> ORGANISM: Artificial Sequence
<220> FEATURE:
<223> OTHER INFORMATION: Probe

<400> SEQUENCE: 377
gcaccatgga tttggatcta ctggacctga                                           30

<210> SEQ ID NO 378
<211> LENGTH: 27
<212> TYPE: DNA
<213> ORGANISM: Artificial Sequence
<220> FEATURE:
<223> OTHER INFORMATION: Probe

<400> SEQUENCE: 378
gtgttgtgca gccgccaccg tgtcagt                                              27

<210> SEQ ID NO 379
<211> LENGTH: 26
<212> TYPE: DNA
<213> ORGANISM: Artificial Sequence
<220> FEATURE:
<223> OTHER INFORMATION: Probe

<400> SEQUENCE: 379
ccaccatgga gagaaaaata agcaga                                               26
```

```
<210> SEQ ID NO 380
<211> LENGTH: 27
<212> TYPE: DNA
<213> ORGANISM: Artificial Sequence
<220> FEATURE:
<223> OTHER INFORMATION: Probe

<400> SEQUENCE: 380
ctcatcaaag aggtcttctg ggctgct                                    27
```